United States Patent
Keyt et al.

(10) Patent No.: US 10,954,302 B2
(45) Date of Patent: Mar. 23, 2021

(54) ANTI-PD-L1 ANTIBODIES

(71) Applicant: IGM BIOSCIENCES, INC., Mountain View, CA (US)

(72) Inventors: Bruce Keyt, Hillsborough, CA (US); Leonard George Presta, San Francisco, CA (US); Ramesh Baliga, Redwood City, CA (US)

(73) Assignee: IGM Biosciences, Inc., Mountain View, CA (US)

( * ) Notice: Subject to any disclaimer, the term of this patent is extended or adjusted under 35 U.S.C. 154(b) by 141 days.

(21) Appl. No.: 16/098,479

(22) PCT Filed: May 9, 2017

(86) PCT No.: PCT/US2017/031791
§ 371 (c)(1),
(2) Date: Nov. 2, 2018

(87) PCT Pub. No.: WO2017/196867
PCT Pub. Date: Nov. 16, 2017

(65) Prior Publication Data
US 2019/0338031 A1    Nov. 7, 2019

Related U.S. Application Data

(60) Provisional application No. 62/333,643, filed on May 9, 2016.

(51) Int. Cl.
*C07K 16/28* (2006.01)
*C07K 16/30* (2006.01)
*G01N 33/68* (2006.01)

(52) U.S. Cl.
CPC .......... *C07K 16/2827* (2013.01); *C07K 16/30* (2013.01); *G01N 33/6854* (2013.01); *C07K 2317/21* (2013.01); *C07K 2317/24* (2013.01); *C07K 2317/31* (2013.01); *C07K 2317/33* (2013.01); *C07K 2317/34* (2013.01); *C07K 2317/622* (2013.01)

(58) Field of Classification Search
CPC ............ C07K 16/2827; C07K 2317/24; C07K 2317/33; G01N 33/6854
USPC ...................................... 424/133.1
See application file for complete search history.

(56) References Cited

U.S. PATENT DOCUMENTS

| | | | |
|---|---|---|---|
| 8,377,435 B2 | 2/2013 | Bhat | |
| 9,409,976 B2 | 8/2016 | Teng | |
| 9,458,241 B2 | 10/2016 | Bhat | |
| 9,938,347 B2 | 4/2018 | Wang | |
| 9,951,134 B2 | 4/2018 | Keyt | |
| 10,351,631 B2 | 7/2019 | Keyt | |
| 10,400,038 B2 | 9/2019 | Keyt | |
| 10,570,191 B2 | 2/2020 | Keyt | |
| 10,604,559 B2 | 3/2020 | Carroll | |
| 10,618,978 B2 | 4/2020 | Keyt | |
| 10,689,449 B2 | 6/2020 | Wang | |
| 10,787,520 B2 | 9/2020 | Keyt | |
| 10,899,835 B2 | 1/2021 | Baliga | |
| 2005/0287153 A1 | 12/2005 | Dennis | |
| 2016/0222132 A1 | 8/2016 | Keyt | |
| 2016/0368971 A1 | 12/2016 | Keyt | |
| 2018/0009897 A1 | 1/2018 | Wang | |
| 2018/0118814 A1 | 5/2018 | Carroll | |
| 2018/0118816 A1 | 5/2018 | Keyt | |
| 2018/0265596 A1 | 9/2018 | Keyt | |
| 2019/0002566 A1 | 1/2019 | Keyt | |
| 2019/0100597 A1 | 4/2019 | Keyt | |
| 2019/0185570 A1 | 6/2019 | Keyt | |
| 2019/0330360 A1 | 10/2019 | Wang | |
| 2019/0330374 A1 | 10/2019 | Wang | |
| 2019/0338040 A1 | 11/2019 | Keyt | |
| 2019/0338041 A1 | 11/2019 | Baliga | |
| 2020/0190190 A1 | 6/2020 | Keyt | |
| 2020/0239572 A1 | 7/2020 | Baliga | |
| 2020/0255546 A1 | 8/2020 | Keyt | |
| 2020/0377577 A1 | 12/2020 | Keyt | |
| 2021/0002353 A1 | 1/2021 | Carroll | |

FOREIGN PATENT DOCUMENTS

| | | |
|---|---|---|
| WO | 2004110143 | 12/2004 |
| WO | 2006052641 | 5/2006 |
| WO | 2013079174 | 6/2013 |
| WO | 2013120012 | 8/2013 |
| WO | 2015053887 | 4/2015 |
| WO | 2015112805 | 7/2015 |
| WO | 2015120474 | 8/2015 |
| WO | 2015153912 | 10/2015 |
| WO | 2015181342 | 12/2015 |
| WO | 2016000619 | 1/2016 |
| WO | 2016118641 | 7/2016 |
| WO | 2016141303 | 9/2016 |
| WO | 2016154593 | 9/2016 |
| WO | 2016168758 | 10/2016 |

(Continued)

OTHER PUBLICATIONS

Li et al (J Immunother Cancer. Jun. 4, 2018;6(1):45).*
Deng et al (MABs 2016;8(3):593-603; Epub Feb. 26, 2016).*
Luan et al (Int. Immunpharnncol Feb. 2016;31:248-56; Epub Jan. 12, 2016).*
Castro, C., et al., (2014), "Putting J chain back on the map: how might its expression define plasma cell development?", The Journal of Immunology, 193: 3248-3255.
Duramad, O., et al., (2014), "IGM-55.5 a novel monoclonal human recombinant IgM antibody with potent activity against B cell leukemia and lymphoma" IGM Biosciences, Inc.—Research and Development SRI International—Cancer Pharmacology, Stanford—Department of Obstetrics and Gynecology, Abstract No. 645 AACR Annual Meeting, Apr. 5-9, 2014, San Diego CA.
Hensel, F., et al., (2013), "Early development of PAT-SM6 for the treatment of melanoma", 23(4): 264-275.

(Continued)

*Primary Examiner* — Lynn A Bristol

(57) ABSTRACT

Aspects of the invention include isolated anti-PD-L1 antibodies, as well as compositions containing such antibodies, and methods of using the same in the treatment of diseases or conditions that are mediated by PD-L1 signaling.

19 Claims, 11 Drawing Sheets

Specification includes a Sequence Listing.

(56) References Cited

FOREIGN PATENT DOCUMENTS

| WO | 2017059380 | 4/2017 |
| --- | --- | --- |
| WO | 2017059387 | 4/2017 |
| WO | 2018017761 | 1/2018 |
| WO | 2018017763 | 1/2018 |
| WO | 2018017888 | 1/2018 |
| WO | 2018017889 | 1/2018 |
| WO | 2018187702 | 10/2018 |
| WO | 2019165340 | 8/2019 |
| WO | 2019169314 | 9/2019 |
| WO | 2020086745 | 4/2020 |
| WO | 2020163646 | 8/2020 |

OTHER PUBLICATIONS

Rasche, L., et al., (2015), "GRP78-directed immunotherapy in relapsed or refractory multiple myeloma—results from a phase 1 trial with the monoclonal immunoglobulin M antibody PAT-SM6", Haematologica, J. Mol. Biol, 100(3): 377-384.

Blank, C., et. al., (2005), "Interaction of PD-L1 on tumor cells with PD-1 on tumor-specific T cells as a mechanism of immune evasion: implications for tumor immunotherapy", Cancer Immunol Immunother, 54: 307-314.

Carter, L., et al., (2002), "PD-1: PD-L inhibitory pathway affects both CD4+ and CD8+ T cells and is overcome by IL-2", Eur. J. Immunol., 32: 634-643.

Chintalacharuvu et al., "Hybrid IgA2/igG1 Antibodies with Tailor-Made Effector Functions", Clinical Immunology, Oct. 2001, pp. 21-31, vol. 101, No. 1, pp. 21-31.

Dennis, M., et al. (2002), "Albumin Binding as a General Strategy for Improving the Pharmacokinetics of Proteins", J. Biol. Chem. 277(38): 35035-35043.

Dong, H., et al., (2002), "Tumor-associated B7-H1 promotes T-cell apoptosis: A potential mechanism of immune evasion", Nature Medicine, vol. 8(8): 793-800.

Freeman, G., et al., (2000), "Engagement of the PD-1 Immunoinhibitory Receptor by a Novel B7 Family Member Leads to Negative Regulation of Lymphocyte Activation", J. Exp. Med, vol. 192(7): 1027-1034.

Hansen, J., et al., (1980), "Monoclonal antibodies indentifying a novel T-Cell antigen and Ia antigens of human lymphocytes", Immunogenetics, 10: 247-260.

Hutloff, A., et al., (1999), "ICOS is an inducible T-cell co-stimulator structurally and functionally related to CD28", Nature, 397: 263-266.

International Search Report and Written Opinion dated Jul. 21, 2018 issued in PCT Patent Application No. PCT/US2017/031791.

Iwai, Y., et al., (2002), "Involvement of PD-L1 on tumor cells in the escape from host immune system and tumor immunotherapy by PD-L1 blockade", PNAS, 99(19): 12293-12297.

Latchman, Y., et al., (2001), "PD-L2 is a second ligand for PD-1 and inhibits T cell activation", Nature Immunology, vol. 2(3):261-268.

Lin, D., et al., (2008), "The PD-1/PD-L1 complex resembles the antigen-binding Fv domains of antibodies and T cell receptors", PNAS, 105(8): 3011-3016.

Lines, J., et al, (2014), "VISTA Is an Immune Checkpoint Molecule for Human T Cells", Cancer Research 74(7): 1924-1932.

Maekawa, N., et al., (2014), "Expression of PD-L1 on Canine Tumor Cells and Enhancement of IFN-γ Production from Tumor-Infiltrating Cells by PD-L1 Blockade", PLOS One, vol. 9(6), e98415.

Medina, P., et. al., (2016), "PD-1 Pathway Inhibitors: Immuno-Oncology Agents for Restoring Antitumor Immune Responses", vol. 36(3): 317-334.

Ohigashi, Y., et. al., (2005), "Clinical Significance of Programmed Death-1 Ligand-1 and Programmed Death-1 Ligand-2 Expression in Human Esophageal Cancer", Clin Cancer Res, vol. 11(8): 2947-2953.

Pardoll, D.M., (2012), "The blockade of immune checkpoints in cancer immunotherapy" Nat. Rev. Cancer 12(4): 252-264.

Roopenian, D., et al., (2007), "FcRn: the neonatal Fc receptor comes of age", Nature Reviews, vol. 7, 715-725.

Rosenburg, J., et. al., (2016), "Atezolizumab in patients with locally advanced and metastatic urothelial carcinoma who have progressed following treatment with platinum-based chemotherapy: a single arm, phase 2 trial", Lancet, 387 (10031): 1909-1920.

UnkProtKB Q15116, "Human PD-1 specifically includes the 288 amino acids long PD-1 human polypeptide provided in UniProtKB", 15 pages.

UnkProtKB Q9NZQ7, "Human PD-L1 specifically includes the 290 amino acids long PD-L1 human polypeptide of SEQ ID No. 48", 19 pages.

Yu, X., et al. (2009), "The surface protein TIGIT suppresses T cell activation by promoting the generation of mature immunoregulatory dendritic cells", Nature Immunology, vol. 10(1): 48-57.

* cited by examiner

ANTI-PD-L1 ANTIBODIES

CROSS-REFERENCE TO RELATED APPLICATIONS

This application is a US National Stage Entry of PCT Application No. PCT/US2017/031791, filed May 9, 2017, which claims priority benefit of the filing date of U.S. Provisional Patent Application Ser. No. 62/333,643, filed on May 9, 2016, which are each hereby incorporated by reference in their entireties.

REFERENCE TO SEQUENCE LISTING SUBMITTED ELECTRONICALLY

The instant application contains a Sequence Listing which has been submitted electronically in ASCII format and is hereby incorporated by reference in its entirety. Said ASCII copy, created on Aug. 9, 2018, is named Sequence-Listing and is 65981 bytes in size.

FIELD OF THE INVENTION

The present invention concerns isolated anti-PD-L1 antibodies, and their preparation and uses.

BACKGROUND OF THE INVENTION

Programmed cell death protein 1 (PD-1) is a cell surface receptor belonging to the immunoglobulin superfamily, which includes cell surface and soluble proteins that are involved with recognition, binding, and adhesion processes of cells. The initial members of this family were discovered due to their functional effect on augmenting T-cell proliferation following the addition of monoclonal antibodies (Hutloff et al. (1999) *Nature* 397:263-266; Hansen et al. (1980) *Immunogenics* 10:247-260). Two cell surface glycoprotein ligands for PD-1, referred to as PD-L1 and PD-L2, have been identified, and have been shown to downregulate T-cell activation and cytokine secretion upon binding to PD-1 (Freeman et al. (2000) *J Exp Med* 192:1027-34; Latchman et al. (2001) *Nat Immunol* 2:261-8; Carter et al. (2002) *Eur J Immunol* 32:634-43; Ohigashi et al. (2005) *Clin Cancer Res* 11:2947-53). Both PD-L1 and PD-L2 are B7 homologs that bind to PD-1, but do not bind to other CD28 family members (Blank et al. (2004). Expression of PD-L1 on the cell surface has also been shown to be upregulated through IFN-γ stimulation.

PD-L1 expression has been found in several murine and human cancers, including human lung, ovarian and colon carcinoma, as well as various myelomas (Iwai et al. (2002) *PNAS* 99:12293-7; Ohigashi et al. (2005) *Clin Cancer Res* 11:2947-53). PD-L1 has also been suggested to play a role in tumor immunity by increasing apoptosis of antigen-specific T-cell clones (Dong et al. (2002) *Nat Med* 8:793-800). As such, targeting of the interaction between PD-1 and PD-L1 is an area of particular interest for therapeutic intervention. There is a need for therapeutic compositions, such as anti-PD-L1 antibodies, directed against targets in this pathway.

SUMMARY OF THE INVENTION

Aspects of the invention include isolated anti-PD-L1 antibodies, as well as compositions containing such antibodies, and methods of using the same in the treatment of diseases or conditions that are mediated by PD-L1 signaling.

In some embodiments, an isolated anti-PD-L1 antibody, or an antigen-binding fragment thereof, comprises a heavy chain variable region that comprises: (i) an HVR-H1 sequence having at least about 99% sequence identity to the sequence of GFSLTSYDIS (SEQ ID NO: 4); (ii) an HVR-H2 sequence having at least about 99% sequence identity to the sequence of VIWTGVGTN (SEQ ID NO: 5); and (iii) an HVR-H3 sequence having at least about 99% sequence identity to the sequence of DPYYYGMDY (SEQ ID NO: 6). In some embodiments, the HVR-H1 sequence comprises the sequence of GFSLTSYDIS (SEQ ID NO: 4); the HVR-H2 sequence comprises the sequence of VIWTGVGTN (SEQ ID NO: 5); and the HVR-H3 sequence comprises the sequence of DPYYYGMDY (SEQ ID NO: 6). In some embodiments, an isolated anti-PD-L1 antibody further comprises a light chain variable region comprising at least one HVR sequence selected from the group consisting of: (i) HVR-L1 comprising at least about 99% sequence identity to the sequence of RASQDISIWLS (SEQ ID NO: 1); (ii) HVR-L2 comprising at least about 99% sequence identity to the sequence of KASNLHT (SEQ ID NO: 2); and (iii) HVR-L3 comprising at least about 99% sequence identity to the sequence of LQSQSFPRT (SEQ ID NO: 3). In certain embodiments, the light chain variable region comprises all of said HVR-L1, HVR-L2, and HVR-L3 sequences.

In some embodiments, an anti-DP-L1 antibody, or antigen-binding fragment thereof, comprises: (i) an HVR-L1 that comprises the sequence of RASQDISIWLS (SEQ ID NO: 1); (ii) an HVR-L2 that comprises the sequence of KASNLHT (SEQ ID NO: 2); and (iii) an HVR-L3 that comprises the sequence of LQSQSFPRT (SEQ ID NO: 3). In some embodiments, the antibody, or antigen-binding fragment, comprises: (i) an HVR-L1 that comprises the sequence of RASQDISIWLS (SEQ ID NO: 1); (ii) an HVR-L2 that comprises the sequence of KASNLHT (SEQ ID NO: 2); and (iii) an HVR-L3 that comprises the sequence of LQSQSFPRT (SEQ ID NO: 3).

In some embodiments, the antibody, or antigen-binding fragment, is a monoclonal antibody. In some embodiments, the antibody is a chimeric, humanized, or human antibody. In some embodiments, the heavy chain variable region comprises a framework sequence. In some embodiments, at least a portion of the framework sequence comprises a human framework sequence. In some embodiments, at least a portion of the framework sequence comprises a human consensus framework sequence. In some embodiments, the framework sequence comprises a framework region 1 (FR1) sequence selected from the group consisting of: SEQ ID NOS: 7, 8, 9, 10 and 11. In some embodiments, the framework sequence comprises a framework region 2 (FR2) sequence selected from the group consisting of: SEQ ID NOS: 12, 13, 14, 15 and 16. In some embodiments, the framework sequence comprises a framework region 3 (FR3) sequence selected from the group consisting of: SEQ ID NOS: 17, 18, 19, 20, 21, 22, 23 and 24. In some embodiments, the framework sequence comprises a framework region 4 (FR4) sequence selected from the group consisting of: SEQ ID NOS: 25 and 26. In some embodiments, the framework sequence comprises an FR1 sequence selected from the group consisting of: SEQ ID NOS: 7, 8, 9, 10 and 11; an FR2 sequence selected from the group consisting of: SEQ ID NOS: 12, 13, 14, 15 and 16; an FR3 sequence selected from the group consisting of: SEQ ID NOS: 17, 18, 19, 20, 21, 22, 23 and 24; and an FR4 sequence selected from the group consisting of: SEQ ID NOS: 25 and 26.

In some embodiments, the light chain variable region comprises a framework sequence. In some embodiments, at least a portion of the framework sequence comprises a human framework sequence. In some embodiments, at least a portion of the framework sequence comprises a human consensus framework sequence. In some embodiments, the framework sequence comprises a framework region 1 (FR1) sequence selected from the group consisting of: SEQ ID NOS: 27, 28 and 29. In some embodiments, the framework sequence comprises a framework region 2 (FR2) sequence selected from the group consisting of: SEQ ID NOS: 30 and 31. In some embodiments, the framework sequence comprises a framework region 3 (FR3) sequence selected from the group consisting of: SEQ ID NOS: 32 and 33. In some embodiments, the framework sequence comprises a framework region 4 (FR4) sequence selected from the group consisting of: SEQ ID NOS: 34 and 35. In some embodiments, the framework region comprises: an FR1 sequence selected from the group consisting of: SEQ ID NOS: 27, 28 and 29; an FR2 sequence selected from the group consisting of: SEQ ID NOS: 30 and 31; an FR3 sequence selected from the group consisting of: SEQ ID NOS: 32 and 33; and an FR4 sequence selected from the group consisting of: SEQ ID NOS: 34 and 35.

In some embodiments, an isolated anti-PD-L1 antibody, or an antigen-binding fragment thereof, comprises a heavy chain variable domain having at least about 90% sequence identity to SEQ ID NO: 45 and/or a light chain variable domain having at least about 90% sequence identity to SEQ ID NO: 46. In some embodiments, an isolated anti-PD-L1 antibody, or antigen-binding fragment thereof, comprises a heavy chain variable domain comprising SEQ ID NO: 45 and/or a light chain variable domain comprising SEQ ID NO: 46.

In some embodiments, the antibody is a monoclonal antibody. In some embodiments, the antibody is a chimeric, humanized or human antibody.

In some embodiments, an isolated anti-PD-L1 antibody, or antigen-binding fragment thereof, comprises a heavy chain variable domain having at least 90% sequence identity to any one of SEQ ID NOS: 36, 37, 38, 39, 40, 41 or 42 and/or a light chain variable domain having at least 90% sequence identity to any one of SEQ ID NOS: 43 or 44. In some embodiments, an isolated anti-PD-L1 antibody, or antigen-binding fragment thereof, comprising a heavy chain variable domain comprising any one of SEQ ID NOS: 36, 37, 38, 39, 40, 41 or 42 and/or a light chain variable domain comprising any one of SEQ ID NOS: 43 or 44. In some embodiments, an antibody: (i) binds substantially to the same epitope as an anti-PD-L1 antibody comprising a heavy chain variable domain of any one of SEQ ID NOS: 36, 37, 38, 39, 40, 41 or 42, and a light chain variable domain of any one of SEQ ID NOS: 43 or 44; or (ii) competes for binding to the same epitope as an anti-PD-L1 antibody comprising a heavy chain variable domain of any one of SEQ ID NOS: 36, 37, 38, 39, 40, 41 or 42, and a light chain variable domain of any one of SEQ ID NOS: 43 or 44. In some embodiments, an anti-PD-L1 antibody, or an antigen-binding fragment thereof, made by the process of: (a) culturing a cell expressing an antibody comprising a heavy chain variable domain of any one of SEQ ID NOs: 36, 37, 38, 39, 40, 41 or 42, and a light chain variable domain of any one of SEQ ID NOs: 43 or 44; and (b) isolating the antibody from the cell or from a cell culturing medium in which the cell is cultured. In some embodiments, the antibody is a monoclonal antibody. In some embodiments, the antibody is a chimeric, humanized or human antibody.

In some embodiments, an antibody or antigen-binding fragment is monospecific. In some embodiments, an antibody or antigen-binding fragment is bispecific. In some embodiments, the antibody or antigen-binding fragment binds to a PD-L1 protein and a cell surface protein. In some embodiments, the cell surface protein is selected from the group consisting of: CD20, EGFR, HER2, CTLA-4, TIM3, LAG3, VISTA and TIGIT. In some embodiments, the antibody or antigen-binding fragment is multispecific. In some embodiments, the antibody or antigen-binding fragment binds to a PD-L1 protein and one or more cell surface proteins. In some embodiments, the cell surface proteins are selected from the group consisting of: CD20, EGFR, HER2, CTLA-4, TIM3, LAG3, VISTA and TIGIT.

In some embodiments, an antigen-binding fragment is selected from the group consisting of: Fab, Fab', F(ab)$_2$, F(ab')$_2$, Fv, scFv, and single domain antibody. In some embodiments, an antibody comprises a kappa light chain or a lambda light chain. In some embodiments, an antibody is an IgG, IgM, IgA, IgD, or IgE isotype. In some embodiments, an antibody is an IgG isotype, and the antibody is a subclass selected from the group consisting of: IgG1, IgG2, IgG3 and IgG4. In some embodiments, an antibody is an IgM isotype. In some embodiments, an antibody comprises a J-chain. In some embodiments, an antibody is an IgA isotype, and wherein the antibody is a subclass selected from the group consisting of: IgA1 and IgA2. In some embodiments, the antibody comprises a J-chain. In some embodiments, an antibody is an IgG/IgM or an IgG/IgA hybrid antibody comprising a J-chain.

In some embodiments, a J-chain is a modified J-chain comprising an extraneous binding moiety. In some embodiments, the extraneous binding moiety is selected from the group consisting of: antibodies, antigen-binding fragments of antibodies, antibody-drug conjugates, antibody-like molecules, antigen-binding fragments of antibody-like molecules, soluble and membrane-bound proteins, ligands, and receptors. In some embodiments, the extraneous moiety is an antigen-binding fragment of an antibody, and is selected from the group consisting of: Fab, Fab', F(ab)$_2$, F(ab')$_2$, Fv, scFv, and single domain antibody. In some embodiments, the antigen-binding fragment is an scFv.

In some embodiments, the extraneous binding moiety affects a T-cell signaling pathway. In some embodiments, the extraneous binding moiety antagonizes a T-cell inhibitory signaling pathway. In some embodiments, the extraneous binding moiety binds to a cell surface protein selected from the group consisting of: CTLA-4, PD-1, TIM3, LAG3, BTLA, VISTA and TIGIT. In some embodiments, the extraneous binding moiety binds to an albumin protein, or a fragment of an albumin protein. In some embodiments, the extraneous binding moiety comprises an albumin-binding peptide. In some embodiments, the extraneous binding moiety comprises an albumin-binding antibody fragment. In some embodiments, the albumin-binding antibody fragment is selected from the group consisting of: Fab, scFv, VHH, scFab and dAb. In some embodiments, the extraneous binding moiety comprises an FcRn-binding peptide. In some embodiments, the extraneous binding moiety comprises an FcRn-binding antibody fragment. In some embodiments, the FcRn-binding antibody fragment is selected from the group consisting of: Fab, scFv, VHH, scFab and dAb. In some embodiments, the extraneous binding moiety comprises an Fc domain.

Aspects of the invention include an IgM, IgA, IgG/IgM or IgG/IgA antibody, or antigen-binding fragment, comprising a modified J-chain comprising an extraneous binding moiety, wherein the antibody binds to a cell surface protein, and wherein the extraneous binding moiety comprises an anti- PD-L1 antibody, or an antigen-binding fragment, as described herein. In some embodiments, the cell surface protein is selected from the group consisting of: CD20, EGFR, HER2, CTLA-4, PD-1, TIM3, LAG3, BTLA, VISTA and TIGIT.

In some embodiments, the extraneous binding moiety binds to an effector cell. In some embodiments, the effector cell is selected from the group consisting of: T-cells, natural killer (NK) cells, macrophages and neutrophils. In some embodiments, the effector cell is a T-cell. In some embodiments, the extraneous binding moiety binds to a CD3 protein (e.g., a CD3E protein) on the T-cell. In some embodiments, the effector cell is an NK cell. In some embodiments, the extraneous binding moiety binds to a target on the NK cell selected from the group consisting of: CD16, CD64 and NKG2D. In some embodiments, the effector cell is a macrophage. In some embodiments, the extraneous binding moiety binds to a CD14 on the macrophage. In some embodiments, the effector cell is a neutrophil. In some embodiments, the extraneous binding moiety binds to CD16b or CD177 on the neutrophil.

In some embodiments, an antibody, or antigen-binding fragment, is a PD-L1 antagonist. In some embodiments, an antibody, or antigen-binding fragment, antagonizes a PD-L1 signaling pathway. In some embodiments, an antibody, or antigen-binding fragment, antagonizes an interaction between a PD-L1 protein and a PD-1 protein. In some embodiments, an antibody, or antigen-binding fragment, inhibits binding between a PD-L1 protein and a PD-1 protein. In some embodiments, an antibody, or antigen-binding fragment, blocks binding between a PD-L1 protein and a PD-1 protein. In some embodiments, an antibody, or an antigen-binding fragment, binds to a PD-L1 protein and inhibits one or more functions of a PD-1 protein.

Aspects of the invention include a polynucleotide encoding a heavy chain and/or a light chain of an antibody as described herein. Aspects of the invention include a vector comprising a polynucleotide as described herein. Aspects of the invention include a host cell comprising a vector as described herein. In some embodiments, the host cell is a prokaryotic cell. In some embodiments, the host cell is a eukaryotic cell.

Aspects of the invention include kits that comprise an anti-PD-L1 antibody as described herein.

Aspects of the invention include methods of producing an isolated anti-PD-L1 antibody, the method comprising: transfecting a host cell with a nucleic acid comprising a polynucleotide encoding a heavy chain and/or a light chain of an anti-PD-L1 antibody as described herein; culturing the host cell under suitable conditions for producing the anti-PD-L1 antibody; and isolating the anti-PD-L1 antibody.

Aspects of the invention include methods of inhibiting one or more functions of a PD-1 protein, the methods comprising contacting the PD-L1 protein with an antibody as described herein. In some embodiments, a method is carried out in vitro. In some embodiments, a method is carried out in vivo in a mammalian subject.

Aspects of the invention include a method of inhibiting the growth of a tumor cell that expresses PD-L1, the method comprising administering an antibody as described herein to a subject having the tumor cell, thereby (i) inhibiting growth or proliferation of the tumor cell, or (ii) inducing death of the tumor cell.

Aspects of the invention include a pharmaceutical composition comprising an antibody as described herein and a pharmaceutically-acceptable carrier.

Aspects of the invention include a method of treating a subject having cancer, the method comprising administering an effective amount of a pharmaceutical composition as described herein to the subject. Aspects of the invention include use of an antibody as described herein in the preparation of a medicament for treating cancer. In some embodiments, the cancer is a hematologic cancer or an epithelial cancer. In some embodiments, the hematologic cancer is a leukemia, lymphoma, myeloma, or myelodysplastic syndrome. In some embodiments, the leukemia is an acute myeloid leukemia, acute lymphoblastic leukemia, chronic myelogenous leukemia, or chronic lymphocytic leukemia. In some embodiments, the lymphoma is Hodgkin's lymphoma or non-Hodgkin's lymphoma. In some embodiments, the epithelial cancer is non-small-cell lung, urinary bladder, renal, liver, colorectal, ovarian, gastric, esophageal, pancreatic, thyroid, breast, or nasopharyngeal cancer. In some embodiments, the breast cancer is hormone receptor negative or triple negative breast cancer. In some embodiments, the cancer is melanoma. In some embodiments, the cancer is glioblastoma.

In some embodiments, a pharmaceutical composition or medicament further comprises an effective amount of a second therapeutic agent.

Aspects of the invention include methods of screening a sample to determine the presence of a PD-L1 polypeptide in the sample, the methods comprising: contacting the sample with an anti-PD-L1 antibody described herein; and determining whether the anti-PD-L1 antibody binds to a PD-L1 polypeptide in the sample, wherein the presence of such binding is indicative of the presence of the PD-L1 polypeptide in the sample. In some embodiments, an anti-PD-L1 antibody is detectably labeled, and determining whether the anti-PD-L1 antibody binds to the PD-L1 polypeptide comprises detecting the detectable label.

DETAILED DESCRIPTION OF THE INVENTION

General Techniques

Figure 1:
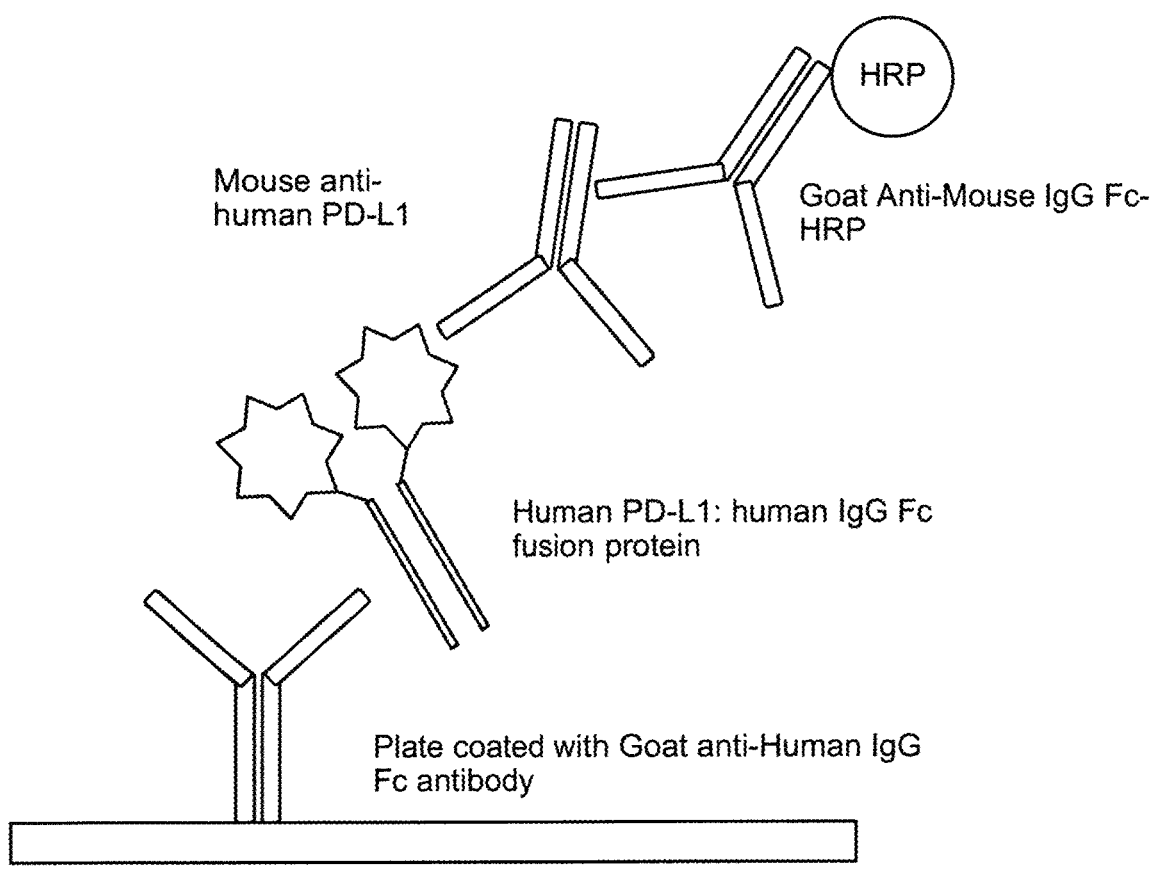
FIG. 1 is a schematic representation of an indirect ELISA assay.

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Monoclonal Antibodies: Principles and Practice" (Goding, Academic Press, 3$^{rd}$ Edition, 1996); "Antibody Engineering" (R. E. Kontermann & S. Dubel, 2013); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001).

One skilled in the art will recognize many methods and materials similar or equivalent to those described herein, which could be used in the practice of the present invention. Indeed, the present invention is in no way limited to the methods and materials described. For purposes of the present invention, the following terms are defined below.

Definitions

For purposes of interpreting this specification, the following definitions will apply and whenever appropriate, terms used in the singular will also include the plural and vice versa. In the event that any definition set forth conflicts with any document incorporated herein by reference, the definition set forth below shall control.

The terms "PD-L1" and "programmed cell death protein 1 ligand 1", as used interchangeably herein, refer to any PD-L1 from any vertebrate source, including mammals such as primates (e.g., humans) and rodents (e.g., mice and rats), unless otherwise indicated. "Human PD-L1" specifically includes the 290 amino acids long PD-L1 human polypeptide of SEQ ID NO: 48 (UniProtKB—Q9NZQ7).

The term "PD-L1" encompasses "full-length," unprocessed PD-L1 as well as any form of PD-L1 that results from processing within a cell. The term also encompasses naturally occurring variants of PD-L1, e.g., splice variants, allelic variants and isoforms. The PD-L1 polypeptides described herein may be isolated from any of a variety of sources, such as from human tissue types or from another source, or prepared by recombinant or synthetic methods. A "native sequence PD-L1 polypeptide" comprises a polypeptide having the same amino acid sequence as the corresponding PD-L1 polypeptide derived from nature. Such native sequence PD-L1 polypeptides can be isolated from nature or can be produced by recombinant or synthetic means. The term "native sequence PD-L1 polypeptide" specifically encompasses naturally-occurring truncated or secreted forms of PD-L1 (e.g., an extracellular domain sequence), naturally-occurring variant forms (e.g., alternatively spliced forms) and naturally-occurring allelic variants of the polypeptide. In certain embodiments of the invention, the native sequence PD-L1 polypeptides disclosed herein are mature or full-length native sequence polypeptides comprising full-length amino acid sequences of PD-L1. The term "PD-L1" specifically encompasses native human PD-L1 polypeptides, including, without limitation, the human PD-L1 polypeptide of SEQ ID NO: 48, with or without the N-terminal signal peptide at amino acids 1 to 18.

The terms "PD-1" and "programmed cell death protein 1", as used interchangeably herein, refer to any PD-1 from any vertebrate source, including mammals such as primates (e.g., humans) and rodents (e.g., mice and rats), unless otherwise indicated. "Human PD-1" specifically includes the 288 amino acids long PD-1 human polypeptide provided in UniProtKB—Q15116.

The term "PD-1" encompasses "full-length," unprocessed PD-1 as well as any form of PD-1 that results from processing within a cell. The term also encompasses naturally occurring variants of PD-1, e.g., splice variants, allelic variants and isoforms. The PD-1 polypeptides described herein may be isolated from any of a variety of sources, such as from human tissue types or from another source, or prepared by recombinant or synthetic methods. A "native sequence PD-1 polypeptide" comprises a polypeptide having the same amino acid sequence as the corresponding PD-1 polypeptide derived from nature. Such native sequence PD-1 polypeptides can be isolated from nature or can be produced by recombinant or synthetic means. The term "native sequence PD-1 polypeptide" specifically encompasses naturally-occurring truncated or secreted forms of PD-1 (e.g., an extracellular domain sequence), naturally-occurring variant forms (e.g., alternatively spliced forms) and naturally-occurring allelic variants of the polypeptide. In certain embodiments of the invention, the native sequence PD-1 polypeptides disclosed herein are mature or full-length native sequence polypeptides comprising full-length amino acid sequences of PD-1. The term "PD-1" specifically encompasses native human PD-1 polypeptides, including, without limitation, the human PD-1 polypeptide of UniProtKB-Q15116, with or without an N-terminal signal peptide.

An "epitope" is the site on the surface of an antigen molecule to which a single antibody molecule binds. Generally an antigen has several or many different epitopes and reacts with many different antibodies. The term specifically includes linear epitopes and conformational epitopes.

"Epitope mapping" is the process of identifying the binding sites, or epitopes, of antibodies on their target antigens. Antibody epitopes may be linear epitopes or conformational epitopes. Linear epitopes are formed by a continuous sequence of amino acids in a protein. Conformational epitopes are formed of amino acids that are discontinuous in the protein sequence, but which are brought together upon folding of the protein into its three-dimensional structure.

"Epitope binning", as defined herein, is the process of grouping antibodies based on the epitopes they recognize. More particularly, epitope binning comprises methods and systems for discriminating the epitope recognition properties of different antibodies, combined with computational processes for clustering antibodies based on their epitope recognition properties and identifying antibodies having distinct binding specificities.

An antibody binds "essentially the same epitope" as a reference antibody when the two antibodies recognize identical or sterically overlapping epitopes. The most widely used and rapid methods for determining whether two epitopes bind to identical or sterically overlapping epitopes are competition assays, which can be configured in all number of different formats, using either labeled antigen or labeled antibody. Usually, the antigen is immobilized on a 96-well plate, and the ability of unlabeled antibodies to block the binding of labeled antibodies is measured using radioactive or enzyme labels. Preferably, such antibody binds essentially to the same PD-L1 epitope as that bound by an antibody comprising an HVR-H1 of GFSLTSYDIS (SEQ ID NO: 4); an HVR-H2 sequence. of VIWTGVGTN (SEQ ID NO: 5); and an HVR-H3 sequence of DPYYYGMDY (SEQ ID NO: 6). In one embodiment, such antibody will comprise an HVR-H1 sequence having at least about 99% sequence identity to the sequence of SEQ ID NO: 4, an HVR-H2 sequence having at least about 99% sequence identity to the sequence of SEQ ID NO: 5, and an HVR-H3 sequence having at least about 99% sequence identity to the sequence of SEQ ID NO: 6. In this context, "PD-L1" preferably is the human PD-L1 polypeptide of SEQ ID NO: 48, with or without its N-terminal signal peptide.

A "modification" of an amino acid residue/position, as used herein, refers to a change of a primary amino acid sequence as compared to a starting amino acid sequence, wherein the change results from a sequence alteration involving said amino acid residue/positions. For example, typical modifications include substitution of the residue (or at said position) with another amino acid (e.g., a conservative or non-conservative substitution), insertion of one or more (generally fewer than 5 or 3) amino acids adjacent to said residue/position, and deletion of said residue/position. An "amino acid substitution" or variation thereof, refers to the replacement of an existing amino acid residue in a predetermined (starting) amino acid sequence with a different amino acid residue. Generally and preferably, a modification results in an alteration in at least one physical or biochemical activity of the variant polypeptide compared to a polypeptide comprising the starting (or "wild type") amino acid sequence. For example, in the case of an antibody, a physical or biochemical activity that is altered can be binding affinity, binding capability and/or binding effect upon a target molecule.

The term "antibody" includes monoclonal antibodies (including full length antibodies which have an immunoglobulin Fc region), single-chain molecules, as well as antibody fragments (e.g., Fab, F(ab')$_2$, and Fv). The term "immunoglobulin" (Ig) is used interchangeably with "antibody" herein. The basic 4-chain antibody unit is a heterotetrameric glycoprotein composed of two identical light (L) chains and two identical heavy (H) chains. Unless noted otherwise, the term "antibody" is used herein in the broadest sense and specifically includes all isotypes, sub-classes and forms of antibodies, including IgG, IgM, IgA, IgD, and IgE antibodies and their fragments, preferably antigen-binding fragments. Preferred antibodies herein include IgG, IgM and IgA antibodies and antigen-binding fragments thereof. In some embodiments, an antibody of a first isotype, such as IgM, can be modified to include sequences from another isotype, such as IgG, to produce hybrid antibodies, non-limiting examples of which include IgG/IgM and IgG/IgA hybrid antibodies.

Unless stated otherwise, the term "antibody" specifically includes native human and non-human IgG1, IgG2 (IgG2a, IgG2b), IgG3, IgG4, IgE, IgA, IgD and IgM antibodies, including naturally occurring variants. Thus, for example, the human IgM sequence is available under GenBank Accession Number X14940.1, while variants have been reported as GenBank CAB37838.1, CAC20458.1, AFM37312.1, X57331.1, and J00260.1.

The term "native" with reference to a polypeptide (e.g., an antibody or a J-chain) is used herein to refer to a polypeptide having a sequence that occurs in nature, regardless of its mode of preparation. Thus, the terms "native" and "native sequence" are used herein interchangeably, and expressly encompass recombinant polypeptides with a sequence that is found in nature.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) Nature 256:495, or may be made by recombinant DNA methods (see, e.g., U.S. Pat. No. 4,816,567). The "monoclonal antibodies" may also be isolated from phage antibody libraries using the techniques described in Clackson et al. (1991) Nature 352:624-628 and Marks et al. (1991) J. Mol. Biol. 222:581-597, for example.

The monoclonal antibodies herein specifically include "chimeric" antibodies (immunoglobulins) in which a portion of the heavy and/or light chain is identical with or homologous to corresponding sequences in antibodies derived from a particular species, while the remainder of the chain(s) is identical with or homologous to corresponding sequences in antibodies derived from another species, as well as fragments of such antibodies, so long as they exhibit the desired biological activity (U.S. Pat. No. 4,816,567; and Morrison et al. (1984) Proc. Natl. Acad. Sci. USA 81:6851-6855).

"Humanized" forms of non-human (e.g., murine) antibodies are antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are also replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al. (1986) *Nature* 321:522-525; Riechmann et al. (1988) *Nature* 332:323-329; and Presta (1992) *Curr. Op. Struct. Biol.* 2:593-596.

An "isolated" antibody herein is one which has been identified and separated and/or recovered from a component of its natural environment in a recombinant host cell. Contaminant components of its natural environment are materials which would interfere with diagnostic or therapeutic uses for the antibody, and may include enzymes, hormones, and other proteinaceous or non-proteinaceous solutes, as well as undesired byproducts of the production. In a preferred embodiment, an isolated antibody herein will be purified (1) to greater than 95% by weight, or greater than 98% by weight, or greater than 99% by weight, as determined by SDS-PAGE or SEC-HPLC methods, (2) to a degree sufficient to obtain at least 15 residues of N-terminal or internal amino acid sequence by use of an amino acid sequencer, or (3) to homogeneity by SDS-PAGE under reducing or non-reducing conditions using Coomassie blue or, preferably, silver stain. Ordinarily, an isolated antibody will be prepared by at least one purification step.

In the case of IgGs, the 4-chain unit is generally about 150,000 Daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain at its other end. The $V_L$ is aligned with the $V_H$ and the $C_L$ is aligned with the first constant domain of the heavy chain ($C_{H1}$). Particular amino acid residues are believed to form an interface between the light chain and heavy chain variable domains. The pairing of a $V_H$ and $V_L$ together forms a single antigen-binding site.

IgM is a glycoprotein which forms polymers where multiple immunoglobulins are covalently linked together with disulfide bonds. IgM mostly exists as a pentamer but also as a hexamer and therefore contains 10 or 12 antigen binding sites. The pentameric form typically contains an additional polypeptide, called the J-chain, but can also be made in the absence of J-chain. The pentameric IgM molecule has a molecular weight of approximately 970 kDa. Due to its polymeric nature, IgM possesses high avidity and is particularly effective in complement activation. Unlike in IgG, the heavy chain in IgM monomers is composed of one variable and four constant domains. The IgM constant domains are designated herein as CM1 or Cμ1, CM2 or Cμ2, CM3 or Cμ3, and CM4 or Cμ4, wherein the "CM" and "Cμ." designations are used interchangeably.

The term "IgM" is used herein in the broadest sense and specifically includes mono-, and multi-specific (including bispecific) IgM molecules, such as, for example, the multi-specific IgM binding molecules disclosed in PCT Application No. PCT/US2014/054079, the entire disclosure of which is expressly incorporated by reference herein.

The term "IgM binding unit" or "IgM antibody binding unit" is used in the broadest sense and specifically covers an IgM antibody heavy chain constant region polypeptide, comprising at least a Cμ4 constant domain, fused to a variable domain sequence ($V_H$) binding to a target (e.g., antigen), with or without an associated antibody light chain variable domain ($V_L$) sequence.

The term "bispecific IgM binding unit" or "bispecific IgM antibody binding unit" is used in the broadest sense and specifically covers a pair of IgM antibody heavy chain constant region polypeptides, comprising at least a Cμ4 constant domain, fused to a variable domain sequence ($V_H$), each variable domain sequence binding to a different target, with or without associated antibody light chain variable domain ($V_L$) sequences. In one embodiment, the bispecific IgM antibody comprises two $V_H V_L$ antigen binding regions, each capable of binding to a different epitope on one antigen or epitopes on two different antigens. The bispecific IgM antibody binding units can be full length from a single species, or can be chimerized or humanized. Bispecific IgM antibodies of the present invention can have a penta- or hexameric ring structure comprising five or six bispecific IgM binding units.

The term "multi-specific IgM" is used herein in the broadest sense to refer to IgM antibodies with two or more binding specificities. Thus, the term "multi-specific" includes "bispecific", e.g., bispecific antibodies or bispecific binding units, including IgM pentamers comprising at least two monospecific subunits, each binding to a different antigen (AA, BB), or five or six bispecific subunits, each binding to two different antigens (AB, AB). Thus, the bispecific and multi-specific IgM pentamers may include five identical bispecific binding units, monospecific IgM binding units, at least two of them have different binding specificities, or any combination thereof.

A "full length IgM antibody heavy chain" is a polypeptide consisting in N-terminal to C-terminal direction of an antibody heavy chain variable domain (VH), an antibody constant heavy chain constant domain 1 (CM1 or Cμ1), an antibody heavy chain constant domain 2 (CM2 or Cμ2), an antibody heavy chain constant domain 3 (CM3 or Cμ3), and an antibody heavy chain constant domain 4 (CM4 or Cμ4). The bispecific full length IgM antibodies as defined herein comprise five or six monomers (binding units), each with two antigen binding sites, which specifically bind to two different binding targets (epitopes). The C-terminus of the heavy or light chain of the full length antibody denotes the last amino acid at the C-terminus of the heavy or light chain. The N-terminus of the heavy or light chain of the full length antibody denotes the first amino acid at the N-terminus of the heavy or light chain.

Native IgA is a tetrameric protein comprising two identical light chains (κ or μ) and two identical heavy chains (α). In the human, there are two IgA isotypes, IgA1 and IgA2. IgA, similarly to IgG, contains three constant domains (CA1-CA3 or Cα1-Cα3), with a hinge region between the Cα1 and Cα2 domains, wherein the "CA" and "Cα" designations are used interchangeably. All IgA isotypes have an 18 amino acid "tailpiece", which is located C-terminal to the Cα3 domain, which enables polymeric Ig formation (see, e.g., Garcia-Pardo et al., 1981, *J Biol. Chem.* 256, 11734-11738 and Davis et al., 1988, *Eur. J Immunol.* 18, 1001-1008). Serum IgA is a monomer but can also polymerize. In its secretory form IgA comprises from 2-5 of the basic 4-chain units, linked by a J-chain, which may include a tail-piece, and may be associated by a secretory component. IgA antibodies can be further divided into IgA1 and IgA2 sub-classes. The term "IgA" antibody is used herein to specifically include all sub-classes, i.e., IgA1 and IgA2 antibodies, including dimeric and multimeric forms, with and without a secretory component, as well as fragments, preferably antigen-binding fragments, of such antibodies. For the purposes of the present invention, an IgA antibody preferably is a dimer, where two tail-pieces are connected by a J-chain.

The term "IgA" is used herein in the broadest sense and specifically includes mono-, and multi-specific IgA molecules, such as, for example, the multi-specific IgA binding molecules disclosed in PCT Application No. PCT/US2015/015268, the entire disclosure of which is expressly incorporated by reference herein.

The term "multi-specific IgA" is used herein in the broadest sense to refer to IgA antibodies with two or more binding specificities. Thus, the term "multi-specific" includes "bispecific", e.g., bispecific antibodies or bispecific binding units, including IgA dimers comprising two monospecific subunits, each binding to a different antigen (AA, BB), or two bispecific subunits, each binding to two different antigens (AB, AB).

In one embodiment, a dimeric multi-specific IgA molecule consists of two monospecific binding units, each binding unit having binding specificity to a different binding target (AA, BB). In another embodiment, in a dimeric IgA molecule at least one of the two binding units has two different binding specificities (i.e., is a bispecific, e.g., AA, AB or AA, BC). In another embodiment, each of the two binding units has two specificities, which may be the same (AB, AB) or different (AC, CD or AB, AC, for example).

The term "bispecific IgA antibody binding unit" is used in the broadest sense and specifically covers a pair of IgA antibody heavy chain constant region polypeptides, comprising at least a CA3 constant domain, fused to a variable domain sequence ($V_H$), each variable domain sequence binding to a different target, with or without associated antibody light chain variable domain ($V_L$) sequences. In one embodiment, the bispecific IgA antibody comprises two $V_H V_L$ antigen binding regions, each capable of binding to a different epitope on one antigen or epitopes on two different antigens. A bispecific IgA antibody binding unit can be full length from a single species, or can be chimerized or humanized.

A "full length IgA antibody heavy chain" is a polypeptide consisting in N-terminal to C-terminal direction of an antibody heavy chain variable domain (VH), an antibody constant heavy chain constant domain 1 (CA1 or Cα1), an antibody constant heavy chain constant domain 2 (CA2 or Cα2), and an antibody heavy chain constant domain 3 (CA3 or Cα3). A bi- or multi-specific full length IgA antibody according to the invention can comprise two monomers (binding units), each of which may be mono- or bispecific, with or without a secretory component. Thus, the multi-specific IgA antibodies of the present invention may include monospecific and bispecific binding units, provided that the resultant IgA antibody has at least two binding specificities. The C-terminus of the heavy or light chain of the full length antibody denotes the last amino acid at the C-terminus of the heavy or light chain. The N-terminus of the heavy or light chain of the full length antibody denotes the first amino acid at the N-terminus of the heavy or light chain.

For further details of the structure and properties of the different classes of antibodies, see e.g., Basic and Clinical Immunology, 8th Edition, Daniel P. Stites, Abba I. Ten and Tristram G. Parslow (eds), Appleton & Lange, Norwalk, Conn., 1994, page 71 and Chapter 6.

The term "interface", as used herein, is used to refer to a region, which comprises those "contact" amino acid residues (or other non-amino acid groups such as, for example, carbohydrate groups,) in a first antibody heavy chain constant region which interact with one or more "contact" amino acid residues (or other non-amino acid groups) in a second antibody heavy chain constant region.

The term "asymmetric interface" is used to refer to an interface (as hereinabove defined) formed between two antibody chains, such as a first and a second IgM heavy chain constant region and/or between an IgM heavy chain constant region and its matching light chain, wherein the contact residues in the first and the second chains are different by design, comprising complementary contact residues. The asymmetric interface can be created by knobs/holes interactions and/or salt bridge coupling (charge swaps) and/or other techniques known in the art, such as for example, by the CrossMab approach for coupling a μ heavy chain to its matching light chain.

A "cavity" or "hole" refers to at least one amino acid side chain which is recessed from the interface of the second polypeptide and therefore accommodates a corresponding protuberance ("knob") on the adjacent interface of the first polypeptide. The cavity (hole) may exist in the original interface or may be introduced synthetically (e.g., by altering a nucleic acid encoding the interface). Normally, a nucleic acid encoding the interface of the second polypeptide is altered to encode the cavity. To achieve this, the nucleic acid encoding at least one "original" amino acid residue in the interface of the second polypeptide is replaced with DNA encoding at least one "import" amino acid residue which has a smaller side chain volume than the original amino acid residue. It will be appreciated that there can be more than one original and corresponding import residue. The upper limit for the number of original residues which are replaced is the total number of residues in the interface of the second polypeptide. The preferred import residues for the formation of a cavity are usually naturally occurring amino acid residues and are preferably selected from alanine (A), serine (S), threonine (T), valine (V) and glycine (G). Most preferred amino acid residues are serine, alanine or threonine, most preferably alanine. In the preferred embodiment, the original residue for the formation of the protuberance has a large side chain volume, such as tyrosine (Y), arginine (R), phenylalanine (F) or tryptophan (W).

An "original" amino acid residue is one which is replaced by an "import" residue which can have a smaller or larger side chain volume than the original residue. The import amino acid residue can be a naturally occurring or non-naturally occurring amino acid residue, but preferably is the former.

By "non-naturally occurring" amino acid residue is meant a residue which is not encoded by the genetic code, but which is able to covalently bind adjacent amino acid residue(s) in the polypeptide chain. Examples of non-naturally occurring amino acid residues are norleucine, ornithine, norvaline, homoserine and other amino acid residue analogues such as those described in Ellman et al., Meth. Enzym. 202:301-336 (1991), for example. To generate such non-naturally occurring amino acid residues, the procedures of Noren et al. Science 244: 182 (1989) and Ellman et al., supra can be used. Briefly, this involves chemically activating a suppressor tRNA with a non-naturally occurring amino acid residue followed by in vitro transcription and translation of the RNA. The methods of the current invention, in certain embodiments, involve replacing at least one original amino acid residue in an IgM heavy chain, but more than one original residue can be replaced. Normally, no more than the total residues in the interface of the first or second polypeptide will comprise original amino acid residues which are replaced. The preferred original residues for replacement are "buried". By "buried" is meant that the residue is essentially inaccessible to solvent. The preferred import residue is not cysteine to prevent possible oxidation or mispairing of disulfide bonds.

The protuberance is "positionable" in the cavity which means that the spatial location of the protuberance and cavity on the interface of the first polypeptide and second polypeptide respectively and the sizes of the protuberance and cavity are such that the protuberance can be located in the cavity without significantly perturbing the normal association of the first and second polypeptides at the interface. Since protuberances such as Tyr, Phe and Trp do not typically extend perpendicularly from the axis of the interface and have preferred conformations, the alignment of a protuberance with a corresponding cavity relies on modeling the protuberance/cavity pair based upon a three-dimensional structure such as that obtained by X-ray crystallography or nuclear magnetic resonance (NMR). This can be achieved using widely accepted techniques in the art, including techniques of molecular modeling.

By "original nucleic acid" is meant the nucleic acid encoding a polypeptide of interest which can be "altered" (i.e., genetically engineered or mutated) to encode a protuberance or cavity. The original or starting nucleic acid may be a naturally occurring nucleic acid or may comprise a nucleic acid which has been subjected to prior alteration (e.g., a humanized antibody fragment). By "altering" the nucleic acid is meant that the original nucleic acid is mutated by inserting, deleting or replacing at least one codon encoding an amino acid residue of interest. Normally, a codon encoding an original residue is replaced by a codon encoding an import residue. Techniques for genetically modifying a DNA in this manner have been reviewed in Mutagenesis: a Practical Approach, M. J. McPherson, Ed., (IRL Press, Oxford, UK. (1991), and include site-directed mutagenesis, cassette mutagenesis and polymerase chain reaction (PCR) mutagenesis, for example.

The protuberance or cavity can be "introduced" into the interface of the first or second polypeptide by synthetic means, e.g., by recombinant techniques, in vitro peptide synthesis, those techniques for introducing non-naturally occurring amino acid residues previously described, by enzymatic or chemical coupling of peptides or some combination of these techniques. According, the protuberance or cavity which is "introduced" is "non-naturally occurring" or "non-native", which means that it does not exist in nature or in the original polypeptide (e.g., a humanized monoclonal antibody).

Preferably the import amino acid residue for forming the protuberance has a relatively small number of "rotamers" (e.g., about 3-6). A "rotamer" is an energetically favorable conformation of an amino acid side chain. The number of rotamers for the various amino acid residues are reviewed in Ponders and Richards, J. Mol. Biol. 193: 775-791 (1987).

The term "native sequence J-chain" or "native J-chain" as used herein refers to J-chain of native sequence IgM or IgA antibodies of any animal species, including mature human J-chain, the amino acid sequence of which is shown in SEQ ID NO: 47.

The term "modified J-chain" is used herein to refer to variants of native sequence J-chain polypeptides comprising an extraneous binding moiety introduced into the native sequence. The introduction can be achieved by any means, including direct or indirect fusion of an extraneous binding moiety or by attachment through a chemical linker. The term "modified human J-chain" specifically encompasses, without limitation, a native sequence human J-chain of the amino acid sequence of SEQ ID NO: 47 modified by the introduction of a binding moiety. The term specifically encompasses, without limitation, a native sequence human J-chain of the amino acid sequence of SEQ ID NO: 47 modified by the introduction of an extraneous binding moiety which does not interfere with efficient polymerization (dimerization) of IgM or IgA and binding of such polymers (dimers) to a target.

The term "binding moiety" is used herein in the broadest sense to encompass any chemical entity capable of specific binding to a target, such as an antigen. Examples of binding moieties include, without limitation, antibodies, antigen-binding fragments of antibodies, antibody-drug conjugates, antibody-like molecules, antigen-binding fragments of antibody-like molecules, ligands and receptors. Preferred binding moieties are polypeptides (including peptides), preferably with a biological function. An example of a biological function is the ability of a binding moiety to bind to and activate or block the activity of a signaling pathway.

The term "polypeptide" is used herein in the broadest sense and includes peptide sequences. The term "peptide" generally describes linear molecular chains of amino acids containing up to about 60, preferably up to about 30 amino acids covalently linked by peptide bonds.

The term "extraneous" with reference to a "binding moiety" is used herein to refer to a binding moiety not present in a reference native polypeptide sequence at the same location. Thus, an extraneous polypeptide sequence (including peptide sequences), might be comprised within the corresponding native sequence but at a different location. In a preferred embodiment, the "extraneous" sequence is not present in the corresponding native sequence in any location.

The term "specific binding" or "specifically binds to" or is "specific for" refers to the binding of a binding moiety to a binding target, such as the binding of an antibody to a target antigen, e.g., an epitope on a particular polypeptide, peptide, or other target (e.g., a glycoprotein target), and means binding that is measurably different from a non-specific interaction (e.g., a non-specific interaction may be binding to bovine serum albumin or casein). Specific binding can be measured, for example, by determining binding of a binding moiety, or an antibody, or an antibody modified by introduction of a binding moiety, to a target molecule compared to binding to a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about 200 nM, alternatively at least about 150 nM, alternatively at least about 100 nM, alternatively at least about 60 nM, alternatively at least about 50 nM, alternatively at least about 40 nM, alternatively at least about 30 nM, alternatively at least about 20 nM, alternatively at least about 10 nM, alternatively at least about 8 nM, alternatively at least about 6 nM, alternatively at least about 4 nM, alternatively at least about 2 nM, alternatively at least about 1 nM, or greater. In certain instances, the term "specific binding" refers to binding where a molecule binds to a particular polypeptide or epitope on a particular polypeptide without substantially binding to any other polypeptide or polypeptide epitope.

"Binding affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). For example, the Kd can be about 200 nM, 150 nM, 100 nM, 60 nM, 50 nM, 40 nM, 30 nM, 20 nM, 10 nM, 8 nM, 6 nM, 4 nM, 2 nM, 1 nM, or stronger. Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art.

As used herein, the "Kd" or "Kd value" refers to a dissociation constant measured by a technique appropriate for the antibody and target pair, for example using surface plasmon resonance assays, for example, using a BIAcore™-2000 or a BIAcore™-3000 (BIAcore, Inc., Piscataway, N.J.) at 25° C. with immobilized antigen CMS chips at about 10 response units (RU).

The terms "conjugate," "conjugated," and "conjugation" refer to any and all forms of covalent or non-covalent linkage, and include, without limitation, direct genetic or chemical fusion, coupling through a linker or a cross-linking agent, and non-covalent association.

The term "fusion" is used herein to refer to the combination of amino acid sequences of different origin in one polypeptide chain by in-frame combination of their coding nucleotide sequences. The term "fusion" explicitly encompasses internal fusions, i.e., insertion of sequences of different origin within a polypeptide chain, in addition to fusion to one of its termini. The term "fusion" is used herein to refer to the combination of amino acid sequences of different origin The term "valent" as used herein denotes the presence of a specified number of binding sites in an antibody. As such, the terms "bivalent", "tetravalent", and "hexavalent" denote the presence of two binding sites, four binding sites, and six binding sites, respectively. Thus, if in a bispecific IgA antibody according to the present invention each binding unit is bivalent, the bispecific IgA antibody will have 4 valencies.

The term "epitope" includes any molecular determinant capable of specific binding to an antibody. In certain embodiments, an epitope determinant includes chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by an antibody. A "binding region" is a region on a binding target bound by a binding molecule.

"Polyepitopic specificity" refers to the ability to specifically bind to two or more different epitopes on the same or different target(s). "Monospecific" refers to the ability to bind only one epitope. In some embodiments, an antibody binds to each epitope with an affinity of at least $10^{-7}$ M, or $10^{-8}$ M or better.

The term "target" or "binding target" is used in the broadest sense and specifically includes polypeptides, without limitation, nucleic acids, carbohydrates, lipids, cells, and other molecules with or without biological function as they exist in nature.

The term "antigen" refers to an entity or fragment thereof, which can bind to an antibody or trigger a cellular immune response. An immunogen refers to an antigen, which can elicit an immune response in an organism, particularly an animal, more particularly a mammal including a human. The term antigen includes regions known as antigenic determinants or epitopes, as defined above.

As used herein, the term "immunogenic" refers to substances that elicit the production of antibodies, and/or activate T-cells and/or other reactive immune cells directed against an antigen of the immunogen.

An "antigen-binding site" or "antigen-binding region" of an antibody of the present invention typically contains six hypervariable regions (HVRs) which contribute in varying degrees to the affinity of the binding site for antigen. The term "complementarity determining region" or "CDR" is used interchangeably herein with the term "hypervariable region" or "HVR". There are three heavy chain variable domain HVRs (HVR-H1, HVR-H2 and HVR-H3) and three light chain variable domain HVRs (HVR-L1, HVR-L2 and HVR-L3). The extent of HVR and framework regions (FRs) is determined by comparison to a compiled database of amino acid sequences in which those regions have been defined according to variability among the sequences and/or structural information from antibody/antigen complexes. Also included within the scope of the invention are functional antigen binding sites comprised of fewer HVRs (i.e., where binding specificity is determined by three, four or five HVRs). Less than a complete set of 6 HVRs may be sufficient for binding to some binding targets. Thus, in some instances, the HVRs of a VH or a VL domain alone will be sufficient. Furthermore, certain antibodies might have non-HVR-associated binding sites for an antigen. Such binding sites are specifically included within the present definition.

The term "host cell" as used in the current application denotes any kind of cellular system which can be engineered to generate the antibodies according to the current invention. In one embodiment Chinese hamster ovary (CHO) cells are used as host cells.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included.

A nucleic acid is "operably linked" when it is placed in a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

The terms "anti-PD-L1 antibody", "PD-L1 antibody", or "an antibody that binds to PD-L1" all refer to an antibody that is capable of binding PD-L1 with sufficient affinity such that the antibody is useful as a diagnostic and/or therapeutic agent in targeting PD-L1. In certain embodiments, an anti-PD-L1 antibody binds to an epitope of PD-L1 that is conserved among PD-L1 from different species.

In one embodiment, a "PD-L1 antibody" is used herein to specifically refer to an anti-PD-L1 monoclonal antibody that (i) comprises a heavy chain variable domain sequence as provided in any one of SEQ ID NOS: 36-42 or 45, and/or a light chain variable domain sequence as provided in any one of SEQ ID NOS: 43, 44 or 46; or (ii) comprises one, two, three, four, five, or six of the HVRs provided in SEQ ID NOS: 1-6.

The term "variable" refers to the fact that certain segments of the variable domains differ extensively in sequence among antibodies. The "variable" or "V" domain mediates antigen binding and defines specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)).

An "intact" antibody is one which comprises an antigen-binding site as well as a light chain constant domain (CL) and at least heavy chain constant domains of the particular antibody class. For example, an intact IgG antibody comprises an antigen-binding site, a light chain constant domain CL, and at least heavy chain constant domains CH1 (Cγ1), CH2 (Cγ2) and CH3 (Cγ3). An intact IgM antibody comprises an antigen-binding site, a light chain constant domain CL, and at least heavy chain constant domains CM1 (Cμ1), CM2 (Cμ2), CM3 (Cμ3) and CM4 (Cμ4). An intact IgA antibody comprises an antigen-binding site, a light chain constant domain CL, and at least heavy chain constant domains CA1 (Cα1), CA2 (Cα2) and CA3 (Cα3). An intact IgD antibody comprises an antigen-binding site, a light chain constant domain CL, and at least heavy chain constant domains CD1 (Cδ1), CD2 (Cδ2) and CD3 (Cδ3). An intact IgE antibody comprises an antigen-binding site, a light chain constant domain CL, and at least heavy chain constant domains CE1 (Cε1), CE2 (Cε2), CE3 (Cε3) and CE4 (Cε4). The constant domains can be native sequence constant domains (e.g., human native sequence constant domains) or amino acid sequence variants thereof. Preferably, an intact antibody has one or more effector functions.

"Antibody fragments" comprise a portion of an intact antibody, preferably the antigen binding or variable region of the intact antibody. Non-limiting examples of antibody fragments include Fab, Fab', F(ab')2, and Fv fragments; diabodies; linear antibodies (see U.S. Pat. No. 5,641,870, Example 2; Zapata et al., Protein Eng. 8(10): 1057-1062 (1995)); single-chain antibody molecules; and multispecific antibodies formed from antibody fragments. In one embodiment, an antibody fragment comprises an antigen binding site of an intact antibody and thus retains the ability to bind antigen. Those of ordinary skill in the art will understand that an antibody fragment can be generated from any intact antibody, e.g., from an IgG, IgM, IgA, IgD, or IgE antibody, by separating at least an antigen-binding portion of the antibody from the remainder of its light and heavy chains to create an antigen-binding fragment. In certain embodiments, an antibody fragment can comprise an antigen-binding region of an antibody, as well as one or more additional domains of a light and/or heavy chain of the antibody. For example, in some embodiments, an antibody fragment can comprise an antigen-binding region comprising a VH and a VL domain, a light chain constant domain CL, and one or more heavy chain constant domains, e.g., a CH1 (Cγ1) domain, a CM1 (Cμ1) domain, a CA1 (Cα1) domain, a CD1 (Cδ1) domain, or a CE1 (Cε1) domain.

In the case of IgG antibody fragments, papain digestion produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CH1). Each Fab fragment is monovalent with respect to antigen binding, i.e., it has a single antigen-binding site. Pepsin treatment of an IgG antibody yields a single large F(ab')2 fragment which roughly corresponds to two disulfide linked Fab fragments having divalent antigen-binding activity and is still capable of cross-linking antigen. Fab' fragments differ from Fab fragments by having additional few residues at the carboxy terminus of the CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The Fc fragment of an IgG antibody comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and binding site. This fragment consists of a dimer of one heavy- and one light-chain variable region domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

The term "antagonist" as used herein refers to a molecule that causes a decrease in a function or activity as compared to the same function or activity in the absence of the molecule. An "antagonist" of a signaling pathway is therefore a molecule whose presence causes a decrease in a function or activity of the signaling pathway. The term "antagonize" as used herein refers to causing a decrease in a function or activity. A "blocking" antibody or an "antagonist" or "antagonistic" antibody is one which inhibits or reduces a biological activity of an antigen to which it binds. Preferred blocking antibodies or antagonist antibodies are capable of substantially or completely inhibiting a biological activity of an antigen.

An antibody "which binds" an antigen of interest, e.g., a PD-L1 epitope antigen target, is one that binds the antigen with sufficient affinity such that the antibody is useful as a therapeutic agent in targeting a cell or tissue expressing the antigen, and does not significantly cross-react with other proteins. With regard to the binding of an antibody to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. In one embodiment, the term "specific binding" refers to binding where a molecule binds to a particular polypeptide or epitope on a particular polypeptide without substantially binding to any other polypeptide or polypeptide epitope.

An antibody that "inhibits the growth of tumor cells expressing a PD-L1 epitope" or a "growth inhibitory" antibody is one which results in measurable growth inhibition of cancer cells expressing or overexpressing a PD-L1 epitope. The PD-L1 epitope may be a transmembrane polypeptide expressed on the surface of a cancer cell or may be a polypeptide that is produced and secreted by a cancer cell. Preferred growth inhibitory anti-PD-L1 antibodies inhibit growth of PD-L1-expressing tumor cells by greater than 20%, preferably from about 20% to about 50%, and even more preferably, by greater than 50% (e.g., from about 50% to about 100%) as compared to an appropriate control, the control typically being tumor cells not treated with the antibody being tested.

Antibodies that "inhibit the growth of tumor cells expressing a PD-L1 epitope" may also (i) inhibit the growth or proliferation of a cell to which they bind; (ii) induce the death of a cell to which they bind; or (iii) inhibit the metastasis of a cell to which they bind.

The term "agonist" as used herein refers to a molecule that causes an increase in a function or activity as compared to the same function or activity in the absence of the molecule. An "agonist" of a signaling pathway is therefore a molecule whose presence causes an increase in a function or activity of the signaling pathway. The term "agonize" as used herein refers to causing an increase in a function or activity.

The term "T-cell inhibitory signaling pathway" as used herein refers to a T-cell signaling pathway that leads to a qualitative or quantitative decrease in, blocking of, or halting of a T-cell immune response.

The term "T-cell stimulatory signaling pathway" as used herein refers to a T-cell signaling pathway that leads to a qualitative or quantitative increase in or maintenance of a T-cell immune response.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), skin cancer, melanoma, lung cancer, including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer (e.g., pancreatic ductal adenocarcinoma), glioblastoma, cervical cancer, ovarian cancer (e.g., high grade serous ovarian carcinoma), liver cancer (e.g., hepatocellular carcinoma (HCC)), bladder cancer (e.g., urothelial bladder cancer), testicular (germ cell tumor) cancer, hepatoma, breast cancer, brain cancer (e.g., astrocytoma), colon cancer, rectal cancer, colorectal cancer, endometrial or uterine carcinoma, salivary gland carcinoma, kidney or renal cancer (e.g., renal cell carcinoma, nephroblastoma or Wilms' tumour), prostate cancer, vulval cancer, thyroid cancer, hepatic carcinoma, anal carcinoma, penile carcinoma, as well as head and neck cancer. Additional examples of cancer include, without limitation, retinoblastoma, thecomas, arrhenoblastomas, hepatoma, hematologic malignancies including non-Hodgkin's lymphoma (NHL), multiple myeloma and acute hematologic malignancies, endometrial or uterine carcinoma, endometriosis, fibrosarcomas, choriocarcinoma, salivary gland carcinoma, vulval cancer, thyroid cancer, esophageal carcinomas, hepatic carcinoma, anal carcinoma, penile carcinoma, nasopharyngeal carcinoma, laryngeal carcinomas, Kaposi's sarcoma, melanoma, skin carcinomas, Schwannoma, oligodendroglioma, neuroblastomas, rhabdomyosarcoma, osteogenic sarcoma, leiomyosarcomas, and urinary tract carcinomas.

The term "metastatic cancer" means the state of cancer where the cancer cells of a tissue of origin are transmitted from the original site to one or more sites elsewhere in the body, by the blood vessels or lymphatics, to form one or more secondary tumors in one or more organs besides the tissue of origin. A prominent example is metastatic breast cancer.

As used herein, a "PD-L1-associated cancer" is a cancer that is associated with expression or over-expression of a PD-L1 gene or gene product, which can be any cancer that is characterized by cells that express normal or elevated levels of one or more PD-L1 gene products, relative to suitable control cells. Suitable control cells can be cells from an individual who is not affected with a PD-L1 expressing or over-expressing cancer, or they may be non-cancerous cells from either the subject in need, or they may be non-cancerous cells from another individual who is affected with a PD-L1 expressing or over-expressing cancer.

The terms "cell proliferative disorder" and "proliferative disorder" refer to disorders that are associated with some degree of abnormal cell proliferation. In one embodiment, the cell proliferative disorder is cancer.

"Tumor", as used herein, refers to all neoplastic cell growth and proliferation, whether malignant or benign, and all pre-cancerous and cancerous cells and tissues.

The terms "predictive" and "prognostic" as used herein are also interchangeable, in the sense of meaning that the methods for prediction or prognostication are to allow the person practicing the method to select patients that are deemed (usually in advance of treatment, but not necessarily) more likely to respond to treatment with an anti-cancer agent, including an anti-PD-L1 antibody.

The terms "treat", "treatment" or "treating" as used herein refer to both therapeutic treatment and prophylactic of preventative measures, wherein the object is to prevent or slow down (lessen) a targeted pathological condition or disorder. A subject in need of treatment includes those already having a particular condition or disorder, as well as those prone to having the disorder or those in whom the disorder is to be prevented.

Anti-PD-L1 Compositions

Aspects of the invention include anti-PD-L1 antibodies, or antigen-binding fragments thereof, specifically including, without limitation, IgM, IgG, and IgA antibodies. In one aspect, the invention provides an antibody which binds, preferably specifically, to a PD-L1 polypeptide, as described herein. In some embodiments, an antibody is a monoclonal antibody, or an antigen-binding fragment thereof, including, e.g., Fab, Fab', F(ab')2, and Fv fragments, diabody, and single domain antibody. In some embodiments, an antibody is a chimeric antibody, a humanized antibody, a single-chain antibody or an antibody that competitively inhibits the binding of an anti-PD-L1 antibody to its respective antigenic epitope. The antibodies of the present invention may optionally be produced in CHO cells or bacterial cells and are capable of inhibiting an interaction between a PD-L1 protein and a receptor or ligand to which it binds. In some embodiments, an anti-PD-L1 antibody is capable of inducing death of a cell to which it binds. For detection purposes, the antibodies of the present invention may be detectably labeled, attached to a solid support, or the like.

In one aspect, an anti-PD-L1 antibody is provided, wherein the antibody has one or more of the following activities: (i) inhibits interaction between a PD-L1 protein and a receptor or ligand (e.g., a PD-1 protein) to which the PD-L1 protein is capable of binding; (ii) inhibits tumor metastasis in vivo; (iii) inhibits tumor growth in vivo; (iv) decreases tumor size in vivo; (v) exhibits cytotoxic activity on a tumor cell expressing PD-L1 in vivo; or (vi) exhibits cytostatic activity on a tumor cell expressing PD-L1 in vivo. In certain aspects, an anti-PD-L1 antibody is an antagonistic antibody that inhibits interaction between PD-L1 and PD-1. In certain aspects, an anti-PD-L1 antibody is capable of binding to a PD-L1 protein and thereby inhibiting one or more functions (e.g., one or more immunosuppressive functions) of a PD-1 protein.

In one aspect, an antibody that binds to PD-L1 is provided, wherein the antibody comprises one or more heavy chain HVR sequences having at least about 99% sequence identity to the sequences provided in SEQ ID NOS: 4, 5 and 6. In some embodiments, an antibody comprises all three of the heavy chain HVR sequences provided in SEQ ID NOS: 4, 5 and 6. In some embodiments, an antibody further comprises one or more light chain HVR sequences having at least about 99% sequence identity to the sequences provided in SEQ ID NOS: 1, 2 and 3. In some embodiments, an antibody comprises all three of the light chain HVR sequences provided in SEQ ID NOS: 1, 2 and 3. In certain embodiments, an antibody comprises a heavy chain variable domain sequence that comprises all three of the heavy chain HVR sequences provided in SEQ ID NOS: 4, 5 and 6, and comprises a light chain variable domain that comprises all three of the light chain HVR sequences that are provided in SEQ ID NOS: 1, 2 and 3.

Aspects of the invention include anti-PD-L1 antibodies whose heavy chain and light chain sequences comprise a framework sequence. Framework sequences in accordance with embodiments of invention include, for example, human protein and DNA germline sequences, as well as consensus framework sequences that are derived from any number of human protein and/or DNA germline sequences. In some embodiments, an anti-PD-L1 antibody light chain sequence comprises a human framework sequence or a human consensus framework sequence. In some embodiments, an anti-PD-L1 antibody heavy chain sequence comprises a human framework sequence or a human consensus framework sequence.

In some embodiments, an anti-PD-L1 antibody comprises a heavy chain framework region 1 (FR1) sequence that is at least about 80% identical, such as about 85%, about 90%, about 95%, or about 99% identical to any one of the heavy chain FR1 sequences provided in SEQ ID NOS: 7-11. In certain embodiments, an antibody comprises a heavy chain FR1 sequence as provided in any one of SEQ ID NOS: 7-11.

In some embodiments, an anti-PD-L1 antibody comprises a heavy chain framework region 2 (FR2) sequence that is at least about 80% identical, such as about 85%, about 90%, about 95%, or about 99% identical to any one of the heavy chain FR2 sequences provided in SEQ ID NOS: 12-16. In certain embodiments, an antibody comprises a heavy chain FR2 sequence as provided in any one of SEQ ID NOS: 12-16.

In some embodiments, an anti-PD-L1 antibody comprises a heavy chain framework region 3 (FR3) sequence that is at least about 80% identical, such as about 85%, about 90%, about 95%, or about 99% identical to any one of the heavy chain FR3 sequences provided in SEQ ID NOS: 17-24. In certain embodiments, an antibody comprises a heavy chain FR3 sequence as provided in any one of SEQ ID NOS: 17-24.

In some embodiments, an anti-PD-L1 antibody comprises a heavy chain framework region 4 (FR4) sequence that is at least about 80% identical, such as about 85%, about 90%, about 95%, or about 99% identical to any one of the heavy chain FR4 sequences provided in SEQ ID NOS: 25-26. In certain embodiments, an antibody comprises a heavy chain FR4 sequence as provided in any one of SEQ ID NOS: 25-26.

In some embodiments, an anti-PD-L1 antibody comprises a light chain framework region 1 (FR1) sequence that is at least about 80% identical, such as about 85%, about 90%, about 95%, or about 99% identical to any one of the light chain FR1 sequences provided in SEQ ID NOS: 27-29. In certain embodiments, an antibody comprises a light chain FR1 sequence as provided in any one of SEQ ID NOS: 27-29.

In some embodiments, an anti-PD-L1 antibody comprises a light chain framework region 2 (FR2) sequence that is at least about 80% identical, such as about 85%, about 90%, about 95%, or about 99% identical to any one of the light chain FR2 sequences provided in SEQ ID NOS: 30-31. In certain embodiments, an antibody comprises a light chain FR2 sequence as provided in any one of SEQ ID NOS: 30-31.

In some embodiments, an anti-PD-L1 antibody comprises a light chain framework region 3 (FR3) sequence that is at least about 80% identical, such as about 85%, about 90%, about 95%, or about 99% identical to any one of the light chain FR3 sequences provided in SEQ ID NOS: 32-33. In certain embodiments, an antibody comprises a light chain FR3 sequence as provided in any one of SEQ ID NOS: 32-33.

In some embodiments, an anti-PD-L1 antibody comprises a light chain framework region 4 (FR4) sequence that is at least about 80% identical, such as about 85%, about 90%, about 95%, or about 99% identical to any one of the light chain FR4 sequences provided in SEQ ID NOS: 34-35. In certain embodiments, an antibody comprises a light chain FR4 sequence as provided in any one of SEQ ID NOS: 34-35.

In one aspect, an antibody that binds to PD-L1 is provided, wherein the antibody comprises a heavy chain variable domain sequence that is at least about 80% identical, such as about 85%, about 90%, about 95%, or about 99% identical to any one of the heavy chain variable domain sequences provided in SEQ ID NOS: 36-42 or 45. In some embodiments, an antibody comprises a heavy chain variable domain sequence provided in any one of SEQ ID NOS: 36-42 or 45.

In some embodiments, an antibody comprises a light chain variable domain sequence that is at least about 80% identical, such as about 85%, about 90%, about 95%, or about 99% identical to any one of the light chain variable domain sequences provided in SEQ ID NOS: 43, 44 or 46. In some embodiments, an antibody comprises a heavy chain variable domain sequence provided in any one of SEQ ID NOS: 43, 44 or 46.

In some embodiments, an anti-PD-L1 antibody comprises a heavy chain variable domain sequence that is at least about 80% identical, such as about 85%, about 90%, about 95%, or about 99% identical to the heavy chain variable domain sequence provided in SEQ ID NO: 45, and comprises a light chain variable domain sequence that is at least about 80% identical, such as about 85%, about 90%, about 95%, or about 99% identical to the light chain variable domain sequence provided in SEQ ID NO: 46. In some embodiments, an anti-PD-L1 antibody comprises a heavy chain variable domain sequence as provided in SEQ ID NO: 45 and a light chain variable domain sequence as provided in SEQ ID NO: 46.

In one embodiment, an anti-PD-L1 antibody comprises a heavy chain variable domain sequence that is at least about 80% identical, such as about 85%, about 90%, about 95%, or about 99% identical to the sequence as provided in SEQ ID NO: 36, and comprises a light chain variable domain sequence that is at least about 80% identical, such as about 85%, about 90%, about 95%, or about 99% identical to the sequence as provided in SEQ ID NO: 43. In one embodiment, an anti-PD-L1 antibody comprises a heavy chain variable domain sequence as provided in SEQ ID NO: 36, and comprises a light chain variable domain sequence as provided in SEQ ID NO: 43.

In one embodiment, an anti-PD-L1 antibody comprises a heavy chain variable domain sequence that is at least about 80% identical, such as about 85%, about 90%, about 95%, or about 99% identical to the sequence as provided in SEQ ID NO: 37, and comprises a light chain variable domain sequence that is at least about 80% identical, such as about 85%, about 90%, about 95%, or about 99% identical to the sequence as provided in SEQ ID NO: 43. In one embodiment, an anti-PD-L1 antibody comprises a heavy chain variable domain sequence as provided in SEQ ID NO: 37, and comprises a light chain variable domain sequence as provided in SEQ ID NO: 43.

In one embodiment, an anti-PD-L1 antibody comprises a heavy chain variable domain sequence that is at least about 80% identical, such as about 85%, about 90%, about 95%, or about 99% identical to the sequence as provided in SEQ ID NO: 38, and comprises a light chain variable domain sequence that is at least about 80% identical, such as about 85%, about 90%, about 95%, or about 99% identical to the sequence as provided in SEQ ID NO: 43. In one embodiment, an anti-PD-L1 antibody comprises a heavy chain variable domain sequence as provided in SEQ ID NO: 38, and comprises a light chain variable domain sequence as provided in SEQ ID NO: 43.

In one embodiment, an anti-PD-L1 antibody comprises a heavy chain variable domain sequence that is at least about 80% identical, such as about 85%, about 90%, about 95%, or about 99% identical to the sequence as provided in SEQ ID NO: 39, and comprises a light chain variable domain sequence that is at least about 80% identical, such as about 85%, about 90%, about 95%, or about 99% identical to the sequence as provided in SEQ ID NO: 43. In one embodiment, an anti-PD-L1 antibody comprises a heavy chain variable domain sequence as provided in SEQ ID NO: 39, and comprises a light chain variable domain sequence as provided in SEQ ID NO: 43.

In one embodiment, an anti-PD-L1 antibody comprises a heavy chain variable domain sequence that is at least about 80% identical, such as about 85%, about 90%, about 95%, or about 99% identical to the sequence as provided in SEQ ID NO: 36, and comprises a light chain variable domain sequence that is at least about 80% identical, such as about 85%, about 90%, about 95%, or about 99% identical to the sequence as provided in SEQ ID NO: 44. In one embodiment, an anti-PD-L1 antibody comprises a heavy chain variable domain sequence as provided in SEQ ID NO: 36, and comprises a light chain variable domain sequence as provided in SEQ ID NO: 44.

In one embodiment, an anti-PD-L1 antibody comprises a heavy chain variable domain sequence that is at least about 80% identical, such as about 85%, about 90%, about 95%, or about 99% identical to the sequence as provided in SEQ ID NO: 37, and comprises a light chain variable domain sequence that is at least about 80% identical, such as about 85%, about 90%, about 95%, or about 99% identical to the sequence as provided in SEQ ID NO: 44. In one embodiment, an anti-PD-L1 antibody comprises a heavy chain variable domain sequence as provided in SEQ ID NO: 37, and comprises a light chain variable domain sequence as provided in SEQ ID NO: 44.

In one embodiment, an anti-PD-L1 antibody comprises a heavy chain variable domain sequence that is at least about 80% identical, such as about 85%, about 90%, about 95%, or about 99% identical to the sequence as provided in SEQ ID NO: 38, and comprises a light chain variable domain sequence that is at least about 80% identical, such as about 85%, about 90%, about 95%, or about 99% identical to the sequence as provided in SEQ ID NO: 44. In one embodiment, an anti-PD-L1 antibody comprises a heavy chain variable domain sequence as provided in SEQ ID NO: 38, and comprises a light chain variable domain sequence as provided in SEQ ID NO: 44.

In one embodiment, an anti-PD-L1 antibody comprises a heavy chain variable domain sequence that is at least about 80% identical, such as about 85%, about 90%, about 95%, or about 99% identical to the sequence as provided in SEQ ID NO: 39, and comprises a light chain variable domain sequence that is at least about 80% identical, such as about 85%, about 90%, about 95%, or about 99% identical to the sequence as provided in SEQ ID NO: 44. In one embodiment, an anti-PD-L1 antibody comprises a heavy chain variable domain sequence as provided in SEQ ID NO: 39, and comprises a light chain variable domain sequence as provided in SEQ ID NO: 44.

In one embodiment, an anti-PD-L1 antibody comprises a heavy chain variable domain sequence that is at least about 80% identical, such as about 85%, about 90%, about 95%, or about 99% identical to the sequence as provided in SEQ ID NO: 40, and comprises a light chain variable domain sequence that is at least about 80% identical, such as about 85%, about 90%, about 95%, or about 99% identical to the sequence as provided in SEQ ID NO: 43. In one embodiment, an anti-PD-L1 antibody comprises a heavy chain variable domain sequence as provided in SEQ ID NO: 40, and comprises a light chain variable domain sequence as provided in SEQ ID NO: 43.

In one embodiment, an anti-PD-L1 antibody comprises a heavy chain variable domain sequence that is at least about 80% identical, such as about 85%, about 90%, about 95%, or about 99% identical to the sequence as provided in SEQ ID NO: 41, and comprises a light chain variable domain sequence that is at least about 80% identical, such as about 85%, about 90%, about 95%, or about 99% identical to the sequence as provided in SEQ ID NO: 43. In one embodiment, an anti-PD-L1 antibody comprises a heavy chain variable domain sequence as provided in SEQ ID NO: 41, and comprises a light chain variable domain sequence as provided in SEQ ID NO: 43.

In one embodiment, an anti-PD-L1 antibody comprises a heavy chain variable domain sequence that is at least about 80% identical, such as about 85%, about 90%, about 95%, or about 99% identical to the sequence as provided in SEQ ID NO: 42, and comprises a light chain variable domain sequence that is at least about 80% identical, such as about 85%, about 90%, about 95%, or about 99% identical to the sequence as provided in SEQ ID NO: 43. In one embodiment, an anti-PD-L1 antibody comprises a heavy chain variable domain sequence as provided in SEQ ID NO: 42, and comprises a light chain variable domain sequence as provided in SEQ ID NO: 43.

In one embodiment, an anti-PD-L1 antibody comprises a heavy chain variable domain sequence that is at least about 80% identical, such as about 85%, about 90%, about 95%, or about 99% identical to the sequence as provided in SEQ ID NO: 40, and comprises a light chain variable domain sequence that is at least about 80% identical, such as about 85%, about 90%, about 95%, or about 99% identical to the sequence as provided in SEQ ID NO: 44. In one embodiment, an anti-PD-L1 antibody comprises a heavy chain variable domain sequence as provided in SEQ ID NO: 40, and comprises a light chain variable domain sequence as provided in SEQ ID NO: 44.

In one embodiment, an anti-PD-L1 antibody comprises a heavy chain variable domain sequence that is at least about 80% identical, such as about 85%, about 90%, about 95%, or about 99% identical to the sequence as provided in SEQ ID NO: 41, and comprises a light chain variable domain sequence that is at least about 80% identical, such as about 85%, about 90%, about 95%, or about 99% identical to the sequence as provided in SEQ ID NO: 44. In one embodiment, an anti-PD-L1 antibody comprises a heavy chain variable domain sequence as provided in SEQ ID NO: 41, and comprises a light chain variable domain sequence as provided in SEQ ID NO: 44.

In one embodiment, an anti-PD-L1 antibody comprises a heavy chain variable domain sequence that is at least about 80% identical, such as about 85%, about 90%, about 95%, or about 99% identical to the sequence as provided in SEQ ID NO: 42, and comprises a light chain variable domain sequence that is at least about 80% identical, such as about 85%, about 90%, about 95%, or about 99% identical to the sequence as provided in SEQ ID NO: 44. In one embodiment, an anti-PD-L1 antibody comprises a heavy chain variable domain sequence as provided in SEQ ID NO: 42, and comprises a light chain variable domain sequence as provided in SEQ ID NO: 44.

In some embodiments, an antibody comprising any of the sequences or combinations of sequences as recited herein is a monoclonal antibody. In some embodiments, an anti-PD-L1 antibody is a chimeric, humanized, or human antibody.

In some embodiments, an antibody comprises a human VH subgroup III (VH3) heavy chain framework consensus sequence. In some embodiments, an antibody comprises a human VH subgroup II (VH2) heavy chain framework consensus sequence. In some embodiments, an antibody comprises a human VH subgroup I (VH1) heavy chain framework consensus sequence. Examples of VH3 heavy chain FR1 sequences are provided in SEQ ID NOS: 10 and 11. Examples of VH3 heavy chain FR2 sequences are provided in SEQ ID NOS: 15 and 16. Examples of VH3 heavy chain FR3 sequences are provided in SEQ ID NOS: 22, 23 and 24.

In some embodiments, an antibody comprises a human kappa light chain framework consensus sequence. In some embodiments, an antibody comprises a human lambda light chain framework consensus sequence.

As is known in the art, and as described in greater detail herein, the amino acid position/boundary delineating a hypervariable region of an antibody can vary, depending on the context and the various definitions known in the art (as described below). Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions (as further defined below). The invention provides antibodies comprising modifications in these hybrid hypervariable positions. In one embodiment, these hypervariable positions include one or more of positions 26-30, 33-35B, 47-49, 57-65, 93, 94 and 101-102 in a heavy chain variable domain. In one embodiment, these hybrid hypervariable positions include one or more of positions 24-29, 35-36, 46-49, 56 and 97 in a light chain variable domain.

Antibodies in accordance with aspects of the invention specifically include all isotypes, sub-classes and forms of antibodies, including, without limitation, IgG, IgM, IgA, IgD, and IgE antibodies and their fragments, preferably antigen-binding fragments. Preferred antibodies herein include IgG, IgM and IgA antibodies and their antigen-binding fragments, which may be modified to include sequences from other isotypes, such as IgG to produce chimeric antibodies.

In some embodiments, an anti-PD-L1 antibody is an IgG antibody. In certain embodiments, an IgG antibody is a subclass selected from the group consisting of: IgG1, IgG2 (IgG2a, IgG2b), IgG3 or IgG4.

In some embodiments, an anti-PD-L1 antibody is an IgM antibody. IgM antibodies are described in published PCT application PCT/US2014/054079, the disclosure of which is herein incorporated by reference in its entirety.

In some embodiments, an anti-PD-L1 antibody is an IgA antibody. In certain embodiments, an IgA antibody is a subclass selected from the group consisting of: IgA1 or IgA2. IgA antibodies are described in published PCT application PCT/US2015/015268, the disclosure of which is herein incorporated by reference in its entirety.

In some embodiments, an anti-PD-L1 antibody is an IgM antibody that comprises a modified J-chain. In some embodiments, an anti-PD-L1 antibody is an IgA antibody that comprises a modified J-chain. In some embodiments, an anti-PD-L1 antibody is an IgG/IgM hybrid antibody that comprises a modified J-chain. In some embodiments, an anti-PD-L1 antibody is an IgG/IgA hybrid antibody that comprises a modified J-chain. IgM, IgA, IgG/IgM and IgG/IgA antibodies that comprise a modified J-chain are described in published PCT application PCT/US2015/024149, the disclosure of which is herein incorporated by reference in its entirety.

Antibodies in accordance with embodiments of the invention can be monospecific, bispecific or multi-specific. Bispecific IgG antibodies are described, for example in U.S. Patent Publication No. 2014/0120096, the disclosure of which is incorporated herein by reference in its entirety.

Aspects of the invention include bispecific IgM antibodies with binding specificities to two different binding regions. Bispecific IgM antibodies are described in published PCT application PCT/US2014/054079, the disclosure of which is herein incorporated by reference in its entirety.

Aspects of the invention include bispecific IgA antibodies with binding specificities to two different binding regions. Bispecific IgA antibodies are described, for example, in published PCT application PCT/US2015/015268, the disclosure of which is herein incorporated by reference in its entirety.

Aspects of the invention include IgG/IgM and IgG/IgA hybrid antibodies. Such antibodies are described in published PCT application PCT/US2015/024149, the disclosure of which is herein incorporated by reference in its entirety.

In one particular embodiment, a full length anti-PD-L1 antibody is an IgG antibody.

In one particular embodiment, a full length anti-PD-L1 antibody is an IgM antibody. In one embodiment, a full length anti-PD-L1 IgM antibody comprises a modified J-chain that comprises an extraneous binding moiety.

In one particular embodiment, a full length anti-PD-L1 antibody is an IgA antibody. In one embodiment, a full length anti-PD-L1 IgA antibody comprises a modified J-chain that comprises an extraneous binding moiety.

In one particular embodiment, a full length anti-PD-L1 antibody is an IgG/IgM antibody hybrid antibody. In one embodiment, a full length anti-PD-L1 IgG/IgM hybrid antibody comprises a modified J-chain that comprises an extraneous binding moiety.

In one particular embodiment, a full length anti-PD-L1 antibody is an IgG/IgA hybrid antibody. In one embodiment, a full length anti-PD-L1 IgG/IgA antibody comprises a modified J-chain that comprises an extraneous binding moiety.

Amino acid sequences that are referred to herein are provided in Table 1, below:

TABLE 1

| Amino acid sequences | | |
|---|---|---|
| Sequence Name | Sequence | SEQ ID NO: |
| HVR-L1 | RASQDISIWLS | SEQ ID NO: 1 |
| HVR-L2 | KASNLHT | SEQ ID NO: 2 |
| HVR-L3 | LQSQSFPRT | SEQ ID NO: 3 |
| HVR-H1 | GFSLTSYDIS | SEQ ID NO: 4 |
| HVR-H2 | VIWTGVGTN | SEQ ID NO: 5 |
| HVR-H3 | DPYYYGMDY | SEQ ID NO: 6 |
| HC-FR1 (h3C5H1; h3C5H2) | QVQLKESGPGLVAPSQSLSITCTVS | SEQ ID NO: 7 |
| HC-FR1 (h3C5H3) | QVQLQESGPGLVKPSETLSLTCTVS | SEQ ID NO: 8 |
| HC-FR1 (h3C5H4) | QVQLQESGPGLVKPSETLSITCTVS | SEQ ID NO: 9 |
| HC-FR1 (h3C5H3-1) | EVQLVESGGGLVQPGGSLRLSCAAS | SEQ ID NO: 10 |
| HC-FR1 (h3C5H3-2; h3C5H3-3) | EVQLVESGGGLVQPGGSLRISCAVS | SEQ ID NO: 11 |
| HC FR2 (h3C5H1) | WVRQPPGKGLEWLG | SEQ ID NO: 12 |

TABLE 1-continued

Amino acid sequences

| Sequence Name | Sequence | SEQ ID NO: |
|---|---|---|
| HC FR2 (h3C5H2) | WIRQPPGKGLEWIG | SEQ ID NO: 13 |
| HC FR2 (h3C5H3; h3C5H4) | WIRQPPGKGLEWLG | SEQ ID NO: 14 |
| HC FR2 (h3C5H3-1) | WVRQAPGKGLEWVS | SEQ ID NO: 15 |
| HC FR2 (h3C5H3-2; h3C5H3-3) | WVRQAPGKGLEWLG | SEQ ID NO: 16 |
| HC FR3 (3C5) | YNSAFMSRLSISKDNSKSQVFLKMNSLQTDDTAMYYCVR | SEQ ID NO: 17 |
| HC FR3 (4-59; h3C5H1) | YNPSLKSRVTISVDTSKNQFSLKLSSVTAADTAVYYCAR | SEQ ID NO: 18 |
| HC FR3 (h3C5H2) | YNPSLKSRVTISKDTSKNQFSLKLSSVTAADTAVYYCAR | SEQ ID NO: 19 |
| HC FR3 (h3C5H3) | YNPSFKSRLTISKDTSKNQVSLKMSSLTAADTAVYYCVR | SEQ ID NO: 20 |
| HC FR3 (h3C5H4) | YNPSFKSRLTISKDNSKNQVSLKMSSLTAADTAVYYCVR | SEQ ID NO: 21 |
| HC FR3 (h3C5H3-1) | YADSVKGRFTISRDNSKNTLYLQMNSLRAEDTAVYYCAR | SEQ ID NO: 22 |
| HC FR3 (h3C5H3-2) | YADSFKGRLTISRDNSKNTVYLQMNSLRAEDTAVYYCVR | SEQ ID NO: 23 |
| HC FR3 (h3C5H3-3) | YADSFKGRLTISKDNSKNTVYLQMNSLRAEDTAVYYCVR | SEQ ID NO: 24 |
| HC FR4 | WGQGTSVTVSS | SEQ ID NO: 25 |
| HC FR4 | WGQGTLVTVSS | SEQ ID NO: 26 |
| LC FR1 | DIQMNQSPSSLSASLGDTITITC | SEQ ID NO: 27 |
| LC FR1 | DIQMTQSPSSLSASVGDRVTITC | SEQ ID NO: 28 |
| LC FR1 | DIQMTQSPSSLSASVGDRITITC | SEQ ID NO: 29 |
| LC FR2 | WYQQKPGNIPELLIY | SEQ ID NO: 30 |
| LC FR2 | WYQQKPGKAPKLLIY | SEQ ID NO: 31 |
| LC FR3 | GVPPRFSGSGSGTDFTLTISSLQPEDIATYYC | SEQ ID NO: 32 |
| LC FR3 | GVPSRFSGSGSGTDFTLTISSLQPEDFATYYC | SEQ ID NO: 33 |
| LC FR4 | FGGGTKLEIK | SEQ ID NO: 34 |
| LC FR4 | FGQGTKLEIK | SEQ ID NO: 35 |
| HC Variable Domain (h3C5H1) | QVQLQESGPGLVKPSETLSLTCTVSGFSLTSYDISWIRQPPGKGLEWIGVIWTGVGTNYNPSLKSRVTISVDTSKNQFSLKLSSVTAADTAVYYCARDPYYYGMDYWGQGTLVTVSS | SEQ ID NO: 36 |
| HC Variable Domain (h3C5H2) | QVQLQESGPGLVKPSETLSLTCTVSGFSLTSYDISWIRQPPGKGLEWLGVIWTGVGTNYNPSLKSRVTISKDTSKNQFSLKLSSVTAADTAVYYCARDPYYYGMDYWGQGTLVTVSS | SEQ ID NO: 37 |
| HC Variable Domain (h3C5H3) | QVQLQESGPGLVKPSETLSITCTVSGFSLTSYDISWVRQPPGKGLEWLGVIWTGVGTNYNPSFKSRLTISKDTSKNQVSLKMSSLTAADTAVYYCVRDPYYYGMDYWGQGTLVTVSS | SEQ ID NO: 38 |

TABLE 1-continued

Amino acid sequences

| Sequence Name | Sequence | SEQ ID NO: |
|---|---|---|
| HC Variable Domain (h3C5H4) | QVQLQESGPGLVKPSETLSITCTVSGFSLTSY DISWIRQPPGKGLEWLGVIWTGVGTNYNPS FKSRLTISKDNSKNQVSLKMSSLTAADTAV YYCVRDPYYYGMDYWGQGTLVTVSS | SEQ ID NO: 39 |
| HC Variable Domain (h3C5H3-1) | EVQLVESGGGLVQPGGSLRLSCAASGFSLT SYDISWVRQAPGKGLEWVSVIWTGVGTNY ADSVKGRFTISRDNSKNTLYLQMNSLRAEDTAV YYCARDPYYYGMDYWGQGTLVTVSS | SEQ ID NO: 40 |
| HC Variable Domain (h3C5H3-2) | EVQLVESGGGLVQPGGSLRISCAVSGFSLT SYDISWVRQAPGKGLEWLGVIWTGVGTNY ADSFKGRLTISRDNSKNTVYLQMNSLRAEDTA VYYCVRDPYYYGMDYWGQGTLVTVSS | SEQ ID NO: 41 |
| HC Variable Domain (h3C5H3-3) | EVQLVESGGGLVQPGGSLRISCAVSGFSLT SYDISWVRQAPGKGLEWLGVIWTGVGTNY ADSFKGRLTISKDNSKNTVYLQMNSLRAEDTAV YYCVRDPYYYGMDYWGQGTLVTVSS | SEQ ID NO: 42 |
| LC Variable Domain (h3C5L1) | DIQMTQSPSSLSASVGDRVTITCRASQDISIWL SWYQQKPGKAPKLLIYKASNLHTGVPSRFSG SGSGTDFTLTISSLQPEDFATYYCLQSQSFPRTFG QGTKLEIK | SEQ ID NO: 43 |
| LC Variable Domain (h3C5L2) | DIQMTQSPSSLSASVGDRITITCRASQDISIWLS WYQQKPGKAPKLLIYKASNLHTGVPSRFSGS GSGTDFTLTISSLQPEDFATYYCLQSQSFPRTFG QGTKLEIK | SEQ ID NO: 44 |
| 3C5 Variable Domain (3C5 HC) | QVQLKESGPGLVAPSQSLSITCTVSGFSLTSY DISWVRQPPGKGLEWLGVIWTGVGTNYNSA FMSRLSISKDNSKSQVFLKMNSLQTDDTAM YYCVRDPYYYGMDYWGQGTSVTVSS | SEQ ID NO: 45 |
| 3C5 Variable Domain (3C5 LC) | DIQMNQSPSSLSASLGDTITITCRASQDISIWL SWYQQKPGNIPELLIYKASNLHTGVPPRFSGS GSGTDFTLTISSLQPEDIATYYCLQSQSFPRTF GGGTKLEIK | SEQ ID NO: 46 |
| J-chain sequence (WT J-chain) | QEDERIVLVDNKCKCARITSRIIRSSEDPNEDIV ERNIRIIVPLNNRENISDPTSPLRTRFVYHLSDLC KKCDPTEVELDNQIVTATQSNICDEDSATECY TYDRNKCYTAVVPLVYGGETKMVETALTPDA CYPD | SEQ ID NO: 47 |
| PD-L1 sequence (Human PD-L1) | MRIFAVFIFMTYWHLLNAFTVTVPKDLYVVE YGSNMTIECKFPVEKQLDLAALIVYWEMEDK NIIQFVHGEEDLKVQHSSYRQRARLLKDQLSL GNAALQITDVKLQDAGVYRCMISYGGADYK RITVKVNAPYNKINQRILVVDPVTSEHELTCQ AEGYPKAEVIWTSSDHQVLSGKTTTTNSKR EEKLFNVTSTLRINTTTNEIFYCTFRRLDPEEN HTAELVIPELPLAHPPNERTHLVILGAILLCLG VALTFIFRLRKGRMMDVKKCGIQDTNSKKQ SDTHLEET | SEQ ID NO: 48 |
| Full Length HC sequence (3C5-2G12 IgG1 HC) | MDPKGSLSWRILLFLSLAFELSYGQVQLKESG PGLVAPSQSLSITCTVSGFSLTSYDISWVRQPP GKGLEWLGVIWTGVGTNYNSAFMSRLSISKD NSKSQVFLKMNSLQTDDTAMYYCVRDPYYY GMDYWGQGTSVTVSSASTKGPSVFPLAPSSK STSGGTAALGCLVKDYFPEPVTVSWNSGALT SGVHTFPAVLQSSGLYSLSSVVTVPSSSLGTQ TYICNVNHKPSNTKVDKKVEPKSCDKTHTCP PCPAPELLGGPSVFLFPPKPKDTLMISRTPEVT CVVVDVSHEDPEVKFNWYVDGVEVHNAKTK PREEQYNSTYRVVSVLTVLHQDWLNGKEYKC KVSNKALPAPIEKTISKAKGQPREPQVYTLPPS RDELTKNQVSLTCLVKGFYPSDIAVEWESNGQ PENNYKTTPPVLDSDGSFFLYSKLTVDKSRWQ QGNVFSCSVMHEALHNHYTQKSLSLSPG | SEQ ID NO: 49 |
| Full Length HC sequence (3C5-2G12 IgM HC) | MDPKGSLSWRILLFLSLAFELSYGQVQLKESGP GLVAPSQSLSITCTVSGFSLTSYDISWVRQPPGK GLEWLGVIWTGVGTNYNSAFMSRLSISKDNSK | SEQ ID NO: 50 |

TABLE 1-continued

Amino acid sequences

| Sequence Name | Sequence | SEQ ID NO: |
|---|---|---|
| | SQVFLKMNSLQTDDTAMYYCVRDPYYYGMD YWGQGTSVTVSSGSASAPTLFPLVSCENSPSDT SSVAVGCLAQDFLPDSITFSWKYKNNSDISSTR GFPSVLRGGKYAATSQVLLPSKDVMQGTDEH VVCKVQHPNGNKEKNVPLPVIAELPPKVSVFV PPRDGFFGNPRKSKLICQATGFSPRQIQVSWLR EGKQVGSGVTTDQVQAEAKESGPTTYKVTSTL TIKESDWLSQSMFTCRVDHRGLTFQQNASSMC VPDQDTAIRVFAIPPSFASIFLTKSTKLTCLVTDL TTYDSVTISWTRQNGEAVKTHTNISESHPNATF SAVGEASICEDDWNSGERFTCTVTHTDLPSPLK QTISRPKGVALHRPDVYLLPPAREQLNLRESATI TCLVTGFSPADVFVQWMQRGQPLSPEKYVTSA PMPEPQAPGRYFAHSILTVSEEEWNTGETYTCV VAHEALPNRVTERTVDKSTGKPTLYNVSLVMS DTAGTCY | |
| Full Length LC Sequence (3C5-2G12 IgG, IgM LC) | METDTLLLWVLLLWVPGSTGDIQMNQSPSSLSA SLGDTITITCRASQDISIWLSWYQQKPGNIPELLI YKASNLHTGVPPRFSGSGSGTDFTLTISSLQPEDI ATYYCLQSQSFPRTFGGGTKLEIKRTVAAPSVFIF PPSDEQLKSGTASVVCLLNNFYPREAKVQWKVD NALQSGNSQESVTEQDSKDSTYSLSSTLTLSKADY EKHKVYACEVTHQGLSSPVTKSFNRGEC | SEQ ID NO: 51 |
| Full Length HC Sequence (h3C5H1-hIgG1) | MDPKGSLSWRILLFLSLAFELSYGQVQLQESGP GLVKPSETLSLTCTVSGFSLTSYDISWIRQPPGK GLEWIGVIWTGVGTNYNPSLKSRVTISVDTSKN QFSLKLSSVTAADTAVYYCARDPYYYGMDYW GQGTLVTVSSASTKGPSVFPLAPSSKSTSGGTA ALGCLVKDYFPEPVTVSWNSGALTSGVHTFPA VLQSSGLYSLSSVVTVPSSSLGTQTYICNVNHK PSNTKVDKKVEPKSCDKTHTCPPCPAPELLGGP SVFLFPPKPKDTLMISRTPEVTCVVVDVSHEDPE VKFNWYVDGVEVHNAKTKPREEQYNSTYRVV SVLTVLHQDWLNGKEYKCKVSNKALPAPIEKTI SKAKGQPREPQVYTLPPSRDELTKNQVSLTCLVK GFYPSDIAVEWESNGQPENNYKTTPPVLDSDGSF FLYSKLTVDKSRWQQGNVFSCSVMHEALHNHY TQKSLSLSPG | SEQ ID NO: 52 |
| Full Length HC Sequence (h3C5H2-hIgG1) | MDPKGSLSWRILLFLSLAFELSYGQVQLQESGPGL VKPSETLSLTCTVSGFSLTSYDISWIRQPPGKGLE WLGVIWTGVGTNYNPSLKSRVTISKDTSKNQFSL KLSSVTAADTAVYYCARDPYYYGMDYWGQGTL VTVSSASTKGPSVFPLAPSSKSTSGGTAALGCLVK DYFPEPVTVSWNSGALTSGVHTFPAVLQSSGLYSL SSVVTVPSSSLGTQTYICNVNHKPSNTKVDKKVEP KSCDKTHTCPPCPAPELLGGPSVFLFPPKPKDTLMI SRTPEVTCVVVDVSHEDPEVKFNWYVDGVEVHN AKTKPREEQYNSTYRVVSVLTVLHQDWLNGKEY KCKVSNKALPAPIEKTISKAKGQPREPQVYTLPPS RDELTKNQVSLTCLVKGFYPSDIAVEWESNGQPE NNYKTTPPVLDSDGSFFLYSKLTVDKSRWQQGN VFSCSVMHEALHNHYTQKSLSLSPG | SEQ ID NO: 53 |
| Full Length HC Sequence (h3C5H3-hIgG1) | MDPKGSLSWRILLFLSLAFELSYGQVQLQESGP GLVKPSETLSITCTVSGFSLTSYDISWVRQPPGK GLEWLGVIWTGVGTNYNPSFKSRLTISKDTSKN QVSLKMSSLTAADTAVYYCVRDPYYYGMDYW GQGTLVTVSSASTKGPSVFPLAPSSKSTSGGTAA LGCLVKDYFPEPVTVSWNSGALTSGVHTFPAVL QSSGLYSLSSVVTVPSSSLGTQTYICNVNHKPSN TKVDKKVEPKSCDKTHTCPPCPAPELLGGPSVFL FPPKPKDTLMISRTPEVTCVVVDVSHEDPEVKFN WYVDGVEVHNAKTKPREEQYNSTYRVVSVLTVL HQDWLNGKEYKCKVSNKALPAPIEKTISKAKGQP REPQVYTLPPSRDELTKNQVSLTCLVKGFYPSDIA VEWESNGQPENNYKTTPPVLDSDGSFFLYSKLTV DKSRWQQGNVFSCSVMHEALHNHYTQKSLSLSPG | SEQ ID NO: 54 |
| Full Length HC Sequence (h3C5H4-hIgG1) | MDPKGSLSWRILLFLSLAFELSYGQVQLQESGPGL VKPSETLSITCTVSGFSLTSYDISWIRQPPGKGLEW LGVIWTGVGTNYNPSFKSRLTISKDNSKNQVSLK MSSLTAADTAVYYCVRDPYYYGMDYWGQGTL VTVSSASTKGPSVFPLAPSSKSTSGGTAALGCLV | SEQ ID NO: 55 |

TABLE 1-continued

Amino acid sequences

| Sequence Name | Sequence | SEQ ID NO: |
|---|---|---|
| | KDYFPEPVTVSWNSGALTSGVHTFPAVLQSSGL<br>YSLSSVVTVPSSSLGTQTYICNVNHKPSNTKVD<br>KKVEPKSCDKTHTCPPCPAPELLGGPSVFLFPPK<br>PKDTLMISRTPEVTCVVVDVSHEDPEVKFNWY<br>VDGVEVHNAKTKPREEQYNSTYRVVSVLTVLH<br>QDWLNGKEYKCKVSNKALPAPIEKTISKAKGQP<br>REPQVYTLPPSRDELTKNQVSLTCLVKGFYPSDI<br>AVEWESNGQPENNYKTTPPVLDSDGSFFLYSKL<br>TVDKSRWQQGNVFSCSVMHEALHNHYTQKSL<br>SLSPG | |
| Full Length LC Sequence (h3C5L1-hKappa) | METDTLLLWVLLLWVPGSTGDIQMTQSPSSLS<br>ASVGDRVTITCRASQDISIWLSWYQQKPGKA<br>PKLLIYKASNLHTGVPSRFSGSGSGTDFTLTIS<br>SLQPEDFATYYCLQSQSFPRTFGQGTKLEIKR<br>TVAAPSVFIFPPSDEQLKSGTASVVCLLNNFY<br>PREAKVQWKVDNALQSGNSQESVTEQDSKD<br>STYSLSSTLTLSKADYEKHKVYACEVTHQGL<br>SSPVTKSFNRGEC | SEQ ID NO: 56 |
| Full Length LC Sequence (h3C5L2-hKappa) | METDTLLLWVLLLWVPGSTGDIQMTQSPS<br>SLSASVGDRITITCRASQDISIWLSWYQQK<br>PGKAPKLLIYKASNLHTGVPSRFSGSGSGT<br>DFTLTISSLQPEDFATYYCLQSQSFPRTFGQ<br>GTKLEIKRTVAAPSVFIFPPSDEQLKSGTAS<br>VVCLLNNFYPREAKVQWKVDNALQSGNS<br>QESVTEQDSKDSTYSLSSTLTLSKADYEKH<br>KVYACEVTHQGLSSPVTKSFNRGEC | SEQ ID NO: 57 |

Aspects of the invention include antibodies that comprise a J-chain that comprises a binding moiety that antagonizes a T-cell inhibitory signaling pathway, without interfering with the ability of the IgM, IgA, IgG/IgM or IgG/IgA antibody to bind to its binding target(s) (e.g., PD-L1). An antibody in accordance with embodiments of the invention can be, for example, an IgM antibody, an IgA antibody, or an IgG/IgM or IgG/IgA hybrid antibody, which may contain an IgM or IgA tail-piece at the IgG heavy chain and thus combine the properties of IgG and IgM or IgA, including the ability to incorporate and form polymers with a modified J-chain whose binding moiety antagonizes a T-cell inhibitory signaling pathway. For further details on IgG/IgM and IgG/IgA hybrid antibodies see, e.g., Koteswara et al., Clinical Immunology 2001, 101(1):21-31.

T-cell inhibitory signaling pathways are known in the art, and include, without limitation, those described in Pardoll, Drew M "The blockade of immune checkpoints in cancer immunotherapy." *Nature Reviews Cancer* 12.4 (2012): 252-264, the disclosure of which is herein incorporated by reference in its entirety. Non-limiting examples of T-cell inhibitory signaling pathways and components thereof are described in further detail below.

Programmed cell death-1 (PD-1) and its ligand, programmed cell death ligand-1 (PD-L1) are generally involved with immunosuppressive activity of T-cells. PD-1 is an inhibitory cell surface receptor protein of the immunoglobulin superfamily, and is expressed on the surface of T-cells and is involved in the regulation of T-cell function in immunity and self-tolerance. PD-L1 interacts with PD-1 on the surface of T-cells, and inhibits proliferation of T-cells by blocking cell cycle progression and cytokine production. Id. Examples of the immunosuppressive functions of PD-1 include, but are not limited to, exhaustion, anergy, and quiescence of T-cells that express PD-1. As reviewed above, in some embodiments, an anti-PD-L1 antibody, or antigen-binding fragment thereof, is capable of binding to a PD-L1 protein and thereby inhibiting one or more of the immunosuppressive functions of a PD-1 protein.

Cytotoxic T-lymphocyte-associated protein 4 (CTLA-4) is a member of the immunoglobulin superfamily and has been shown to transmit an inhibitory signal to T-cells. The membrane-bound isoform of CTLA-4 functions as a homodimer interconnected by a disulfide bond, while the soluble isoform functions as a monomer. E.g., Pardoll at 255.

Another example of a T-cell inhibitory signaling pathway is the signaling pathway involving T-cell immunoglobulin and mucin domain 3 (TIM3). TIM3 is a cell surface glycoprotein that is expressed on the surface of T-cells, and functions as an inhibitory molecule that is involved in the termination of Th1 cells. Id.

Another example of a T-cell inhibitory signaling pathway is the signaling pathway involving lymphocyte-activation gene 3 (LAG3). LAG3 belongs to the immunoglobulin superfamily, and functions as an inhibitor of cellular proliferation, activation and homeostasis of T-cells. Id.

Another example of a T-cell inhibitory signaling pathway is the signaling pathway involving B- and T-lymphocyte attenuator protein (BTLA). BTLA is a cell surface protein that functions by inhibiting T-cells via interaction with members of the tumor necrosis factor receptor superfamily. BTLA is known to negatively regulate T-cell immune responses. Id.

Another example of a T-cell inhibitory signaling pathway is the signaling pathway involving V-domain Ig suppressor of T-cell activation (VISTA). VISTA is a regulator of T-cell function that is expressed on hematopoietic cells and leukocytes, and functions by suppressing T-cell activation. E.g., Lines J L, et al., Cancer research. 2014; 74(7):1924-1932.

Another example of a T-cell inhibitory signaling pathway is the signaling pathway involving the protein T-cell immunoreceptor with Ig and ITIM Domains (TIGIT). TIGIT is expressed in several classes of T-cells, and binds with high affinity to the poliovirus receptor. TIGIT suppresses T-cell activation by promoting generation of mature immunoregulatory dendritic cells. E.g., Yu X. et al., *Nat Immunol.* 2009 January; 10(1):48-57.

As reviewed above, antibodies in accordance with embodiments of the invention can comprise a binding moiety on the J-chain that antagonizes a T-cell inhibitory signaling pathway. In some embodiments, a binding moiety on the J-chain binds to a target in a T-cell inhibitory signaling pathway, and thereby blocks or diminishes inhibitory signals that are received by a T-cell via the pathway. As a result, the T-cell's immune response is not blocked, halted or diminished, or, at least, the inhibition of the T-cell's immune response is reduced or diminished. The binding moiety on the J-chain of a subject antibody can be used to antagonize any T-cell inhibitory signaling pathway, including but not limited to the inhibitory signaling pathways that involve the proteins listed in Table 2, below. The GenBank Accession Numbers corresponding to the human protein sequences of these T-cell inhibitory signaling pathway targets are provided in Table 2, below.

TABLE 2

Sequence information for T-cell inhibitory signaling pathway targets

| T-cell inhibitory signaling pathway member: | GenBank Accession No. |
|---|---|
| CTLA-4 | AAL07473.1 |
| TIM3 | AAL65158.1 |
| LAG3 | AAH52589.1 |
| BTLA | AAI07092.1 |
| VISTA | NP_071436.1 |
| TIGIT | NP_776160.2 |

Aspects of the invention include anti-PD-L1 antibodies having a J-chain that comprises a binding moiety that reduces clearance of the antibody from the circulation of a subject, thereby increasing the half-life of the antibody in the subject. Albumin binding is known in the art as a general strategy for improving the pharmacokinetics of a protein. For example, non-covalent association with albumin has been shown to extend the half-life of short lived proteins. E.g., Dennis, Mark S. et al., *J. Biol. Chem.*, 2002, 277: 35035-35043, the disclosure of which is incorporated by reference herein in its entirety. As such, the use of albumin (human serum albumin), albumin-like proteins, or albumin binding peptides as a binding moiety on a J-chain in a subject anti-PD-L1 antibody provides an effective strategy for manipulating the pharmacokinetics of the antibody. In addition, the neonatal Fc receptor (FcRn) is known to provide a recycling pathway that provides immunoglobulin molecules with a longer circulating half-life. E.g., Roopenian D. C. et al., *Nature Reviews Immunology* 7, 715-725 (2007). As such, the use of FcRn-binding proteins, Fc domains that bind to FcRn, or antibody moieties that bind to FcRn, also provides an effective strategy for manipulating the pharmacokinetics of an antibody.

In some embodiments, a binding moiety on a J-chain of a subject anti-PD-L1 antibody comprises an albumin protein. Albumin proteins are soluble, non-glycosylated proteins that are commonly found in blood plasma. Albumin proteins are known to interact with the FcRn-mediated recycling pathway, and as a result, have an extraordinarily long circulatory half-life.

In certain embodiments, a binding moiety on a J-chain of a subject anti-PD-L1 antibody binds to an albumin protein, thereby connecting itself to an albumin protein and taking advantage of the FcRn-mediated recycling pathway. As such, in certain embodiments, a binding moiety on a J-chain of a subject anti-PD-L1 antibody comprises an albumin-binding peptide. Non-limiting examples of albumin-binding peptides are described in US Patent Publication No. US20050287153, the disclosure of which is incorporated by reference herein in its entirety. In some embodiments, a binding moiety on a J-chain of a subject anti-PD-L1 antibody comprises an albumin-binding antibody moiety. Non-limiting examples of antibody moieties that bind to albumin include anti-albumin Fab, anti-albumin scFv, anti-albumin VHH (e.g., a camelid-like antibody molecule), anti-albumin scFab, and anti-albumin dAb (e.g., a human domain antibody).

In some embodiments, a binding moiety on a J-chain of a subject anti-PD-L1 antibody comprises an FcRn-binding peptide. In certain embodiments, a binding moiety on a J-chain of a subject anti-PD-L1 antibody comprises an FcRn-binding antibody moiety. Non-limiting examples of antibody moieties that bind to FcRn include anti-FcRn Fab, anti-FcRn scFv, anti-FcRn VHH, anti-FcRn scFab, and anti-FcRn dAb.

In some embodiments, a binding moiety on a J-chain of a subject anti-PD-L1 antibody comprises an Fc domain of an immunoglobulin molecule that is bound by an FcRn receptor. Binding moieties that can be included on a J-chain of a subject anti-PD-L1 antibody in order to reduce the clearance of the anti-PD-L1 antibody include, without limitation, the binding moieties provided below in Table 3. Non-limiting examples of proteins that can be used to generate an antibody moiety that can be used as a binding moiety on a J-chain of a subject anti-PD-L1 antibody are also provided in Table 3.

TABLE 3

Sequence information for clearance reducing binding moieties

| Clearance-reducing binding moiety | Amino acid sequence information |
|---|---|
| albumin | GenBank Accession No.: NP_000468.1 |
| albumin binding peptide | DLCLRDWGCLW (SEQ ID NO: 58) |
| albumin binding peptide | DICLPRWGCLW (SEQ ID NO: 59) |
| albumin binding peptide | MEDICLPRWGCLWGD (SEQ ID NO: 60) |
| albumin binding peptide | QRLMEDICLPRWGCLWEDDE (SEQ ID NO: 61) |
| albumin binding peptide | QGLIGDICLPRWGCLWGRSV (SEQ ID NO: 62) |

TABLE 3-continued

Sequence information for clearance reducing binding moieties

| Clearance-reducing binding moiety | Amino acid sequence information |
|---|---|
| albumin binding peptide | QGLIGDICLPRWGCLWGRSVK (SEQ ID NO: 63) |
| albumin binding peptide | EDICLPRWGCLWEDD (SEQ ID NO: 64) |
| albumin binding peptide | RLMEDICLPRWGCLWEDD (SEQ ID NO: 65) |
| albumin binding peptide | MEDICLPRWGCLWEDD (SEQ ID NO: 66) |
| albumin binding peptide | MEDICLPRWGCLWED (SEQ ID NO: 67) |
| albumin binding peptide | RLMEDICLARWGCLWEDD (SEQ ID NO: 68) |
| albumin binding peptide | EVRSFCTRWPAEKSCKPLRG (SEQ ID NO: 69) |
| albumin binding peptide | RAPESFVCYWETICFERSEQ (SEQ ID NO: 70) |
| albumin binding peptide | EMCYFPGICWM (SEQ ID NO: 71) |
| FcRn | GenBank Accession No.: P55899.1 |
| Fc domain of IgG1 | GenBank Accession No.: AAB24269.1 |
| Fc domain of IgG2 | GenBank Accession No.: AAR26706.1 |
| Fc domain of IgG3 | GenBank Accession No.: ACO54886.1 |
| Fc domain of IgG4 | GenBank Accession No.: AAG00912.1 |

A binding moiety on the J-chain of a subject antibody can include, without limitation: antibodies, antigen-binding fragments of antibodies, antibody-drug conjugates, antigen-binding fragments of antibody-drug conjugate, antibody-like molecules, antigen-binding fragments of antibody-like molecules, soluble and membrane-bound proteins, ligands and receptors. In some embodiments, an antigen-binding fragment of an antibody is selected from the group consisting of: Fab, Fab', F(ab)$_2$, F(ab')$_2$, Fv, scFv and single domain antibody. In a preferred embodiment, a binding moiety on a J-chain is an antibody or an antigen-binding fragment of an antibody (also referred to as an "antibody fragment"), including monospecific, bispecific, and multi-specific antibodies and antibody fragments, that functions as an antagonist of a T-cell inhibitory signaling pathway. In a preferred embodiment, the antibody fragment is a single chain Fv (scFv).

Aspects of the invention include an IgM, IgA, IgG/IgM or IgG/IgA antibody, or an antigen-binding fragment thereof, that binds to a cell surface protein (e.g., a CD20, EGFR, HER2, CTLA-4, TIM3, LAG3, VISTA or TIGIT protein), wherein the IgM, IgA, IgG/IgM or IgG/IgA antibody, or an antigen-binding fragment, comprises a modified J-chain that comprises an extraneous binding moiety, which comprises an anti-PD-L1 antibody, or antigen-binding fragment, as described herein.

In some aspects, the invention provides vectors comprising DNA encoding any of the herein described anti-PD-L1 antibodies. Host cells comprising any such vector are also provided. By way of example, the host cells may be CHO cells, E. coli cells, or yeast cells. A process for producing any of the herein described polypeptides is further provided and comprises culturing host cells under conditions suitable for expression of the desired polypeptide and recovering the desired polypeptide from the cell culture.

Antibodies in accordance with embodiments of the invention can be employed in any known assay method, such as ELISA, competitive binding assays, direct and indirect sandwich assays, and immunoprecipitation assays (Zola, (1987) Monoclonal Antibodies: A Manual of Techniques, pp. 147-158, CRC Press, Inc.).

A detection label may be useful for localizing, visualizing, and quantitating a binding or recognition event. A labelled antibody of the invention can detect cell-surface receptors. Another use for detectably labelled antibodies is a method of bead-based immunocapture comprising conjugating a bead with a fluorescent labelled antibody and detecting a fluorescence signal upon binding of a ligand. Similar binding detection methodologies utilize the surface plasmon resonance (SPR) effect to measure and detect antibody-antigen interactions.

Detection labels such as fluorescent dyes and chemiluminescent dyes (Briggs et al (1997) "Synthesis of Functionalised Fluorescent Dyes and Their Coupling to Amines and Amino Acids," J. Chem. Soc., Perkin-Trans. 1:1051-1058) provide a detectable signal and are generally applicable for labelling antibodies, preferably with the following properties: (i) the labelled antibody should produce a very high signal with low background so that small quantities of antibodies can be sensitively detected in both cell-free and cell-based assays; and (ii) the labelled antibody should be photostable so that the fluorescent signal may be observed, monitored and recorded without significant photo bleaching. For applications involving cell surface binding of labelled antibody to membranes or cell surfaces, especially live cells, the labels preferably (iii) have good water-solubility to achieve effective conjugate concentration and detection sensitivity and (iv) are non-toxic to living cells so as not to disrupt the normal metabolic processes of the cells or cause premature cell death.

Direct quantification of cellular fluorescence intensity and enumeration of fluorescently labelled events, e.g., cell surface binding of peptide-dye conjugates may be conducted on an system (FMAT® 8100 HTS System, Applied Biosystems, Foster City, Calif.) that automates mix-and-read, non-radioactive assays with live cells or beads (Miraglia, "Homogeneous cell- and bead-based assays for high throughput screening using fluorometric microvolume assay technology", (1999) J. of Biomolecular Screening 4:193-204). Uses of labelled antibodies also include cell surface receptor binding assays, immunocapture assays, fluorescence linked immunosorbent assays (FLISA), caspase-cleavage (Zheng, "Caspase-3 controls both cytoplasmic and nuclear events associated with Fas-mediated apoptosis in vivo", (1998) Proc. Natl. Acad. Sci. USA 95:618-23; U.S. Pat. No. 6,372, 907), apoptosis (Vermes, "A novel assay for apoptosis. Flow cytometric detection of phosphatidylserine expression on early apoptotic cells using fluorescein labelled Annexin V" (1995) J. Immunol. Methods 184:39-51) and cytotoxicity assays. Fluorometric microvolume assay technology can be used to identify the up or down regulation by a molecule that is targeted to the cell surface (Swartzman, "A homogeneous and multiplexed immunoassay for high-throughput screening using fluorometric microvolume assay technology", (1999) Anal. Biochem. 271:143-51).

Labelled antibodies of the invention are useful as imaging biomarkers and probes by the various methods and techniques of biomedical and molecular imaging such as: (i) MRI (magnetic resonance imaging); (ii) MicroCT (computerized tomography); (iii) SPECT (single photon emission computed tomography); (iv) PET (positron emission tomography) Chen et al (2004) Bioconjugate Chem. 15:41-49; (v) bioluminescence; (vi) fluorescence; and (vii) ultrasound. Immunoscintigraphy is an imaging procedure in which antibodies labeled with radioactive substances are administered to an animal or human patient and a picture is taken of sites in the body where the antibody localizes (U.S. Pat. No. 6,528,624). Imaging biomarkers may be objectively measured and evaluated as an indicator of normal biological processes, pathogenic processes, or pharmacological responses to a therapeutic intervention.

Peptide labelling methods are well known. See Haugland, 2003, Molecular Probes Handbook of Fluorescent Probes and Research Chemicals, Molecular Probes, Inc.; Brinkley, 1992, Bioconjugate Chem. 3:2; Garman, (1997) Non-Radioactive Labelling: A Practical Approach, Academic Press, London; Means (1990) Bioconjugate Chem. 1:2; Glazer et al (1975) Chemical Modification of Proteins. Laboratory Techniques in Biochemistry and Molecular Biology (T. S. Work and E. Work, Eds.) American Elsevier Publishing Co., New York; Lundblad, R. L. and Noyes, C. M. (1984) Chemical Reagents for Protein Modification, Vols. I and II, CRC Press, New York; Pfleiderer, G. (1985) "Chemical Modification of Proteins", Modern Methods in Protein Chemistry, H. Tscheesche, Ed., Walter DeGryter, Berlin and New York; and Wong (1991) Chemistry of Protein Conjugation and Crosslinking, CRC Press, Boca Raton, Fla.); De Leon-Rodriguez et al (2004) Chem. Eur. J. 10:1149-1155; Lewis et al (2001) Bioconjugate Chem. 12:320-324; Li et al (2002) Bioconjugate Chem. 13:110-115; Mier et al (2005) Bioconjugate Chem. 16:240-237.

Peptides and proteins labelled with two moieties, a fluorescent reporter and quencher in sufficient proximity undergo fluorescence resonance energy transfer (FRET). Reporter groups are typically fluorescent dyes that are excited by light at a certain wavelength and transfer energy to an acceptor, or quencher, group, with the appropriate Stokes shift for emission at maximal brightness. Fluorescent dyes include molecules with extended aromaticity, such as fluorescein and rhodamine, and their derivatives. The fluorescent reporter may be partially or significantly quenched by the quencher moiety in an intact peptide. Upon cleavage of the peptide by a peptidase or protease, a detectable increase in fluorescence may be measured (Knight, C. (1995) "Fluorimetric Assays of Proteolytic Enzymes", Methods in Enzymology, Academic Press, 248:18-34).

The labelled antibodies of the invention may also be used as an affinity purification agent. In this process, the labelled antibody is immobilized on a solid phase such a Sephadex resin or filter paper, using methods well known in the art. The immobilized antibody is contacted with a sample containing the antigen to be purified, and thereafter the support is washed with a suitable solvent that will remove substantially all the material in the sample except the antigen to be purified, which is bound to the immobilized polypeptide variant. Finally, the support is washed with another suitable solvent, such as glycine buffer, pH 5.0, which will release the antigen from the polypeptide variant.

In some embodiments, the present invention provides anti-PD-L1 antibodies which may find use herein as therapeutic agents. Exemplary antibodies include polyclonal, monoclonal, chimeric, humanized, and human antibodies.

Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized For example, the antigen can be conjugated to keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl2$, or $R'N=C=NR$, where R and R1 are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later, the animals are boosted with ⅕ to 1/10 the original amount of peptide or conjugate in Freund's complete adjuvant by subcutaneous injection at multiple sites. Seven to 14 days later, the animals are bled and the serum is assayed for antibody titer. Animals are boosted until the titer plateaus. Conjugates also can be made in recombinant cell culture as protein fusions. Also, aggregating agents such as alum are suitably used to enhance the immune response.

Monoclonal Antibodies

A monoclonal antibody (mAb) to an antigen of interest can be prepared by using any technique known in the art. These include, but are not limited to, the hybridoma technique originally described by Kohler and Milstein (1975, Nature 256, 495-497), the human B cell hybridoma technique (Kozbor et al., 1983, Immunology Today 4:72), and the EBV-hybridoma technique (Cole et al., 1985, Monoclonal Antibodies and Cancer Therapy, Alan R. Liss, Inc., pp.

77-96). The Selected Lymphocyte Antibody Method (SLAM) (Babcook, J. S., et al., A novel strategy for generating monoclonal antibodies from single, isolated lymphocytes producing antibodies of defined specificities. Proc Natl Acad Sci USA, 1996. 93 (15): p. 7843-8.) and (McLean G R, Olsen O A, Watt I N, Rathanaswami P, Leslie K B, Babcook J S, Schrader J W. Recognition of human cytomegalovirus by human primary immunoglobulins identifies an innate foundation to an adaptive immune response. J Immunol. 2005 Apr. 15; 174(8):4768-78. Such antibodies may be of any immunoglobulin class including IgG, IgM, IgE, IgA, and IgD and any subclass thereof. The hybridoma producing the mAbs of use in this invention may be cultivated in vitro or in vivo.

Monoclonal antibodies can be made using the hybridoma method first described by Kohler et al., Nature, 256:495 (1975), or may be made by recombinant DNA methods (U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium which medium preferably contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8-653 cells available from the American Type Culture Collection, Manassas, Va., USA. Human myeloma and mouse-human heteromyeloma cell lines also have been described for the production of human monoclonal antibodies (Kozbor, J. Immunol., 133:3001 (1984); and Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., Anal. Biochem., 107:220 (1980).

Once hybridoma cells that produce antibodies of the desired specificity, affinity, and/or activity are identified, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal, e.g., by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., Curr. Opinion in Immunol., 5:256-262 (1993) and Pliickthun, Immunol. Revs. 130:151-188 (1992).

In a further embodiment, monoclonal antibodies or antibody fragments can be isolated from antibody phage libraries generated using the techniques described in McCafferty et al., Nature, 348:552-554 (1990). Clackson et al., Nature, 352:624-628 (1991) and Marks et al., J. Mol. Biol., 222: 581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res. 21:2265-2266 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain (CH and CO sequences for the homologous murine sequences (U.S. Pat. No. 4,816,567; and Morrison, et al., Proc. Natl. Acad. Sci. USA, 81:6851 (1984)), or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Chimeric, Humanized, and Human Antibodies

In some embodiments, an anti-PD-L1 antibody is a chimeric antibody. Certain chimeric antibodies are described, e.g., in U.S. Pat. No. 4,816,567; and Morrison et al., Proc. Natl. Acad. Sci. USA, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In some embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

An anti-PD-L1 antibody in accordance with embodiments of the invention can be a humanized or human antibody. Humanized forms of non-human (e.g., murine or rabbit) antibodies are chimeric immunoglobulins, immunoglobulin chains or fragments thereof (such as Fv, Fab, Fab', F(ab')2 or other antigen-binding subsequences of antibodies) which contain minimal sequences derived from non-human immunoglobulin. Humanized antibodies include human immunoglobulins (recipient antibody) in which residues from an HVR of the recipient are replaced by residues from an HVR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported HVR or framework sequences. In general, the humanized antibody will comprise substantially all of at least one, and typically two, variable domains, in which all or substantially all of the HVRs correspond to those of a non-human immunoglobulin and all or substantially all of the FR regions are those of a human immunoglobulin consensus sequence. The humanized antibody optimally also will comprise at least a portion of an immunoglobulin constant region (e.g., an Fc region), typically that of a human immunoglobulin (Jones et al., Nature, 321:522-525 (1986); Riechmann et al., Nature, 332:323-329 (1988); and Presta, Curr. Op. Struct. Biol., 2:593-596 (1992)).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent HVRs or HVR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some HVR residues and possibly some FR residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. Reduction or elimination of a HAMA response is a significant aspect of clinical development of suitable therapeutic agents. See, e.g., Khaxzaeli et al., J. Natl. Cancer Inst. (1988), 80:937; Jaffers et al., Transplantation (1986), 41:572; Shawler et al., J. Immunol. (1985), 135:1530; Sears et al., J. Biol. Response Mod. (1984), 3:138; Miller et al., Blood (1983), 62:988; Hakimi et al., J. Immunol. (1991), 147:1352; Reichmann et al., Nature (1988), 332:323; Junghans et al., Cancer Res. (1990), 50:1495. As described herein, the invention provides antibodies that are humanized such that HAMA response is reduced or eliminated. Variants of these antibodies can further be obtained using routine methods known in the art, some of which are further described below. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., J. Immunol. 151:2296 (1993); Chothia et al., J. Mol. Biol., 196:901 (1987)). Another method uses a particular framework region derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol. 151:2623 (1993)).

For example, an amino acid sequence from an antibody as described herein can serve as a starting (parent) sequence for diversification of the framework and/or hypervariable sequence(s). A selected framework sequence to which a starting hypervariable sequence is linked is referred to herein as an acceptor human framework. While the acceptor human frameworks may be from, or derived from, a human immunoglobulin (the VL and/or VH regions thereof), preferably the acceptor human frameworks are from, or derived from, a human consensus framework sequence as such frameworks have been demonstrated to have minimal, or no, immunogenicity in human patients.

Where the acceptor is derived from a human immunoglobulin, one may optionally select a human framework sequence that is selected based on its homology to the donor framework sequence by aligning the donor framework sequence with various human framework sequences in a collection of human framework sequences, and select the most homologous framework sequence as the acceptor.

While the acceptor may be identical in sequence to the human framework sequence selected, whether that be from a human immunoglobulin or a human consensus framework, the present invention contemplates that the acceptor sequence may comprise pre-existing amino acid substitutions relative to the human immunoglobulin sequence or human consensus framework sequence. These pre-existing substitutions are preferably minimal; usually four, three, two or one amino acid differences only relative to the human immunoglobulin sequence or consensus framework sequence.

In some embodiments, hypervariable region residues of a non-human antibody are incorporated into the VL and/or VH acceptor human frameworks. For example, one may incorporate residues corresponding to the Kabat CDR residues, the Chothia hypervariable loop residues, the Abm residues, and/or contact residues. Optionally, the extended hypervariable region residues as follows are incorporated: 24-34 (L1), 50-56 (L2) and 89-97 (L3), 26-35B (H1), 50-65, 47-65 or 49-65 (H2) and 93-102, 94-102, or 95-102 (H3).

While "incorporation" of hypervariable region residues is discussed herein, it will be appreciated that this can be achieved in various ways, for example, a nucleic acid encoding the desired amino acid sequence can be generated by mutating a nucleic acid encoding the mouse variable domain sequence so that the framework residues thereof are changed to acceptor human framework residues, or by mutating a nucleic acid encoding the human variable domain sequence so that the hypervariable domain residues are changed to non-human residues, or by synthesizing a nucleic acid encoding the desired sequence, etc.

As described herein, hypervariable region-grafted variants may be generated by Kunkel mutagenesis of nucleic acid encoding the human acceptor sequences, using a separate oligonucleotide for each hypervariable region. Kunkel et al., Methods Enzymol. 154:367-382 (1987). Appropriate changes can be introduced within the framework and/or hypervariable regions, using routine techniques, to correct and re-establish proper hypervariable region-antigen interactions.

Phage(mid) display (also referred to herein as phage display in some contexts) can be used as a convenient and fast method for generating and screening many different potential variant antibodies in a library generated by sequence randomization. However, other methods for making and screening altered antibodies are available to the skilled person.

Phage(mid) display technology has provided a powerful tool for generating and selecting novel proteins which bind to a ligand, such as an antigen. Using the techniques of phage(mid) display allows the generation of large libraries of protein variants which can be rapidly sorted for those sequences that bind to a target molecule with high affinity. Nucleic acids encoding variant polypeptides are generally fused to a nucleic acid sequence encoding a viral coat protein, such as the gene III protein or the gene VIII protein. Monovalent phagemid display systems where the nucleic acid sequence encoding the protein or polypeptide is fused to a nucleic acid sequence encoding a portion of the gene III protein have been developed. (Bass, S., Proteins, 8:309 (1990); Lowman and Wells, Methods: A Companion to Methods in Enzymology, 3:205 (1991)). In a monovalent phagemid display system, the gene fusion is expressed at low levels and wild type gene III proteins are also expressed so that infectivity of the particles is retained. Methods of generating peptide libraries and screening those libraries have been disclosed in many patents (e.g. U.S. Pat. Nos. 5,723,286, 5,432,018, 5,580,717, 5,427,908 and 5,498,530).

Libraries of antibodies or antigen binding polypeptides have been prepared in a number of ways including by altering a single gene by inserting random DNA sequences or by cloning a family of related genes. Methods for displaying antibodies or antigen binding fragments using phage(mid) display have been described in U.S. Pat. Nos. 5,750,373, 5,733,743, 5,837,242, 5,969,108, 6,172,197, 5,580,717, and 5,658,727. The library is then screened for expression of antibodies or antigen binding proteins with the desired characteristics.

Methods of substituting an amino acid of choice into a template nucleic acid are well established in the art, some of which are described herein. For example, hypervariable region residues can be substituted using the Kunkel method. See, e.g., Kunkel et al., Methods Enzymol. 154:367-382 (1987).

The sequence of oligonucleotides includes one or more of the designed codon sets for the hypervariable region residues to be altered. A codon set is a set of different nucleotide triplet sequences used to encode desired variant amino acids. Codon sets can be represented using symbols to designate particular nucleotides or equimolar mixtures of nucleotides as shown in below according to the IUB code. IUB Codes: G Guanine; A Adenine; T Thymine; C Cytosine; R (A or G); Y (C or T); M (A or C); K (G or T); S (C or G); W (A or T); H (A or C or T); B (C or G or T); V (A or C or G); D (A or G or T) H (A or C or T); N (A or C or G or T).

For example, in the codon set DVK, D can be nucleotides A or G or T; V can be A or G or C; and K can be G or T. This codon set can present 18 different codons and can encode amino acids Ala, Trp, Tyr, Lys, Thr, Asn, Lys, Ser, Arg, Asp, Glu, Gly, and Cys.

Oligonucleotide or primer sets can be synthesized using standard methods. A set of oligonucleotides can be synthesized, for example, by solid phase synthesis, containing sequences that represent all possible combinations of nucleotide triplets provided by the codon set and that will encode the desired group of amino acids. Synthesis of oligonucleotides with selected nucleotide "degeneracy" at certain positions is well known in that art. Such sets of nucleotides having certain codon sets can be synthesized using commercial nucleic acid synthesizers (available from, for example, Applied Biosystems, Foster City, Calif.), or can be obtained commercially (for example, from Life Technologies, Rockville, Md.). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a variable domain nucleic acid template and also can include restriction enzyme sites for cloning purposes.

In one method, nucleic acid sequences encoding variant amino acids can be created by oligonucleotide-mediated mutagenesis. This technique is well known in the art as described by Zoller et al. Nucleic Acids Res. 10:6487-6504 (1987). Briefly, nucleic acid sequences encoding variant amino acids are created by hybridizing an oligonucleotide set encoding the desired codon sets to a DNA template, where the template is the single-stranded form of the plasmid containing a variable region nucleic acid template sequence. After hybridization, DNA polymerase is used to synthesize an entire second complementary strand of the template that will thus incorporate the oligonucleotide primer, and will contain the codon sets as provided by the oligonucleotide set.

Generally, oligonucleotides of at least 25 nucleotides in length are used. An optimal oligonucleotide will have 12 to 15 nucleotides that are completely complementary to the template on either side of the nucleotide(s) coding for the mutation(s). This ensures that the oligonucleotide will hybridize properly to the single-stranded DNA template molecule. The oligonucleotides are readily synthesized using techniques known in the art such as that described by Crea et al., Proc. Nat'l. Acad. Sci. USA, 75:5765 (1978).

The DNA template is generated by those vectors that are either derived from bacteriophage M13 vectors (the commercially available M13 mp 18 and M13 mp 19 vectors are suitable), or those vectors that contain a single-stranded phage origin of replication as described by Viera et al., Meth. Enzymol., 153:3 (1987). Thus, the DNA that is to be mutated can be inserted into one of these vectors in order to generate single-stranded template. Production of the single-stranded template is described in sections 4.21-4.41 of Sambrook et al., above.

To alter the native DNA sequence, the oligonucleotide is hybridized to the single stranded template under suitable hybridization conditions. A DNA polymerizing enzyme, usually T7 DNA polymerase or the Klenow fragment of DNA polymerase I, is then added to synthesize the complementary strand of the template using the oligonucleotide as a primer for synthesis. A heteroduplex molecule is thus formed such that one strand of DNA encodes the mutated form of gene 1, and the other strand (the original template) encodes the native, unaltered sequence of gene 1. This heteroduplex molecule is then transformed into a suitable host cell, usually a prokaryote such as E. coli JM101. After growing the cells, they are plated onto agarose plates and screened using the oligonucleotide primer radiolabelled with a 32-Phosphate to identify the bacterial colonies that contain the mutated DNA.

The method described immediately above may be modified such that a homoduplex molecule is created wherein both strands of the plasmid contain the mutation(s). The modifications are as follows: The single stranded oligonucleotide is annealed to the single-stranded template as described above. A mixture of three deoxyribonucleotides, deoxyriboadenosine (dATP), deoxyriboguanosine (dGTP), and deoxyribothymidine (dTT), is combined with a modified thiodeoxyribocytosine called dCTP-(aS) (which can be obtained from Amersham). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell.

As indicated previously the sequence of the oligonucleotide set is of sufficient length to hybridize to the template nucleic acid and may also, but does not necessarily, contain restriction sites. The DNA template can be generated by those vectors that are either derived from bacteriophage M13 vectors or vectors that contain a single-stranded phage origin of replication as described by Viera et al. Meth. Enzymol., 153:3 (1987). Thus, the DNA that is to be mutated must be inserted into one of these vectors in order to generate single-stranded template. Production of the single-stranded template is described in sections 4.21-4.41 of Sambrook et al., supra.

According to another method, antigen binding may be restored during humanization of antibodies through the selection of repaired hypervariable regions (See application Ser. No. 11/061,841, filed Feb. 18, 2005). The method includes incorporating non-human hypervariable regions onto an acceptor framework and further introducing one or more amino acid substitutions in one or more hypervariable regions without modifying the acceptor framework sequence. Alternatively, the introduction of one or more amino acid substitutions may be accompanied by modifications in the acceptor framework sequence.

According to another method, a library can be generated by providing upstream and downstream oligonucleotide sets, each set having a plurality of oligonucleotides with different sequences, the different sequences established by the codon sets provided within the sequence of the oligonucleotides. The upstream and downstream oligonucleotide sets, along with a variable domain template nucleic acid sequence, can be used in a polymerase chain reaction to generate a "library" of PCR products. The PCR products can be referred to as "nucleic acid cassettes", as they can be fused with other related or unrelated nucleic acid sequences, for example, viral coat proteins and dimerization domains, using established molecular biology techniques.

The sequence of the PCR primers includes one or more of the designed codon sets for the solvent accessible and highly diverse positions in a hypervariable region. As described above, a codon set is a set of different nucleotide triplet sequences used to encode desired variant amino acids.

Antibody selectants that meet the desired criteria, as selected through appropriate screening/selection steps can be isolated and cloned using standard recombinant techniques.

It is further important that antibodies be humanized with retention of high binding affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of a humanized anti-PD-L1 antibody are contemplated. For example, the humanized antibody may be an antibody fragment, such as a Fab. Alternatively, the humanized antibody may be an intact antibody, such as an intact IgG, IgM or IgA antibody. In some embodiments, an intact antibody can be an intact IgM antibody.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice will result in the production of human antibodies upon antigen challenge.

See, e.g., Jakobovits et al., Proc. Natl. Acad. Sci. USA, 90:2551 (1993); Jakobovits et al., Nature, 362:255-258 (1993); Bruggemann et al., Year in Immuno. 7:33 (1993); U.S. Pat. Nos. 5,545,806, 5,569,825, 5,591,669 (all of GenPharm); U.S. Pat. No. 5,545,807; and WO 97/17852.

Alternatively, phage display technology (McCafferty et al., Nature 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S, and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

In some embodiments, the antibodies of this disclosure are human monoclonal antibodies. Such human monoclonal antibodies directed against PD-L1 can be generated using transgenic or transchromosomic mice carrying parts of the human immune system rather than the mouse system. These transgenic and transchromosomic mice include mice referred to herein as the HuMAb Mouse™ and KM Mouse™, respectively, and are collectively referred to herein as "human Ig mice."

The HuMAb Mouse™ (Medarex, Inc.) contains human immunoglobulin gene miniloci that encode un-rearranged human heavy (μ and γ) and κ light chain immunoglobulin sequences, together with targeted mutations that inactivate the endogenous μ and κ chain loci (see e.g., Lonberg, et al. (1994) Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal antibodies (Lonberg, N. et al. (1994), supra; reviewed in Lonberg, N. (1994) Handbook of Experimental Pharmacology 113:49-101; Lonberg, N. and Huszar, D. (1995) Intern. Rev. Immunol. 13: 65-93, and Harding, F. and Lonberg, N. (1995) Ann. N.Y. Acad. Sci. 764:536-546). Preparation and use of the HuMAb Mouse™, and the genomic modifications carried by such mice, is further described in Taylor, L. et al. (1992) Nucleic Acids Research 20:6287-6295; Chen, J. et al. (1993) International Immunology 5: 647-656; Tuaillon et al. (1993) Proc. Natl. Acad. Sci. USA 90:3720-3724; Choi et al. (1993) Nature Genetics 4:117-123; Chen, J. et al. (1993) EMBO J. 12: 821-830; Tuaillon et al., (1994) J. Immunol. 152:2912-2920; Taylor, L. et al. (1994) International Immunology 6: 579-591; and Fishwild, D. et al. (1996) Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In another embodiment, human antibodies in accordance with embodiments of this disclosure can be raised using a mouse that carries human immunoglobulin sequences on transgenes and trans-chromosomes, such as a mouse that carries a human heavy chain transgene and a human light chain trans-chromosome. This mouse is referred to herein as a "KM Mouse™" and is described in detail in PCT Publication WO 02/43478 to Ishida et al.

Still further, alternative transgenic animal systems expressing human immunoglobulin genes are available in the art and can be used to raise anti-PD-L1 antibodies of this disclosure. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise anti-PD-L1 antibodies of this disclosure. For example, mice carrying both a human heavy chain trans-chromosome and a human light chain trans-chromosome, referred to as "TC mice" can be used; such mice are described in Tomizuka et al. (2000) Proc. Natl. Acad. Sci. USA 97:722-727. Furthermore, cows carrying human heavy and light chain trans-chromosomes have been described in the art (e.g., Kuroiwa et al. (2002) Nature Biotechnology 20:889-894 and PCT application No. WO 2002/092812) and can be used to raise anti-PD-L1 antibodies of this disclosure.

Antibody Fragments

In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and scFv antibody fragments can all be expressed in and secreted from E. coli, thus allowing the facile production of large amounts of these fragments. Antibody fragments can be isolated from the antibody phage libraries discussed above. Alternatively, Fab'-SH fragments can be directly recovered from E. coli and chemically coupled to form F(ab')2 fragments (Carter et al., Bio/Technology 10:163-167 (1992)). According to another approach, F(ab')2 fragments can be isolated directly from recombinant host cell culture. Fab and F(ab')2 fragment with increased in vivo half-life comprising a salvage receptor binding epitope residues are described in U.S. Pat. No. 5,869,046. Other techniques for the production of antibody fragments will be apparent to the skilled practitioner. In other embodiments, the antibody of choice is a single chain Fv fragment (scFv or sFv). See WO 93/16185; U.S. Pat. Nos. 5,571,894; and 5,587,458. Fv and sFv are the only species with intact combining sites that are devoid of constant regions; thus, they are suitable for reduced non-specific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641,870 for example.

Bispecific and Multispecific Antibodies

As reviewed above, bispecific and multispecific antibodies are antibodies that have binding specificities for at least two different epitopes. Exemplary bispecific antibodies can bind to two different epitopes of a PD-L1 protein as described herein. Other such antibodies may combine a PD-L1 binding site with a binding site for another protein (e.g., a cell surface protein, e.g., a tumor antigen). Alternatively, an anti-PD-L1 binding unit can be combined with a binding unit that binds to a triggering molecule on a leukocyte, such as a T-cell receptor molecule (e.g., CD3), or Fc receptors for IgG (FcγR), such as FcγRI (CD64), FcγRII (CD32) and FcγRIII (CD16), so as to focus and localize cellular defense mechanisms to the PD-L1-expressing cell. In some embodiments, a bispecific antibody can comprise one binding unit that binds to PD-L1 and a second binding unit that binds to another binding target, e.g., a cell surface protein, such as a tumor antigen. Non-limiting examples of cell surface proteins that can serve as binding targets include: CD20, EGFR, HER2, CTLA-4, TIM3, LAG3, VISTA and TIGIT. The Genbank accession numbers corresponding to CTLA-4, TIM3, LAG3, VISTA and TIGIT can be found in Table 2. The amino acid sequence of human CD20 is provided in UniProtKB number P11836. The amino acid sequence of human EGFR is provided in UniProtKB number P00533. The amino acid sequence of human HER2 (human ERBB2) is provided in UniProtKB number P04626.

Bispecific antibodies may also be used to localize cytotoxic agents to cells which express PD-L1. These antibodies possess a PD-L1-binding unit and a binding unit that binds to the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., F(ab')2 bispecific antibodies).

Methods for making bispecific antibodies are known in the art. Traditional production of full length bispecific antibodies is based on the co-expression of two immunoglobulin heavy chain-light chain pairs, where the two chains have different specificities (Millstein et al., Nature 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J. 10:3655-3659 (1991).

Effector Function Engineering

It may be desirable to modify an antibody of the invention with respect to effector function, e.g., so as to enhance antigen-dependent cell-mediated cytotoxicity (ADCC) and/or complement dependent cytotoxicity (CDC) of the antibody. This may be achieved by introducing one or more amino acid substitutions in a heavy chain constant region (i.e., an Fc region) of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176:1191-1195 (1992) and Shopes, B. J. Immunol. 148:2918-2922 (1992). Homodimeric antibodies with enhanced anti-tumor activity may also be prepared using heterobifunctional cross-linkers as described in Wolff et al., Cancer Research 53:2560-2565 (1993). Alternatively, an antibody can be engineered to have an increased number of Fc regions (e.g., an IgG molecule engineered to have two or more Fc regions) and may thereby have enhanced complement lysis and ADCC capabilities. See Stevenson et al., Anti-Cancer Drug Design 3:219-230 (1989). To increase the serum half-life of an antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG1, IgG2, IgG3, or IgG4) that is responsible for increasing the in vivo serum half-life of a molecule that comprises the epitope (e.g., an IgG antibody).

Antibody Variants

In addition to the anti-PD-L1 antibodies described herein, it is contemplated that anti-PD-L1 antibody variants can be prepared. Anti-PD-L1 antibody variants can be prepared by introducing appropriate nucleotide changes into the encoding DNA, and/or by synthesis of the desired antibody or polypeptide. Those skilled in the art will appreciate that amino acid changes may alter post-translational processes of the anti-PD-L1 antibody, such as changing the number or position of glycosylation sites or altering the membrane anchoring characteristics.

Variations in the anti-PD-L1 antibodies described herein can be made, for example, using any of the techniques and guidelines for conservative and non-conservative mutations set forth, for instance, in U.S. Pat. No. 5,364,934. Variations may be a substitution, deletion or insertion of one or more codons encoding the antibody or polypeptide that results in a change in the amino acid sequence as compared with the native sequence antibody or polypeptide. Optionally, the variation is by substitution of at least one amino acid with any other amino acid in one or more of the domains of the anti-PD-L1 antibody. Guidance in determining which amino acid residue may be inserted, substituted or deleted without adversely affecting the desired activity may be found by comparing the sequence of the anti-PD-L1 antibody with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

Anti-PD-L1 antibody fragments are provided herein. Such fragments may be truncated at the N-terminus or C-terminus, or may lack internal residues, for example, when compared with a full length native antibody or protein.

Certain fragments may lack amino acid residues that are not essential for a desired biological activity of the anti-PD-L1 antibody.

Anti-PD-L1 antibody fragments may be prepared by any of a number of conventional techniques. Desired peptide fragments may be chemically synthesized. An alternative approach involves generating antibody or polypeptide fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired antibody or polypeptide fragment, by polymerase chain reaction (PCR). Oligonucleotides that define the desired termini of the DNA fragment are employed at the 5' and 3' primers in the PCR. Preferably, anti-PD-L1 antibody fragments share at least one biological and/or immunological activity with the full length anti-PD-L1 antibodies disclosed herein.

In particular embodiments, conservative substitutions of interest are shown in Table 4 under the heading of preferred substitutions. If such substitutions result in a change in biological activity, then more substantial changes, denominated exemplary substitutions in Table 4, or as further described below in reference to amino acid classes, are introduced and the products screened.

TABLE 4

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of an anti-PD-L1 antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis (Carter et al., Nucl. Acids Res., 13:4331 (1986); Zoller et al., Nucl. Acids Res., 10:6487 (1987)), cassette mutagenesis (Wells et al., Gene, 34:315 (1985)), restriction selection mutagenesis (Wells et al., Philos. Trans. R. Soc. London SerA, 317:415 (1986)) or other known techniques can be performed on the cloned DNA to produce the anti-PD-L1 antibody variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant (Cunningham and Wells, Science, 244:1081-1085 (1989)). Alanine is also typically preferred because it is the most common amino acid. Further, it is frequently found in both buried and exposed positions (Creighton, The Proteins, (W.H. Freeman & Co., N.Y.); Chothia, J. Mol. Biol., 150:1 (1976)). If alanine substitution does not yield adequate amounts of variant, an isoteric amino acid can be used.

Any cysteine residue not involved in maintaining the proper conformation of the anti-PD-L1 antibody also may be substituted, generally with serine, to improve the oxidative stability of the molecule and prevent aberrant crosslinking. Conversely, cysteine bond(s) may be added to the anti-PD-L1 antibody to improve its stability (particularly where the antibody is an antibody fragment such as an Fv fragment).

A particularly preferred type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino acid substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and PD-L1 polypeptide. Such contact residues and neighboring residues are candidates for substitution according to the techniques provided herein. Once such variants are generated, the panel of variants is subjected to screening as described herein and antibodies with superior properties in one or more relevant assays may be selected for further development.

Nucleic acid molecules encoding amino acid sequence variants of an anti-PD-L1 antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-PD-L1 antibody.

Antibody Modifications

Covalent modifications of anti-PD-L1 antibodies are included within the scope of this invention. One type of covalent modification includes reacting targeted amino acid residues of an anti-PD-L1 antibody with an organic derivatizing agent that is capable of reacting with selected side chains or the N- or C-terminal residues of the anti-PD-L1 antibody. Derivatization with bifunctional agents is useful, for instance, for crosslinking anti-PD-L1 antibody to a water-insoluble support matrix or surface for use in the method for purifying anti-PD-L1 antibodies, and vice-versa. Commonly used crosslinking agents include, e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification of the anti-PD-L1 antibody included within the scope of this invention comprises altering the native glycosylation pattern of the antibody or polypeptide. "Altering the native glycosylation pattern" is intended for purposes herein to mean deleting one or more carbohydrate moieties found in native sequence anti-PD-L1 antibody (either by removing the underlying glycosylation site or by deleting the glycosylation by chemical and/or enzymatic means), and/or adding one or more glycosylation sites that are not present in the native sequence anti-PD-L1 antibody. In addition, the phrase includes qualitative changes in the glycosylation of the native proteins, involving a change in the nature and proportions of the various carbohydrate moieties present.

Glycosylation of antibodies and other polypeptides is typically either N-linked or 0-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. 0-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to an anti-PD-L1 antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original anti-PD-L1 antibody (for O-linked glycosylation sites). The anti-PD-L1 antibody amino acid sequence may optionally be altered through changes at the DNA level, particularly by mutating the DNA encoding the anti-P-L1 antibody at preselected bases such that codons are generated that will translate into the desired amino acids.

Another means of increasing the number of carbohydrate moieties on an anti-PD-L1 antibody is by chemical or enzymatic coupling of glycosides to the polypeptide. Such methods are described in the art, e.g., in WO 87/05330 published 11 Sep. 1987, and in Aplin and Wriston, CRC Crit. Rev. Biochem., pp. 259-306 (1981).

Removal of carbohydrate moieties present on an anti-PD-L1 antibody may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo- and exo-glycosidases as described by Thotakura et al., Meth. Enzymol. 138:350 (1987).

Immunoconjugates

Aspects of the invention include immunoconjugates (interchangeably referred to as "antibody-drug conjugates," or "ADCs") comprising an antibody (as described herein) conjugated to a cytotoxic agent, such as a chemotherapeutic agent, a growth inhibitory agent, a toxin (e.g., an enzymatically active toxin of bacterial, fungal, plant, or animal origin, or fragments thereof), or a radioactive isotope (i.e., a radioconjugate). Non-limiting examples of toxins include those described in WO 2014144871 and in U.S. Pat. No. 8,466, 260, the disclosures of which are herein incorporated by reference in their entirety. An immunoconjugate or "ADC" in accordance with embodiments of the invention may be of Formula I, below, wherein an antibody is conjugated (i.e., covalently attached) to one or more drug moieties (D) through an optional linker (L). ADCs may include thioMAb drug conjugates ("TDC").

Accordingly, an antibody may be conjugated to a drug either directly or via a linker. In Formula I, p is the average number of drug moieties per antibody, which can range, e.g., from about 1 to about 20 drug moieties per antibody, and in certain embodiments, from 1 to about 8 drug moieties per antibody. Aspects of the invention include a composition comprising a mixture of antibody-drug compounds of Formula I, where the average drug loading per antibody is about 2 to about 5, or about 3 to about 4.

A linker may comprise one or more linker components. Exemplary linker components include those described in U.S. Pat. No. 8,466,260, the disclosure of which is herein incorporated by reference in its entirety. Linker components, including stretcher, spacer, and amino acid units, may be synthesized by methods known in the art, such as those described in U.S. 2005/0238649 A1, the disclosure of which is herein incorporated by reference in its entirety. Additional non-limiting examples of linkers include those described in WO 2015095953, the disclosure of which is herein incorporated by reference in its entirety.

Immunoconjugates containing maytansinoids, methods of making the same, and their therapeutic use are disclosed, for example, in Erickson, et al (2006) Cancer Res. 66(8):4426-4433; U.S. Pat. Nos. 5,208,020, 5,416,064, US 2005/0276812 A1, and European Patent EP 0 425 235 B1, the disclosures of which are hereby expressly incorporated by reference.

In some embodiments, an immunoconjugate comprises an antibody conjugated to a dolastatin or a dolastatin peptidic analog or derivative, e.g., an auristatin (U.S. Pat. Nos. 5,635,483 and 5,780,588, the disclosures of which are incorporated herein in their entirety).

In some embodiments, an immunoconjugate comprises an antibody conjugated to one or more calicheamicin molecules. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company), the disclosures of which are incorporated herein in their entirety.

Other antitumor agents that can be conjugated to an antibody include BCNU, streptozocin, vincristine and 5-fluorouracil, the family of agents known collectively as the LL-E33288 complex, described in U.S. Pat. Nos. 5,053,394, 5,770,710, as well as esperamicins, described in U.S. Pat. No. 5,877,296, the disclosures of which are herein incorporated by reference in their entirety.

Pharmaceutical Formulations

The anti-PD-L1 compositions of the invention (e.g., anti-PD-L1 antibodies, antigen-binding fragments of anti-PD-L1 antibodies, or ADCs, as described herein) may be administered by any route that is appropriate for the condition to be treated. Typically, administration is accomplished parenterally, i.e. via infusion, subcutaneous, intramuscular, intravenous, intradermal, intrathecal and/or epidural administration.

In one embodiment, a composition is administered via intravenous infusion. The dosage administered via infusion is in the range of about 1 $\mu g/m^2$ to about 10,000 $\mu g/m^2$ per dose, generally one dose per week for a total of one, two, three or four doses. In some embodiments, the dosage ranges from about 1 $\mu g/m^2$ to about 1,000 $\mu g/m^2$, about 1 $\mu g/m^2$ to about 800 $\mu g/m^2$, about 1 $\mu g/m^2$ to about 600 $\mu g/m^2$, about 1 $\mu g/m^2$ to about 400 $\mu g/m^2$, about 1 $\mu g/m^2$ to about 200 $\mu g/m^2$, or about 1 $\mu g/m^2$ to about 100 $\mu g/m^2$. In some embodiments, the dosage ranges from about 10 $\mu g/m^2$ to about 500 $\mu g/m^2$, about 10 $\mu g/m^2$ to about 300 $\mu g/m^2$, or about 10 $\mu g/m^2$ to about 200 $\mu g/m^2$.

In some embodiments, a dose is administered once per day, once per week, multiple times per week, but less frequently than once per day, multiple times per month but less frequently than once per day, multiple times per month but less frequently than once per week, once per month, once every other month, once every three months, once every six months, once every year, or intermittently to relieve or alleviate symptoms of the disease. Administration may continue at any of the disclosed intervals until remission of the tumor or symptoms of the cancer being treated. Administration may continue after remission or relief of symptoms is achieved where such remission or relief is prolonged by such continued administration.

In one aspect, the invention provides pharmaceutical formulations comprising at least one anti-PD-L1 composition of the invention. In some embodiments, a pharmaceutical formulation comprises (1) an anti-PD-L1 composition of the invention, and (2) a pharmaceutically-acceptable carrier.

Therapeutic formulations comprising an anti-PD-L1 antibody used in accordance with the present invention are prepared for storage by mixing the antibody having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g., Zn-protein complexes); and/or non-ionic surfactants such as TWEEN®, PLURONICS® or polyethylene glycol (PEG). Pharmaceutical formulations to be used for in vivo administration are generally sterile. This is readily accomplished by filtration through sterile filtration membranes.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. Ed. (1980).

Sustained-release preparations may be prepared. Suitable examples of sustained-release preparations include semipermeable matrices of solid hydrophobic polymers containing an anti-PD-L1 composition, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated immunoglobulins remain in the body for extended periods of time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S-S bond formation through thio-disulfide interchange, stabilization may be achieved by modifying sulfhydryl residues, lyophilizing from acidic solutions, controlling moisture content, using appropriate additives, and developing specific polymer matrix compositions.

An anti-PD-L1 composition may be formulated in any suitable form for delivery to a target cell/tissue. For example, antibodies may be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., Proc. Natl. Acad. Sci. USA 82:3688 (1985); Hwang et al., Proc. Natl Acad. Sci. USA 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem. 257:286-288 (1982) via a disulfide interchange reaction. A chemotherapeutic agent is optionally contained within the liposome. See Gabizon et al., J. National Cancer Inst. 81(19):1484 (1989).

The formulations to be used for in vivo administration must be sterile. This is readily accomplished by filtration through sterile filtration membranes.

Articles of Manufacture and Kits

Aspects of the invention include articles of manufacture containing materials useful for the treatment, prevention and/or diagnosis of a disease or disorder that is mediated by PD-L1, e.g., a PD-L1-expressing cancer. An article of manufacture comprises a container and a label or package insert on or associated with the container. Suitable containers include, for example, bottles, vials, syringes, etc. The containers may be formed from a variety of materials such as glass or plastic. The container holds a composition which is effective for treating, preventing and/or diagnosing the disease or disorder and may have a sterile access port (for example the container may be an intravenous solution bag or a vial having a stopper pierceable by a hypodermic injection needle). At least one active agent in the composition is an anti-PD-L1 composition of the invention. The label or package insert indicates that the composition is used for treating the disease or disorder. The label or package insert will further comprise instructions for administering the antibody composition to the patient. Additionally, the article of manufacture may further comprise a second container comprising a pharmaceutically-acceptable buffer, such as bacteriostatic water for injection (BWFI), phosphate-buffered saline, Ringer's solution or dextrose solution. It may further include other materials desirable from a commercial and user standpoint, including other buffers, diluents, filters, needles, and syringes.

Kits are also provided that are useful for various purposes, e.g., for PD-L1-expressing cell killing assays, or for purification or immunoprecipitation of PD-L1 polypeptide from cells. For isolation and purification of PD-L1 polypeptide, a kit can contain an anti-PD-L1 antibody coupled to beads (e.g., sepharose beads). Kits can be provided which contain the antibodies for detection and quantitation of PD-L1 polypeptide in vitro, e.g., in an ELISA or a Western blot. As with the article of manufacture, the kit comprises a container and a label or package insert on or associated with the container. The container holds a composition comprising at least one anti-PD-L1 antibody, or antigen-binding fragment thereof, of the invention. Additional containers may be included that contain, e.g., diluents, buffers, and/or control antibodies. The label or package insert may provide a description of the composition as well as instructions for the intended in vitro or detection use.

Methods of Use

Aspects of the invention include methods of using one or more anti-PD-L1 compositions (e.g., anti-PD-L1 antibodies, antigen-binding fragments of anti-PD-L1 antibodies, or ADCs), as described herein, in the treatment, prevention and/or diagnosis of a disease or condition that is mediated at least in part by PD-L1 (e.g., by an interaction between PD-1 and PD-L1), including but not limited to the treatment of various cancers and immune diseases. Non-limiting example uses are described in further detail below.

A. Therapeutic Methods

An anti-PD-L1 composition of the invention may be used in, for example, in vitro, ex vivo, and in vivo therapeutic methods. In one aspect, the invention provides methods for inhibiting an interaction between a PD-L1 protein and one or more receptors or ligands (e.g., a PD-1 protein). In one aspect, the invention provides methods for inhibiting cell growth or proliferation, either in vivo or in vitro, the method comprising contacting a cell with an anti-PD-L1 composition under conditions permissive for binding of an anti-PD-L1 antibody, or antigen-binding fragment thereof, in the composition to PD-L1. "Inhibiting cell growth or proliferation" means decreasing a cell's growth or proliferation by at least about 10%, 20%, 30%, 40%, 50%, 60%, 70%, 80%, 90%, 95%, or up to 100%, and includes inducing cell death. In certain embodiments, the cell is a tumor cell. An anti-PD-L1 composition in accordance with embodiments of the invention may: (i) inhibit interaction between a PD-L1 protein and a receptor or ligand to which the PD-L1 protein is capable of binding (e.g., a PD-1 protein); (ii) inhibit tumor metastasis in vivo; (iii) inhibit tumor growth in vivo; (iv) decrease tumor size in vivo; (v) exhibit cytotoxic activity on a tumor cell expressing PD-L1 in vivo; or (vi) exhibit cytostatic activity on a tumor cell expressing PD-L1 in vivo. In some aspects, an anti-PD-L1 composition can bind to a PD-L1 protein and thereby inhibit one or more functions of a PD-1 protein (e.g., inhibit one or more immunosuppressive functions of a PD-1 protein). Accordingly, in some aspects, the subject therapeutic methods of use involve contacting a PD-L1 protein with an anti-PD-L1 antibody, or antigen-binding fragment, as described herein, thereby inhibiting one or more functions (e.g., one or more immunosuppressive functions) of a PD-1 protein.

Aspects of the invention include methods of inhibiting an interaction between a PD-1 protein and a PD-L1 protein by contacting the PD-L1 protein with an anti-PD-L1 antibody as described herein. In some embodiments, the method is carried out in vivo by administering an effective amount of an anti-PD-L1 antibody to a subject in need of therapy to inhibit an interaction between a PD-1 protein and a PD-L1 protein in the subject.

In one aspect, an anti-PD-L1 composition of the invention is used to treat or prevent a cell proliferative disorder, such as cancer. Examples of cancer types include, without limitation, acute lymphoblastic leukemia, acute myelogenous leukemia, biliary cancer, breast cancer (e.g., triple negative breast cancer, hormone receptor negative breast cancer), cervical cancer, chronic lymphocytic leukemia, chronic myelogenous leukemia, colorectal cancer, endometrial cancer, esophageal, gastric, head and neck cancer, nasopharyngeal cancer, Hodgkin's lymphoma, lung cancer (e.g., non-small-cell lung cancer), medullary thyroid cancer, non-Hodgkin's lymphoma, multiple myeloma, renal cancer, ovarian cancer, pancreatic cancer, glioma, melanoma, liver cancer, prostate cancer, urinary bladder cancer, melanoma and glioblastoma.

In some aspects, a cancer is an epithelial cancer. Epithelial cancers that are suitable for treatment with the subject anti-PD-L1 compositions include, without limitation, non-small-cell lung, urinary bladder, renal, liver, colorectal, ovarian, gastric, esophageal, pancreatic, thyroid, breast cancer (e.g., hormone receptor negative breast cancer, or triple negative breast cancer), and nasopharyngeal cancer.

In some aspects, a cancer is a hematologic cancer. Hematologic cancers that are suitable for treatment with the subject anti-PD-L1 compositions include, without limitation, leukemia, lymphoma, myeloma, myelodysplastic syndrome, acute myeloid leukemia, acute lymphoblastic leukemia, chronic myelogenous leukemia, chronic lymphocytic leukemia, Hodgkin's lymphoma and non-Hodgkin's lymphoma.

In some aspects, a cancer is a melanoma or a glioblastoma.

In one preferred embodiment, the cancer is a melanoma. In one preferred embodiment, the cancer is renal cancer. In one preferred embodiment, the cancer is urinary bladder cancer. In one preferred embodiment, the cancer is lung cancer. In one preferred embodiment, the cancer is non-small-cell lung cancer. In one preferred embodiment, the cancer is small-cell lung cancer.

In one aspect, the invention provides methods for treating a cell proliferative disorder comprising administering to an individual an effective amount of an anti-PD-L1 composition. In some embodiments, an anti-PD-L1 composition can be administered to a non-human mammal expressing PD-L1 with which the antibody cross-reacts (e.g., a primate, pig, rat, or mouse) for veterinary purposes or as an animal model of human disease. Regarding the latter, such animal models may be useful for evaluating the therapeutic efficacy of anti-PD-L1 compositions of the invention (e.g., testing of dosages and time courses of administration).

An anti-PD-L1 composition of the invention (as well as any additional therapeutic agent or adjuvant) can be administered by any suitable means, including parenteral, subcutaneous, intraperitoneal, intrapulmonary, and intranasal, and, if desired for local treatment, intra-lesional administration. Parenteral infusions include intramuscular, intravenous, intra-arterial, intraperitoneal, or subcutaneous administration. In addition, an anti-PD-L1 composition can be suitably administered by pulse infusion, particularly with declining doses of the composition. Dosing can be by any suitable route, e.g., by injections, such as intravenous or subcutaneous injections, depending in part on whether the administration is brief or chronic.

Anti-PD-L1 compositions in accordance with embodiments of the invention are generally formulated, dosed, and administered in a manner consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

Methods of Screening

Aspects of the invention include methods of determining the presence of a PD-L1 polypeptide in a sample suspected of containing the PD-L1 polypeptide, wherein the method comprises contacting the sample with an antibody that binds to the PD-L1 polypeptide and determining binding of the antibody to the PD-L1 polypeptide in the sample, wherein the presence of such binding is indicative of the presence of the PD-L1 polypeptide in the sample. Optionally, the sample may contain cells (e.g., cancer cells) suspected of expressing a PD-L1 polypeptide. The antibody employed in the method may optionally be detectably labeled, attached to a solid support, or the like.

Another embodiment of the present invention is directed to a method of diagnosing the presence of a tumor in a mammal, wherein the method comprises (a) contacting a test sample comprising cells obtained from the mammal with an antibody that binds to a PD-L1 polypeptide and (b) detecting the formation of a complex between the antibody and the PD-L1 polypeptide in the test sample, wherein the formation of a complex is indicative of the presence of a tumor that expresses PD-L1 in the mammal. Optionally, the antibody is detectably labeled, attached to a solid support, or the like, and/or the test sample is obtained from an individual suspected of having a cancerous tumor. Antibody detection can be achieved via different techniques as described herein, e.g., IHC and PET imaging.

Activity Assays

Anti-PD-L1 compositions in accordance with embodiments of the invention can be utilized in various assays known in the art. In one aspect, an anti-PD-L1 composition can be used in a biological activity assay. A biological activity assay can measure, e.g., the ability of an anti-PD-L1 composition to inhibit cell growth or proliferation (e.g., "cell killing" activity), or the ability to induce cell death, including programmed cell death (apoptosis).

In certain embodiments, an anti-PD-L1 composition can be used in an in vitro assay to measure inhibition of cell growth or proliferation. Assays for inhibition of cell growth or proliferation are well known in the art. Certain assays for cell proliferation, exemplified by the "cell killing" assays described herein, measure cell viability. One such assay is the CellTiter-Glo™ Luminescent Cell Viability Assay, which is commercially available from Promega (Madison, Wis.). That assay determines the number of viable cells in culture based on quantitation of ATP present, which is an indication of metabolically active cells. See Crouch et al (1993) J. Immunol. Meth. 160:81-88, U.S. Pat. No. 6,602, 677. The assay may be conducted in 96- or 384-well format, making it amenable to automated high-throughput screening (HTS). See Cree et al (1995) AntiCancer Drugs 6:398-404. The assay procedure involves adding a single reagent (Cell-Titer-Glo® Reagent) directly to cultured cells. This results in cell lysis and generation of a luminescent signal produced by a luciferase reaction. The luminescent signal is proportional to the amount of ATP present, which is directly proportional to the number of viable cells present in culture. Data can be recorded by luminometer or CCD camera imaging device. The luminescence output is expressed as relative light units (RLU).

Another assay for cell proliferation is the "MTT" assay, a colorimetric assay that measures the oxidation of 3-(4,5-dimethylthiazol-2-yl)-2,5-diphenyltetrazolium bromide to formazan by mitochondrial reductase. Like the CellTiter-Glo™ assay, this assay indicates the number of metabolically active cells present in a cell culture. See, e.g., Mosmann (1983) J. Immunol. Meth. 65:55-63, and Zhang et al. (2005) Cancer Res. 65:3877-3882.

In one aspect, an anti-PD-L1 composition can be utilized in an assay to measure its ability to induce cell death in vitro. Assays for induction of cell death are well known in the art. In some embodiments, such assays measure, e.g., loss of membrane integrity as indicated by uptake of propidium iodide (PI), trypan blue (see Moore et al. (1995) Cytotechnology, 17:1-11), or 7AAD. In an exemplary PI uptake assay, cells are cultured in Dulbecco's Modified Eagle Medium (D-MEM):Ham's F-12 (50:50) supplemented with 10% heat-inactivated FBS (Hyclone) and 2 mM L-glutamine. Thus, the assay is performed in the absence of complement and immune effector cells. Cells are seeded at a density of $3 \times 10^6$ per dish in 100×20 mm dishes and allowed to attach overnight. The medium is removed and replaced with fresh medium alone or medium containing various concentrations of the anti-PD-L1 composition. The cells are incubated for a 3-day time period. Following treatment, monolayers are washed with PBS and detached by trypsinization. Cells are then centrifuged at 1200 rpm for 5 minutes at 4° C., the pellet re-suspended in 3 ml cold $Ca^{2+}$ binding buffer (10 mM Hepes, pH 7.4, 140 mM NaCl, 2.5 mM $CaCl_2$) and aliquoted into 35 mm strainer-capped 12×75 mm tubes (1 ml per tube, 3 tubes per treatment group) for removal of cell clumps. Tubes then receive PI (10 μg/ml). Samples are analyzed using a FACSCAN™ flow cytometer and FACSCONVERT™ CellQuest software (Becton Dickinson). Anti-PD-L1 compositions that induce statistically significant levels of cell death as determined by PI uptake are thus identified.

In one aspect, an anti-PD-L1 composition can be tested for its ability to induce apoptosis (programmed cell death) in vitro. An exemplary assay for antibodies that induce apoptosis is an annexin binding assay. In an exemplary annexin binding assay, cells are cultured and seeded in dishes as discussed in the preceding paragraph. The medium is removed and replaced with fresh medium alone or medium containing 0.001 to 10 μg/ml of the antibody. Following a three-day incubation period, monolayers are washed with PBS and detached by trypsinization. Cells are then centrifuged, resuspended in $Ca^{2+}$ binding buffer, and aliquoted into tubes as discussed in the preceding paragraph. Tubes then receive labeled annexin (e.g. annexin V-FITC) (1 μg/ml). Samples are analyzed using a FACSCAN™ flow cytometer and FACSCONVERT™ CellQuest software (BD Biosciences). Antibodies that induce statistically significant levels of annexin binding relative to control are thus identified. Another exemplary assay for antibodies that induce apoptosis is a histone DNA ELISA colorimetric assay for detecting inter-nucleosomal degradation of genomic DNA. Such an assay can be performed using, e.g., the Cell Death Detection ELISA kit (Roche, Palo Alto, Calif.).

Cells for use in any of the above in vitro assays include cells or cell lines that naturally express PD-L1 or that have been engineered to express PD-L1. Such cells include tumor cells that express or overexpress PD-L1 relative to normal cells of the same tissue origin. Such cells also include cell lines (including tumor cell lines) that express PD-L1 and cell lines that do not normally express PD-L1 but have been transfected with nucleic acid encoding PD-L1.

In one aspect, an anti-PD-L1 composition is tested for its ability to inhibit cell growth or proliferation in vivo. In certain embodiments, an anti-PD-L1 composition is tested for its ability to inhibit tumor growth in vivo. In vivo model systems, such as xenograft models, can be used for such testing. In an exemplary xenograft system, human tumor cells are introduced into a suitably immunocompromised non-human animal, e.g., a SCID mouse. An anti-PD-L1 composition of the invention is administered to the animal. The ability of the anti-PD-L1 composition to inhibit or decrease tumor growth is measured. In certain embodiments of the above xenograft system, the human tumor cells are tumor cells from a human patient. In certain embodiments, the human tumor cells are introduced into a suitably immunocompromised non-human animal by subcutaneous injection or by transplantation into a suitable site, such as a mammary fat pad.

Binding Assays and Other Assays

Aspects of the invention include methods of inhibiting an interaction between a PD-1 protein and a PD-L1 protein by contacting the PD-L1 protein with an anti-PD-L1 antibody as described herein. In some embodiments, the method is carried out in vitro.

In one aspect, an anti-PD-L1 antibody is tested for its antigen binding activity. For example, in certain embodiments, an anti-PD-L1 antibody is tested for its ability to bind to PD-L1 expressed on the surface of a cell, e.g., a tumor cell. A FACS assay may be used for such testing.

In one aspect, competition assays can be used to identify one or more antibodies (e.g., one or more monoclonal antibodies) that compete with a monoclonal antibody described herein for binding to PD-L1. In certain embodiments, such a competing antibody binds to the same epitope (e.g., a linear or a conformational epitope) that is bound by a monoclonal antibody described herein. Exemplary competition assays include, but are not limited to, routine assays such as those provided in Harlow and Lane (1988) Antibodies: A Laboratory Manual ch. 14 (Cold Spring Harbor Laboratory, Cold Spring Harbor, N.Y.). Detailed exemplary methods for mapping an epitope to which an antibody binds are provided in Morris (1996) "Epitope Mapping Protocols," in Methods in Molecular Biology vol. 66 (Humana Press, Totowa, N.J.). Two antibodies are said to bind to the same epitope if each blocks binding of the other by 50% or more.

In an exemplary competition assay, immobilized PD-L1 is incubated in a solution comprising a first labeled antibody that binds to PD-L1 (e.g., a monoclonal antibody described herein) and a second unlabeled antibody that is being tested for its ability to compete with the first antibody for binding to PD-L1. The second antibody may be present in a hybridoma supernatant. As a control, immobilized PD-L1 is incubated in a solution comprising the first labeled antibody but not the second unlabeled antibody. After incubation under conditions permissive for binding of the first antibody to PD-L1, excess unbound antibody is removed, and the amount of label associated with immobilized PD-L1 is measured. If the amount of label associated with immobilized PD-L1 is substantially reduced in the test sample relative to the control sample, then that indicates that the second antibody is competing with the first antibody for binding to PD-L1. In certain embodiments, immobilized PD-L1 is present on the surface of a cell or in a membrane preparation obtained from a cell expressing PD-L1 on its surface.

In one aspect, purified anti-PD-L1 antibodies can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

The following examples are offered for illustrative purposes only, and are not intended to limit the scope of the present invention in any way. While several embodiments have been provided in the present disclosure, it should be understood that the disclosed systems and methods might be embodied in many other specific forms without departing from the spirit or scope of the present disclosure. The present examples are to be considered as illustrative and not restrictive, and the intention is not to be limited to the details given herein. Various examples of changes, substitutions, and alterations are ascertainable by one skilled in the art and could be made without departing from the spirit and scope disclosed herein.

All references cited throughout the specification are expressly incorporated by reference herein.

EXAMPLES

Example 1: Murine Hybridoma Generation and Screening 1.1 Immunization protocol and schedule:

Recombinant fusion proteins that included an extracellular portion of i) human PD-L1 with a HIS tag (Sino Bio, cat#10084-H084) and ii) Cynomolgus PD-L1 with a HIS tag Sino Bio, cat#90251-C08H) were utilized as antigens in an immunization protocol. To generate fully human monoclonal antibodies to PD-L1, three different strains of mice were immunized and screened. Balb/C (3), C57/Black 6 (3) and Swiss Webster (3) were immunized six times with alternating proteins (human and cyno PD-L1) on day 0, 7, 14, 21, 28 and 35. The first immunization was dosed at 50 ug of the proteins and the subsequent immunizations were dosed at 25 ug. A subcutaneous administration of the antigen was done with adjuvant MagicMouse near the left and right inguinal lymph nodes, left and right brachial lymph nodes and left and right axial lymph nodes at 50 uL/site. Blood was taken from all 9 mice on day 0 prior to the first immunization (pre-bleed) and day 42 to evaluate serum titers for the antibody response. The serum was screened by ELISA (described below), and mice with sufficient titers of anti-human-PD-L1 immunoglobulins were used for fusions. Mice were boosted intravenously with recombinant human PD-L1 3 days prior to sacrifice and removal of spleens.

1.2 Generation of Hybridomas Producing Human Monoclonal Antibodies to PD-L1.

Mouse splenocytes isolated from a Swiss Webster mouse were fused with a mouse myeloma cell line following standard protocols. The resulting hybridomas were then screened for the production of antigen-specific antibodies.

Single cell suspension of splenocytes from an immunized Swiss Webster mouse were fused to Sp2/0 cells, a non-secretory mouse myeloma cell line, with PEG. Cells were plated at ~1×10$^5$/well in a flat bottom 96 well sterile microtiter plate followed by 2 weeks selection with 1×HAT in complete DMEM-F12, 10% FBS, Glutamax, Sodium Pyruvate, HEPES, Non Essential Amino Acids and Penn/Strep. After two weeks the cells were cultured in media where the HAT selection was replaced with HT. Individual wells were then screened by ELISA (described below) for anti-human PD-L1 monoclonal IgG and IgM antibodies. The antibody secreting hybridomas were re-plated and screened again to check if they were still positive for anti-human PD-L1 IgG or IgM. Anti-human PD-L1 antibodies were then subcloned by limiting dilution. The stable clones were weaned off HT media into DMEM-F12+10% FBS+Glutamax+Pen Strep and cultured to generate small amounts of antibody for further characterization. Hybridomas were also frozen down in 10% DMSO 90% FBS.

1.3 Detection of Murine IgG Specific Human PD-L1 Antibodies in Supernatants

Indirect Capture ELISA:

In the first screen, detection of the antibody producing mouse sera or hybridomas was carried out using an indirect ELISA protocol and single dilutions of the sera or hybridoma supernatants. Subsequent screens were done with dilutions of the mouse sera or hybridoma supernatants. The format of the ELISA is as shown in the schematic FIG. 1.

Figure 3:
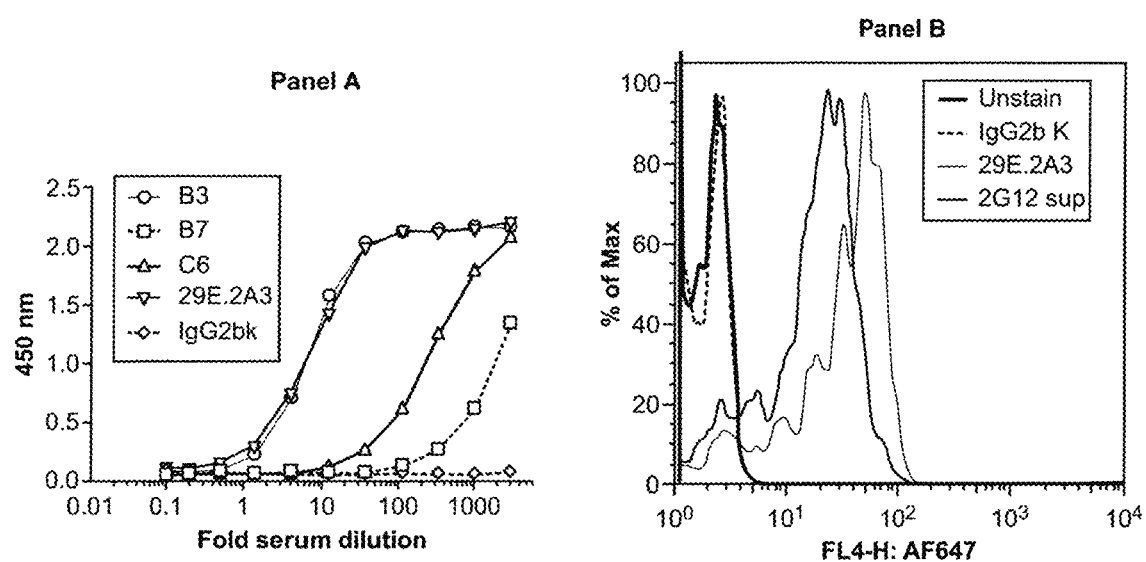
FIG. 3, Panel A is a graph showing activity of three hybridoma supernatants in the indirect ELISA along with positive and negative control antibodies. Panel B is a graph showing example data from FACS screening of hybridoma supernatants along with positive and negative controls.

Ninety-six well high binding protein plates were coated with 50 uL of goat anti-human IgG Fc in PBS at 1 ug/mL (Southern Biotech, cat#2014-01) overnight at 4 C. The plates were washed 3× with PBS 0.05% Tween20 and then dried by tapping several times on paper towels. The plates were blocked with 200 uL of 1% milk for 1 hr at RT. The wash and dry steps were repeated as above and the plates were incubated with 50 uL of 200 ng/mL recombinant human B7-H1 (PD-L1) Fc chimera protein in 1% milk (R&D, cat#156-87-1000) for 1 hr at RT. To screen for specificity, recombinant cynomolgus monkey PD-L1 Fc chimera (Sino Biological, cat#90251-C02H), recombinant mouse PD-L1 Fc chimera (Sino Biologicals, cat#50010-M02H), or recombinant human PD-L2 Fc chimera protein (Sino Biological, cat#10292-H02H) were used in place of the human PD-L1 Fc chimera. After washing and drying the plates as above, positive control antibody (mouse anti-human PD-L1, 29E.2A3, BioLegend, cat#329702) and its isotype control (mouse IgG2b k, BioLegend, cat#400302) were serially diluted 3-fold in 1% milk starting at 3 ug/mL to 0.1 ng/mL and 50 uL of the titrated antibodies were added to their respective wells on all the plates. The hybridoma supernatants were each diluted 1:3 in 1% milk. Fifty μL of the supernatants were added to the respective wells. The plates were incubated for 1 hr at RT. They were washed and dried as above and then incubated with 50 uL of 1:5000 goat anti-mouse IgG Fc conjugated with horseradish peroxidase (HRP) for 1 hr at RT (Jackson Immuno Research, cat#115-035-071). After repeating the wash and drying step, the plates were developed for 20-30 min with 50 uL TMB substrate (BD OptiIEIA, cat#555214). The reaction was stopped with 50 uL of 2N H2SO4 and absorbance at 450 nm was read on a Spectramax Gemini spectrophotometer. Example data for serially diluted hybridoma supernatants is shown in FIG. 3, Panel A.

1.4 Detection of Antibody Binding to Human PD-L1-Expressing Cells

Figure 2:
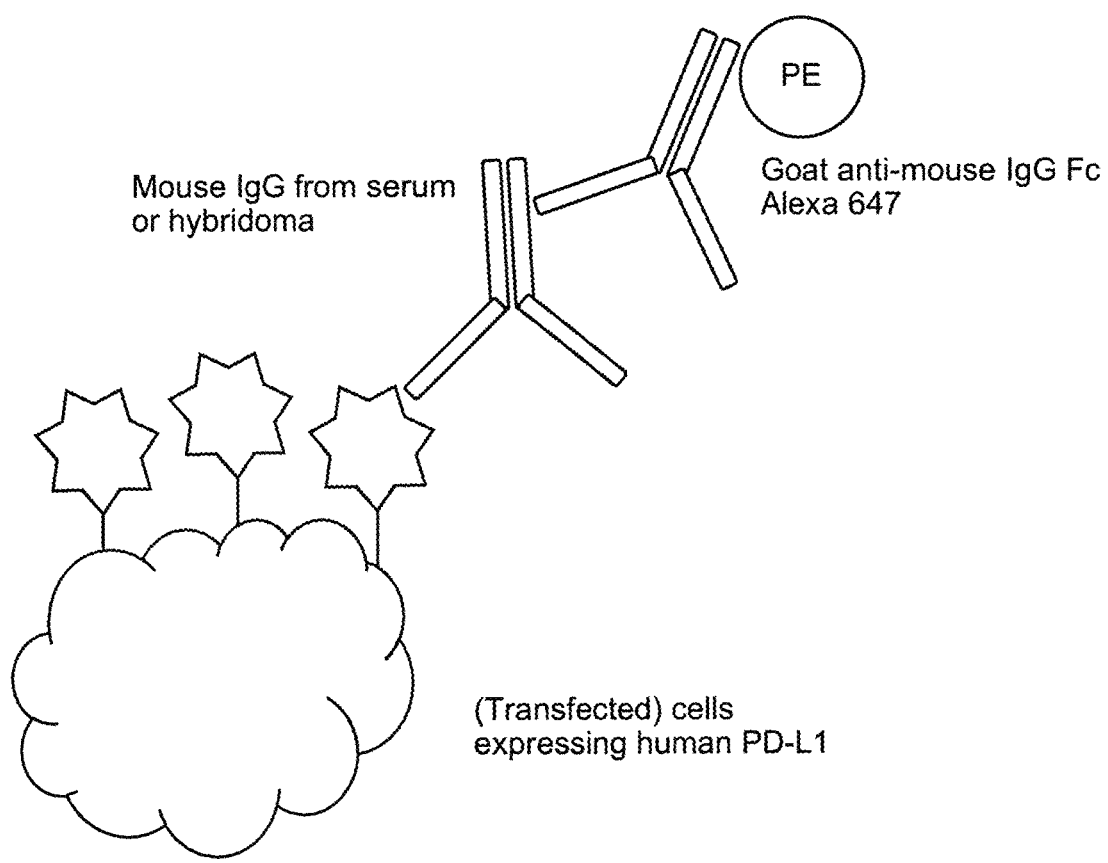
FIG. 2 is a schematic representation of a flow cytometry assay that was used to determine reactivity and specificity of anti-human PD-L1 antibodies.

Binding Reactivity by Flow Cytometry:

Cell lines such as Granta (DSMZ ACC#342) or Promega 187103 cells (Promega, cat#187106) expressing human PD-L1 on their cell surface were used to determine the reactivity and specificity of the anti-human PD-L1 monoclonal antibodies in the hybridoma supernatants by flow cytometry as shown in FIG. 2.

Cells were replenished with fresh media the day before staining. On the day of staining the cells were dislodged using HyQtase (GE Health & Life Sciences, cat# SV30030.01). After aspirating off all the media, the cells were rinsed with 10 mL of PBS without calcium or magnesium. After aspirating off the PBS, the cells were incubated with 5 ml of HyQtase for 5 min at 37 C. The cells were then dislodged by tapping the flask to create a single cell suspension. HyQtase was neutralized by adding an equal amount of media, and live cell counts were determined using Trypan Blue exclusion on a cell counter (BioRad TC20). The density of the cells was adjusted to 1.5×10e4 cells per 60 μL of FACS 2% FBS buffer.

Compressed Staining [3 (Hybridoma Sups Plates) to 1 (PD-L1 Expressing Cell Plate)].

Cells, 1.5×10$^4$/well in 60 uL of FACS 2% FBS buffer (BD Pharmingen, cat#554656), were added to "v" bottom 96 well plates. With a 12 well multichannel pipette, 10 uL of the supernatant from each well of the hybridoma plates was added to the cells corresponding to the wells. This was repeated with 3 hybridoma supernatant plates, combining supernatants from 3 hybridoma wells into each well containing cells. The positive control 29E.2A3 (BioLegend, cat#329702) and IgG2b k isotype control (BioLegend, cat#400302) were added to the cells at 1 ug/mL and designated as the control wells. The plates were incubated at 4C for 30 min. After washing the cells with 150 µL of FACS 2% FBS buffer, the plates were centrifuged (Sorvall Legend XIR centrifuge) at 1200 rpm for 5 min and supernatants were gently aspirated without disturbing the cell pellets. Antibody binding was detected by incubating the cells with AF647 goat anti-mouse IgG (Jackson ImmunoResearch, cat#115-605-164) at 4C for 30 min. The wash step was repeated as above and the cells were resuspended in 60 µL of FACS 2% FBS with 1:100 7_AAD (BD Pharm, cat#68981E). One thousand events of the samples were acquired for each sample on a FACSCalibur (Becton Dickinson) and the analysis was done in the FLOJO® flow cytometry platform. The binding detected in the supernatants was compared to the positive and isotype controls and positive wells were marked.

Deconvoluting the FACS Positive Hybridoma Wells:

Each of the positive wells from compressed plates/wells were decompressed to individual plate/well where hybridoma supernatants from the individual well from each of the 3 compressed plates were tested individually for positive staining on Promega 187103 cells as per the protocol above. The binding was compared to the isotype control identifying anti PD-L1 antibody producing hybridoma, and ELISA-positive wells showing high levels of binding to PD-L1-expressing cells were advanced to the next screen. Example data for FACS screening of hybridoma supernatants is shown in FIG. 3, Panel B.

Indirect Capture ELISA: Titration of FACS Positive Supernatants.

Titration of the positive supernatants from the first screen of the hybridomas was carried out using the indirect ELISA protocol described above where the supernatants were serially diluted 3-fold in 1% milk before being added to the wells. The concentration of murine antibody in selected hybridoma supernatants was estimated by indirect ELISA using the commercial 29E.2A3 antibody of known concentration. The positive supernatants were then tested for functionality in the PD1/PD-L1 Blockade assay.

Figure 4:
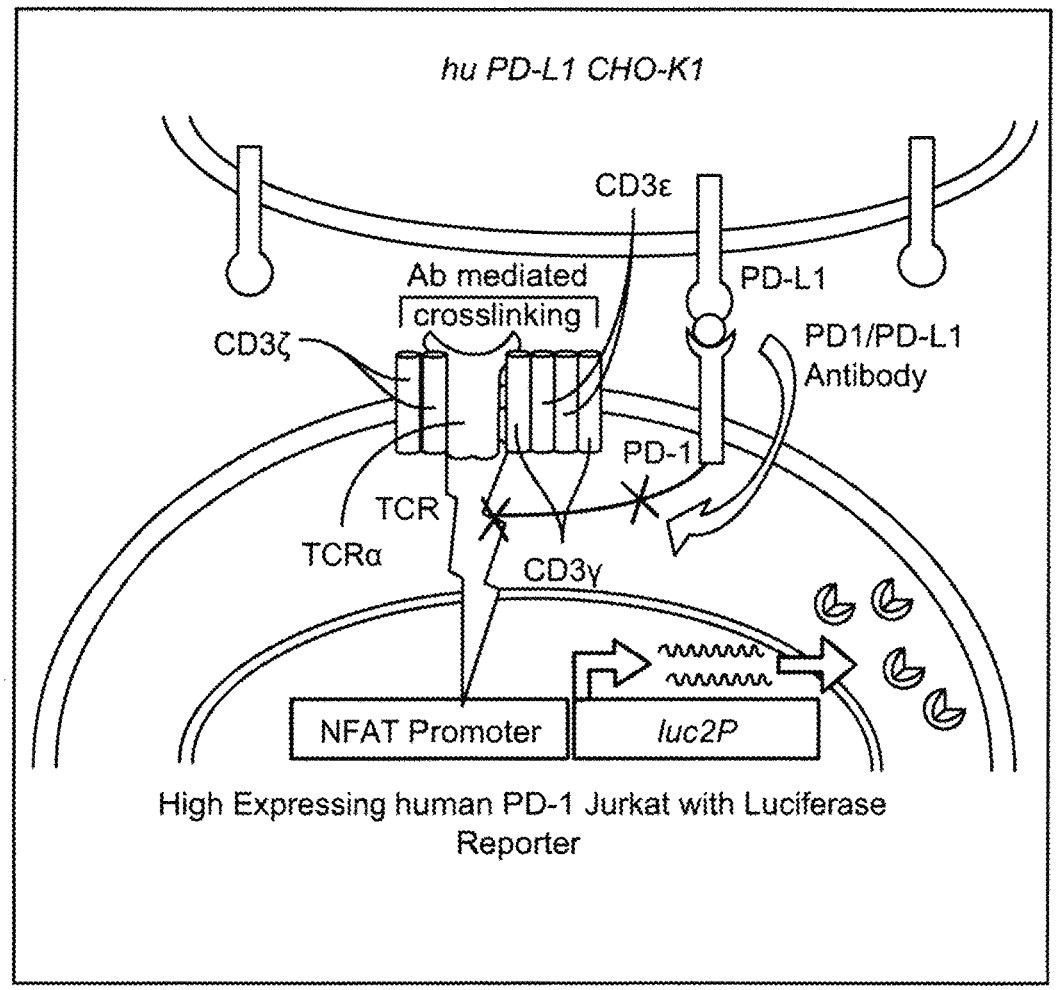
FIG. 4 is a schematic representation of a PD-1/PD-L1 blockade assay based on NFAT-driven expression of luciferase on a Jurkat-based reporter cell line that overexpresses PD-1 and is suppressed in the presence of CHO cells over-expressing the PD-L1 antigen.

Example 2: Testing of FACS and ELISA Positive Hybridoma Supernatants in Functional Assay for PD-1/PD-L1 Blockade While the screening assays described above are able to identify clones that can bind to PD-L1 as antigen coated on a plate or on a cell surface, the antibodies we want to develop are required to effectively block the interaction of PD-1 with PD-L1. To test the ability of the FACS and ELISA positive antibodies identified above to block this interaction, we used a commercially available PD-1/PD-L1 blockade assay (Promega) with a luminescence based readout (FIG. 4).

Briefly, frozen CHO cells with surface expression of PD-L1 (Promega CS187103) were thawed at 37° C. and re-suspended in DMEM supplemented with 10% Fetal Bovine Serum (Invitrogen). Media containing 7,500 cells was added into wells of a 384-well plate for 16h at 37° C. and 5% $CO_2$. Media was replaced with 10 uL RPMI+2% FBS containing antibody. Additional 10 uL of media containing 10,000 engineered Jurkat cells (Promega CS187105) was added to the wells and incubated for 5h at 37° C. with 5% $CO_2$. Cells were mixed with 20 µL of lysis buffer containing luciferin (Promega, Cell Titer Glo) to measure luciferase reporter activity. Light output was measured by an EnVision plate reader. $EC_{50}$ was determined by 4 parameter curve fit using Prism software.

Figure 5:
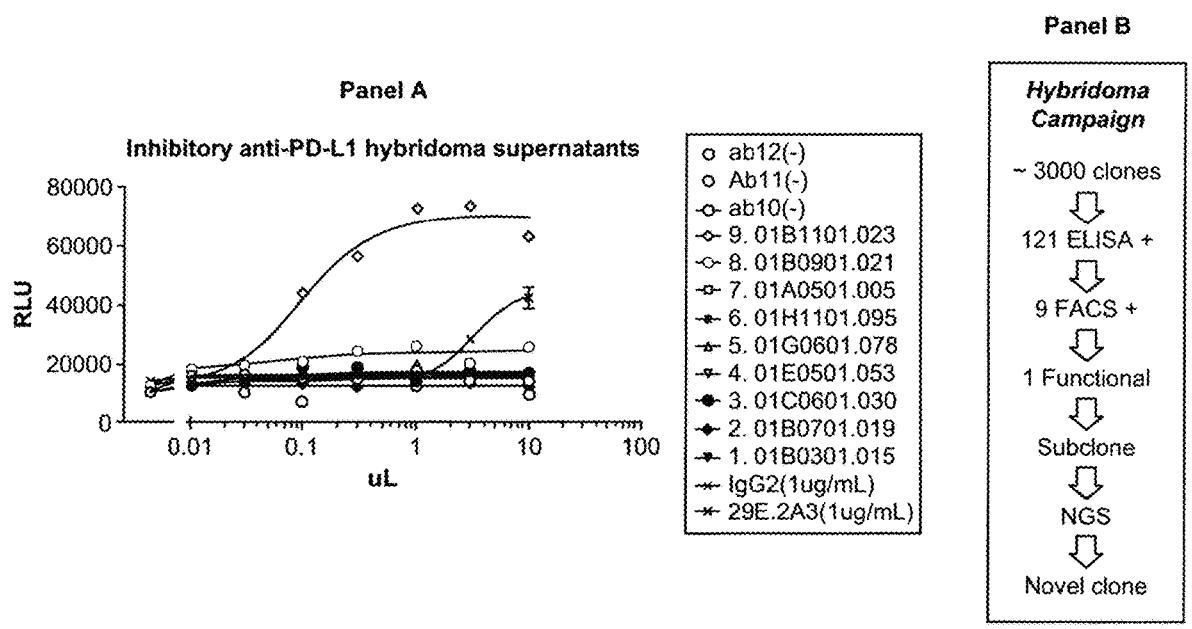
FIG. 5, Panel A is a graph showing example data from screening of hybridoma supernatants in a PD-1/PD-L1 blockade assay. Panel B is a schematic depiction of the hybridoma screening strategy and results.

Example data from screening of hybridoma supernatants in the blockade assay is shown in FIG. 5, Panel A. The hybridoma screening strategy and results are summarized in FIG. 5, Panel B. Overall, ~3000 hybridoma supernatants were screened and yielded 121 ELISA-positive clones. Of these, 9 were FACS-positive clones and only one (3C5) exhibited functional activity in the bioassay. This clone was further subcloned and one of the sub-clones 3C5-2G12 was used to carry out next-generation sequencing in order to identify the VH and VL sequences as described below.

Example 3: Hybridoma Sequencing with Next Generation Sequencing (NGS) Protocol

Figure 6:
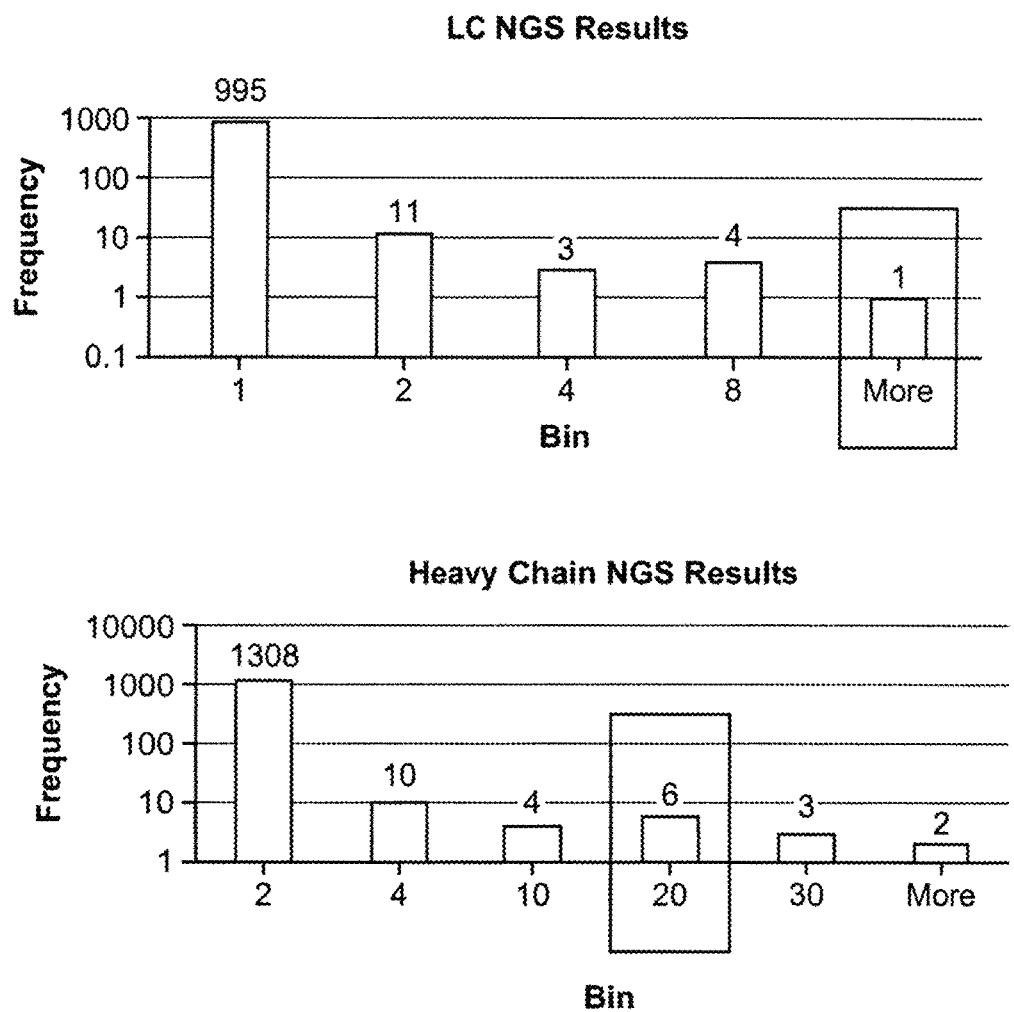
FIG. 6, Panel A is a bar graph showing the distribution of NGS-derived sequences from 3C5-2G12 light chains. Panel B is a bar graph showing the distribution of NGS-derived sequences from 3C5-2G12 heavy chains. Not all heavy chains were expressed at the same level.

Typical hybridomas have multiple heavy and light chains expressed and one or more of these can be the sequence responsible for activity seen in functional assays. Next generation sequencing (NGS) methods were applied to identify the sequence from hybridomas identified as positive in ELISA, FACS and blocking assays. Briefly, the RNA was extracted from the hybridomas (1×10$^6$ cells) and single strand DNA was generated using a RACE-PCR protocol. To amplify both heavy and light chains, degenerate primers for mouse IgG and mouse IgK regions were used. The primers were designed to cover the variable region from FR1 to FR4. The samples were bar coded and paired-end sequenced using a MiSeq NGS sequencer (Illumina). The resulting Fastq files were analyzed using customized software at Panoply Bio (Carlsbad, Calif.). The sequences were aligned for the overlapping paired-ends and CDRs were identified using the mouse framework regions. The data was assembled based on the frequency of each sequence. A number of truncations can be encountered in this sequence assembly process, so the sequences chosen for cloning and further testing were based on the following criteria:
1) Presence of all 3 CDR's
2) Multiple occurrence in family of sequences
3) Highest frequency of CDR's
4) No apparent truncations at N-terminus In hybridomas, the most dominant clone is likely to have the most frequent sequences. Usually, there can be other clones that will bind the target just as well, or better or worse, but they may not be expressed as highly or may not grow as well in culture. In the family of sequences obtained from light chains, one sequence was dominant over all others based on these criteria. As shown in FIG. 6, Panel A, one sequence occurred 24 times and is reproduced below.

```
3C5-2G12 Light Chain Sequence:
                                        (SEQ ID NO: 46)
DIQMNQSPSSLSASLGDTITITCRASQDISIWLSWYQQKPGNIPELLIYK
ASNLHTGVPPRFSGSGSGTDFTLTISSLQPEDIATYYCLQSQSFPRTFGG
GTKLEIK
```

However, the NGS data from heavy chain sequencing showed multiple sequences with high frequencies as shown in FIG. 6, Panel B. Therefore, additional filters were used to decide which sequences presented the highest likelihood of coding for the active antibody produced by this hybridoma. For example, the most frequently occurring sequence in this set occurred 47 times, but had a large N-terminal truncation and was missing CDR1, so was not considered. Instead, the highest frequency sequence with all three CDRs and no truncations at the N-terminus was chosen for testing. This sequence occurred 19 times in this set of sequences, contains all three CDRs and appears to have an intact N-terminus (similar to germ-line).

3C5-2G12 Heavy Chain Sequence:
(SEQ ID NO: 45)
QVQLKESGPGLVAPSQSLSITCTVSGFSLTSYDISWVRQPPGKGLEWLGV
IWTGVGTNYNSAFMSRLSISKDNSKSQVFLKMNSLQTDDTAMYYCVRDPY
YYGMDYWGQGTSVTVSS

Example 4: Production and Testing of 3C5-2G12 IgG and IgM

1. Generation of DNA Constructs with Designed Mutations

DNA Construct Synthesis.

All the DNA constructs with designed mutations were synthesized by commercial vendors (e.g. Genescript, Lake Pharma), with compatible restriction sites at both ends for sub-cloning into respective expression vectors.

Constructing Expression Vectors.

The synthesized DNA constructs were re-suspended in Tris-EDTA buffer at 1 μg/ml. DNA (1 μg) was subjected to enzyme digestion and the synthesized gene was separated from the carrier plasmid DNA by electrophoresis. The digested DNA was ligated to pre-digested expression vector plasmid DNA by standard molecular biology techniques. The ligated DNA was transformed into competent bacteria and plated on LB plates with multiple selective antibiotics. Several bacterial colonies were picked and DNA preparations were made by standard molecular biology techniques. The prepared DNA were verified by sequencing. Only the bacterial clones with 100% match of DNA sequence with the designed DNA sequence were used for plasmid DNA preparation and subsequently for cell transfection.

The sequences for the 3C5-2G12 VH and VL sequences in the context of IgG and IgM heavy and light chains are shown below.

Figure 7:
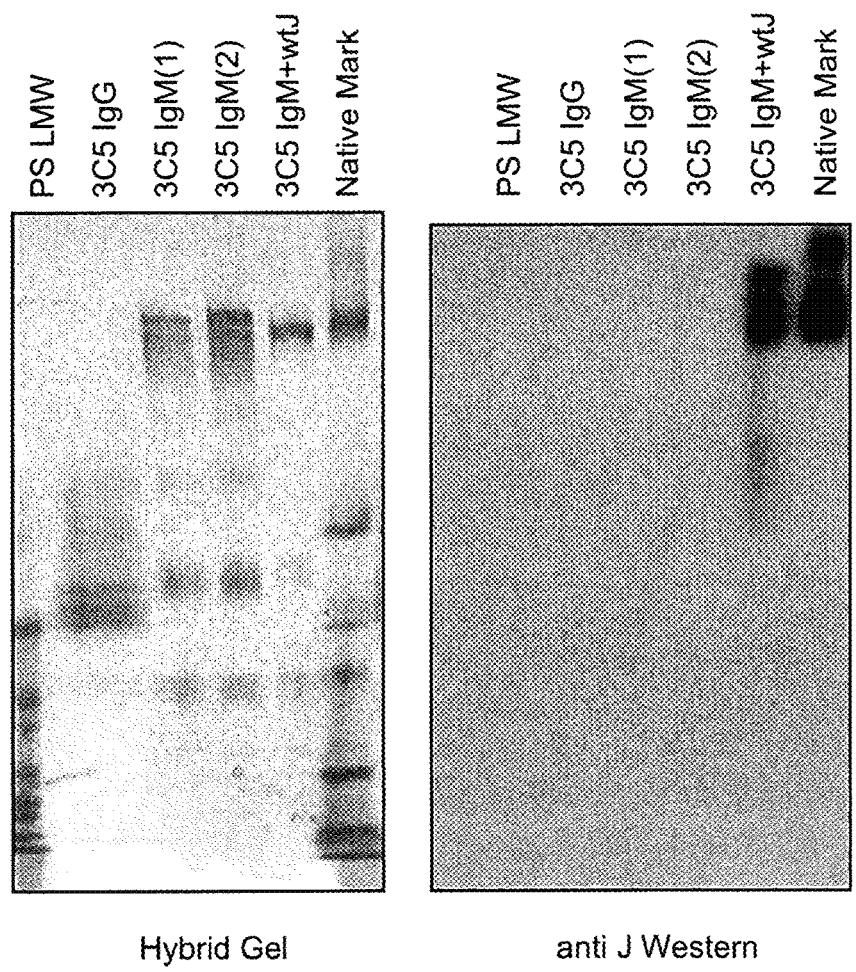
FIG. 7 is an image of a Coomassie stained hybrid gel (left) and western blot with anti-J chain antibody. The images show formation of fully assembled IgM pentamer as well as incorporation of J-chain.

3C5-2G12 IgG1 Antibody HC:
(SEQ ID NO: 49)
MDPKGSLSWRILLFLSLAFELSYGQVQLKESGPGLVAPSQSLSITCTVSG
FSLTSYDISWVRQPPGKGLEWLGVIWTGVGTNYNSAFMSRLSISKDNSKS
QVFLKMNSLQTDDTAMYYCVRDPYYYGMDYWGQGTSVTVSSASTKGPSVF
PLAPSSKSTSGGTAALGCLVKDYFPEPVTVSWNSGALTSGVHTFPAVLQS
SGLYSLSSVVTVPSSSLGTQTYICNVNHKPSNTKVDKKVEPKSCDKTHTC
PPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNK ALPAPIEKTISKAKGQPREPQVYTLPPSRDELTKNQVSLTCLVKGFYPSD
IAVEWESNGQPENNYKTTPPVLDSDGSFFLYSKLTVDKSRWQQGNVFSCS
VMHEALHNHYTQKSLSLSPG 3C5-2G12 IgM Antibody HC:
(SEQ ID NO: 50)
MDPKGSLSWRILLFLSLAFELSYGQVQLKESGPGLVAPSQSLSITCTVSG
FSLTSYDISWVRQPPGKGLEWLGVIWTGVGTNYNSAFMSRLSISKDNSKS
QVFLKMNSLQTDDTAMYYCVRDPYYYGMDYWGQGTSVTVSSGSASAPTLF
PLVSCENSPSDTSSVAVGCLAQDFLPDSITFSWKYKNNSDISSTRGFPSV
LRGGKYAATSQVLLPSKDVMQGTDEHVVCKVQHPNGNKEKNVPLPVIAEL
PPKVSVFVPPRDGFFGNPRKSKLICQATGFSPRQIQVSWLREGKQVGSGV
TTDQVQAEAKESGPTTYKVTSTLTIKESDWLSQSMFTCRVDHRGLTFQQN
ASSMCVPDQDTAIRVFAIPPSFASIFLTKSTKLTCLVTDLTTYDSVTISW
TRQNGEAVKTHTNISESHPNATFSAVGEASICEDDWNSGERFTCTVTHTD
LPSPLKQTISRPKGVALHRPDVYLLPPAREQLNLRESATITCLVTGFSPA
DVFVQWMQRGQPLSPEKYVTSAPMPEPQAPGRYFAHSILTVSEEEWNTGE
TYTCVVAHEALPNRVTERTVDKSTGKPTLYNVSLVMSDTAGTCY 3C5-2G12 IgG, IgM Antibody LC:
(SEQ ID NO: 51)
METDTLLLWVLLLWVPGSTGDIQMNQSPSSLSASLGDTITITCRASQDIS
IWLSWYQQKPGNIPELLIYKASNLHTGVPPRFSGSGSGTDFTLTISSLQP
EDIATYYCLQSQSFPRTFGGGTKLEIKRTVAAPSVFIFPPSDEQLKSGTA
SVVCLLNNFYPREAKVQWKVDNALQSGNSQESVTEQDSKDSTYSLSSTLT
LSKADYEKHKVYACEVTHQGLSSPVTKSFNRGEC 3C5-2G12 IgM + J Antibody J-Chain sequence:
(SEQ ID NO: 47)
QEDERIVLVDNKCKCARITSRIIRSSEDPNEDIVERNIRIIVPLNNRENI
SDPTSPLRTRFVYHLSDLCKKCDPTEVELDNQIVTATQSNICDEDSATET
CYTYDRNKCYTAVVPLVYGGETKMVETALTPDACYPD DNA corresponding to these sequences was synthesized and transfected into HEK293 cells to produce protein which was then purified using the camelid antibody affinity matrix specific for IgM. As shown in FIG. 7, J-chain was able to incorporate into the IgM and the pentameric form of IgM with the corresponding J-chain was clearly distinguishable from the hexameric form without a J-chain.

2. Protein Expression, Purification and Characterization a. Transfection.

Heavy, Light and J-chain DNA was transfected into CHO or HEK293 cells. DNA for expression vectors were mixed typically in 1:1:1 ratio with PEI and then added to CHO-S cells. PEI transfection with CHO-S cells was conducted according to established techniques (see Biotechnology and Bioengineering, Vol 87, 553-545).

b. Immunoprecipitation.

i. Capture Select IgM (BAC, Thermo Fisher). IgM proteins from transfected CHO cell supernatants were partially purified by immuno-precipitation with Capture Select IgM affinity matrix according to manufacturers' protocol (GE Life Sciences). After incubation at room temperature for 2 hours, the affinity matrix was separated from the supernatant by centrifugation. The matrix was further washed with PBS for 3 times before the PBS was carefully removed. The captured protein was eluted from the matrix by incubating with NuPage LDS protein buffer (Life Technology) for 5 minutes.

c. Gel electrophoresis.

i. Non-reducing SDS PAGE: Non-reducing SDS PAGE separates native IgM and its mutant forms according to size. Pentameric IgM, composed of homodimeric heavy and light chains, produces a protein band of approximately 1,000,000 molecular weight. NuPage LDS Sample Buffer (Life Technologies) was added to IgM protein samples at 25C for 30 minutes before loading onto the gel. NativePage Novex 3-12% Bis-Tris Gel (Life Technologies) was used with Novex Tris-Acetate SDS Running Buffer (Life Technologies). The gel was run until the dye front reached the bottom of the gel.

ii. Reducing SDS-PAGE: NuPage LDS sample buffer (Life Technologies) and NuPage reducing agent dithiothreitol (Life Technologies) were added to IgM protein samples and heated to 80° C. for 10 minutes before loading on NuPage Novex 4-12% Bis-Tris Gel (Life Technologies). NuPage MES SDS Running Buffer (Life Technologies) was used for gel electrophoresis. Gels were run until the dye front reached the bottom of the gel. After electrophoresis was complete, the gel was removed from the apparatus and stained using Colloidal Blue Staining (Life Technologies).

iii. Western Blot: An acrylamide gel run under conditions described above was washed in a 20% ethanol solution for 10 minutes and then the protein was transferred to an iBlot PVDF membrane (Invitrogen) using the iBlot Dry Blotting System (Invitrogen) at 20V for 10 minutes. After transfer the PVDF membrane was blocked using 2% bovine serum albumin, 0.05% Tween 20 for at least 12 hours. A 1/500 dilution of Pierce J-chain antibody (ThermoFisher) was added to the membrane, incubated for 1 hour, and then a 1/5000 dilution of peroxidase-conjugated goat anti-rabbit IgG (Jackson ImmunoResearch) was added and allowed to incubate in darkness for 30 minutes. Finally, Super Signal West Pico Chemiluminescent Substrate (ThermoFisher) was added to the blot and the resulting signal was visualized using the ChemiDoc-It HR410 Imaging System (UVP) or by exposing the blot to X-ray film.

Example 5: Functional Testing of 3C5-2G12 IgG and IgM

As before, frozen CHO cells with surface expression of PD-L1 (Promega CS187103) were thawed at 37° C. and re-suspended in DMEM supplemented with 10% Fetal Bovine Serum (Invitrogen). Media containing 7,500 cells was added into wells of a 384-well plate for 16h at 37° C. and 5% $CO_2$. Media was replaced with 10 uL RPMI+2% FBS containing 3C5-1G12 or control antibody. Additional 10 uL of media containing 10,000 engineered Jurkat cells (Promega CS187105) was added to the wells and incubated for 5h at 37° C. with 5% $CO_2$. Cells were mixed with 20 μL of lysis buffer containing luciferin (Promega, Cell Titer Glo) to measure luciferase reporter activity. Light output was measured by an EnVision plate reader. $EC_{50}$ was determined by 4 parameter curve fit using Prism software.

Figure 8:
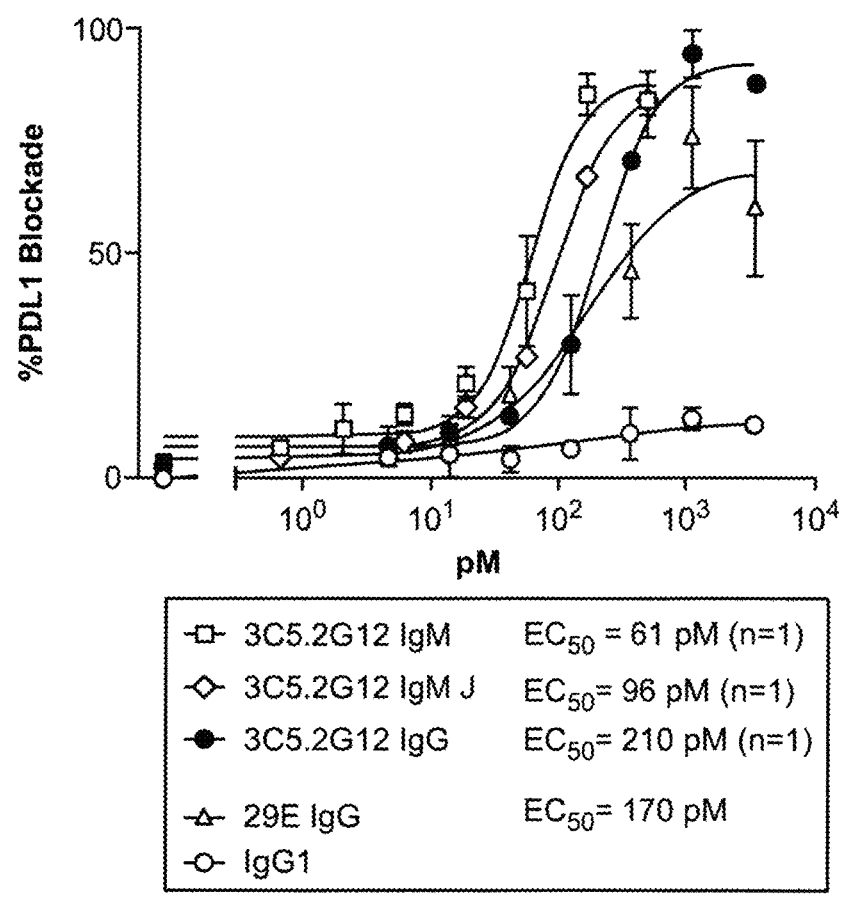
FIG. 8 is a graph showing PD-L1 blockade data from the 3C5.2G12 IgM, 3C5.2G12 IgM+J chain, and 3C5.2G12 IgG antibody formats.

Example data from testing of purified 3C5-2G12 antibody preparations in the blockade assay is shown in FIG. 8. The IgM and IgM+J formats appear highly potent (61 pM and 96 pM) and more so than the IgG format in this assay.

Example 6: Cross-Reactivity Testing of 3C5-2G12 IgG and IgM

Figure 9:
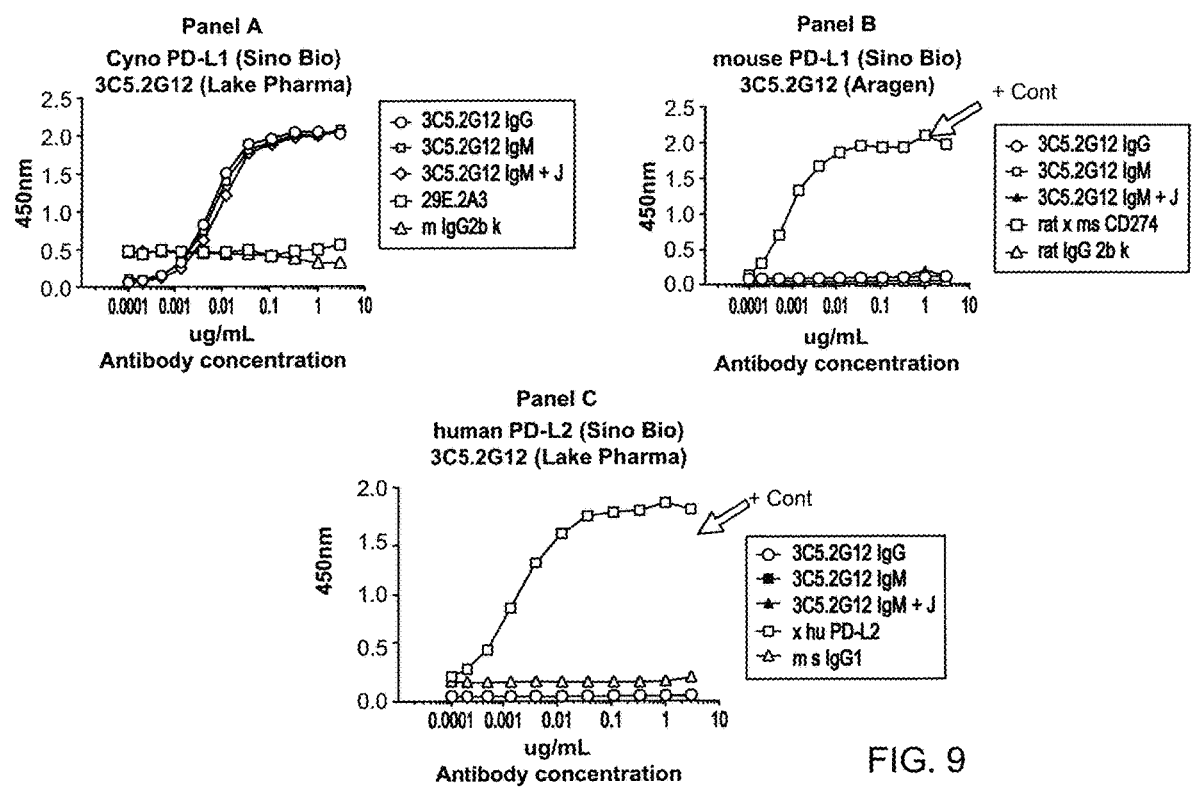
FIG. 9, Panel A is a graph showing 3C5.2G12 cross reactivity with Cyno PD-L1. Panel B is a graph showing lack of 3C5.2G12 cross reactivity with mouse PD-L1. Panel C is a graph showing lack of 3C5.2G12 cross reactivity with human PD-L2.

Recombinant human PD-L1 Fc chimera (Sino Biological, cat#10084-H02H), recombinant cynomolgous monkey PD-L1 Fc chimera (Sino Biological, cat#90251-CO2H), recombinant mouse PD-L1 Fc chimera (Sino Biologicals, cat#50010-M02H) and recombinant human PD-L2 Fc chimera protein (Sino Biological, cat#10292-H02H) were coated directly onto the ELISA plates at 1 ug/mL by overnight incubation at 4° C. The plates were washed 3× with PBS 0.05% Tween and dried by tapping several times on paper towels. All the plates were blocked with 200 uL of 1% milk for 1 hr at RT. After washing and drying the plates as above, 3C5.2G12 IgG, 3C5.2G12 IgM and 3C5.2G12 IgM+wtJ antibodies were each diluted 1:3 in 1% milk starting at 3 ug/mL to 0.1 ng/mL. Fifty μL of the diluted antibodies were added to the respective wells in all the plates. Positive control antibody (mouse anti-human PD-L1, 29E.2A3, (BioLegend, cat#329702) and its isotype control mouse IgG2b k (BioLegend, cat#400302) were serially diluted 3-fold in 1% milk starting at 3 ug/mL to 0.1 ng/mL and 50 uL of the titrated antibodies were added to their respective plates/wells. Similarly rat anti mouse PD-L1 (BioLegend, cat#124302) and rat IgG2b isotype (BioLegend, cat#400622), anti-human PD-L2 (BioLegend, cat#345502) with mouse IgG1 isotype (BioLegend, cat#4011402) were titrated as above and added to its respective plates/wells. The plates were incubated for 1hr at RT. They were washed and dried as above and then all the 3C5.2G12's were incubated with 50 uL of 1:5000 goat anti-human kappa light chain antibody conjugated with horseradish peroxidase (HRP) for 1 hr at RT (Jackson Immuno Research, cat#115-035-071). For the control wells, appropriate secondary antibodies, goat anti mouse HRP (Southern Biotech, cat#1033) and mouse anti rat HRP (Southern Biotech, cat#3070-05), were diluted and incubated as above. After repeating the wash and drying step, the plates were developed for 20~30 min with 50 uL TMB substrate (BD OptiIEIA, cat#555214). The reaction was stopped with 50 uL of 2N H2504 and absorbance at 450 nm was read on a Spectramax Gemini spectrophotometer. Example data for serially diluted 3C5.2G12 is shown in FIG. 9, Panel A, Panel B, and Panel C.

Example 7: Humanization of 3C5-2G12 IgG and IgM

Humanization of 3C5-2G12 antibody was carried out in both formats (IgG and IgM). The sequences and the combinations that were produced for testing are shown below.

h3C5H1-hIgG1:

(SEQ ID NO: 52)

```
MDPKGSLSWRILLFLSLAFELSYGQVQLQESGPGLVKPSETLSLICTVSG

FSLTSYDISWIRQPPGKGLEWIGVIWTGVGTNYNPSLKSRVTISVDTSKN

QFSLKLSSVTAADTAVYYCARDPYYYGMDYWGQGTLVTVSSASTKGPSVF

PLAPSSKSTSGGTAALGCLVKDYFPEPVTVSWNSGALTSGVHTFPAVLQS

SGLYSLSSVVTVPSSSLGTQTYICNVNHKPSNTKVDKKVEPKSCDKTHTC
```

```
PPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNK

ALPAPIEKTISKAKGQPREPQVYTLPPSRDELTKNQVSLTCLVKGFYPSD

IAVEWESNGQPENNYKTTPPVLDSDGSFFLYSKLTVDKSRWQQGNVFSCS

VMHEALHNHYTQKSLSLSPG h3C5H2-hIgG1:
                                     (SEQ ID NO: 53)
MDPKGSLSWRILLFLSLAFELSYGQVQLQESGPGLVKPSETLSLICTVSG

FSLTSYDISWIRQPPGKGLEWLGVIWTGVGTNYNPSLKSRVTISKDTSKN

QFSLKLSSVTAADTAVYYCARDPYYYGMDYWGQGTLVTVSSASTKGPSVF

PLAPSSKSTSGGTAALGCLVKDYFPEPVTVSWNSGALTSGVHTFPAVLQS

SGLYSLSSVVTVPSSSLGTQTYICNVNHKPSNTKVDKKVEPKSCDKTHTC

PPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNK

ALPAPIEKTISKAKGQPREPQVYTLPPSRDELTKNQVSLTCLVKGFYPSD

IAVEWESNGQPENNYKTTPPVLDSDGSFFLYSKLTVDKSRWQQGNVFSCS

VMHEALHNHYTQKSLSLSPG h3C5H3-hIgG1:
                                     (SEQ ID NO: 54)
MDPKGSLSWRILLFLSLAFELSYGQVQLQESGPGLVKPSETLSITCTVSG

FSLTSYDISWVRQPPGKGLEWLGVIWTGVGTNYNPSFKSRLTISKDTSKN

QVSLKMSSLTAADTAVYYCVRDPYYYGMDYWGQGTLVTVSSASTKGPSVF

PLAPSSKSTSGGTAALGCLVKDYFPEPVTVSWNSGALTSGVHTFPAVLQS

SGLYSLSSVVTVPSSSLGTQTYICNVNHKPSNTKVDKKVEPKSCDKTHTC

PPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNK

ALPAPIEKTISKAKGQPREPQVYTLPPSRDELTKNQVSLTCLVKGFYPSD

IAVEWESNGQPENNYKTTPPVLDSDGSFFLYSKLTVDKSRWQQGNVFSCS

VMHEALHNHYTQKSLSLSPG h3C5H4-hIgG1:
                                     (SEQ ID NO: 55)
MDPKGSLSWRILLFLSLAFELSYGQVQLQESGPGLVKPSETLSITCTVSG

FSLTSYDISWIRQPPGKGLEWLGVIWTGVGTNYNPSFKSRLTISKDNSKN

QVSLKMSSLTAADTAVYYCVRDPYYYGMDYWGQGTLVTVSSASTKGPSVF

PLAPSSKSTSGGTAALGCLVKDYFPEPVTVSWNSGALTSGVHTFPAVLQS

SGLYSLSSVVTVPSSSLGTQTYICNVNHKPSNTKVDKKVEPKSCDKTHTC

PPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNK

ALPAPIEKTISKAKGQPREPQVYTLPPSRDELTKNQVSLTCLVKGFYPSD

IAVEWESNGQPENNYKTTPPVLDSDGSFFLYSKLTVDKSRWQQGNVFSCS

VMHEALHNHYTQKSLSLSPG h3C5L1-hKappa:
                                     (SEQ ID NO: 56)
METDTLLLWVLLLWVPGSTGDIQMTQSPSSLSASVGDRVTITCRASQDIS

IWLSWYQQKPGKAPKLLIYKASNLHTGVPSRFSGSGSGTDFTLTISSLQP

EDFATYYCLQSQSFPRTFGQGTKLEIKRTVAAPSVFIFPPSDEQLKSGTA

SVVCLLNNFYPREAKVQWKVDNALQSGNSQESVTEQDSKDSTYSLSSTLT

LSKADYEKHKVYACEVTHQGLSSPVTKSFNRGEC h3C5L2-hKappa:
                                     (SEQ ID NO: 57)
METDTLLLWVLLLWVPGSTGDIQMTQSPSSLSASVGDRITITCRASQDIS

IWLSWYQQKPGKAPKLLIYKASNLHTGVPSRFSGSGSGTDFTLTISSLQP

EDFATYYCLQSQSFPRTFGQGTKLEIKRTVAAPSVFIFPPSDEQLKSGTA

SVVCLLNNFYPREAKVQWKVDNALQSGNSQESVTEQDSKDSTYSLSSTLT

LSKADYEKHKVYACEVTHQGLSSPVTKSFNRGEC
```

The following combinations were made in the form of IgG using standard techniques described above and purified using Protein A.
h3C5H1-h3C5L1
h3C5H2-h3C5L2
h3C5H3-h3C5L2
h3C5H4-h3C5L2

Figure 10:
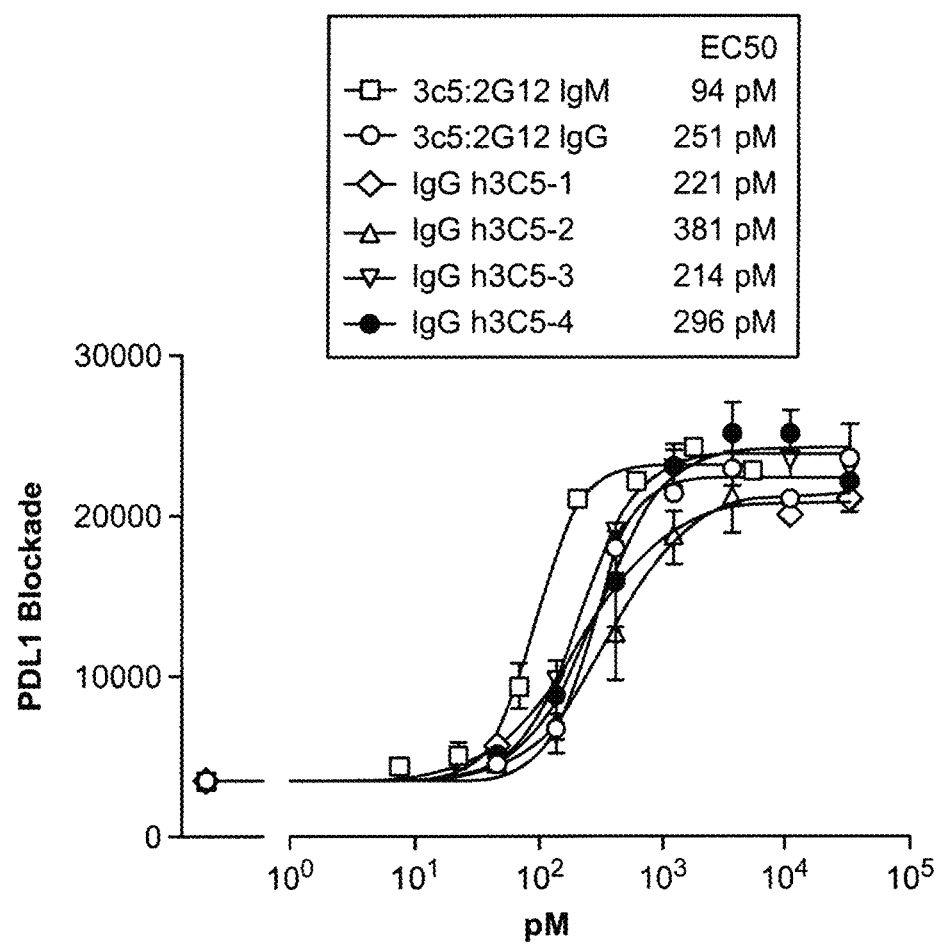
FIG. 10 is a graph showing PD-L1 blockade data from 3C5.2G12 IgM and 3C5.2G12 IgG format antibodies, as well as IgG h3C5-1, IgG h3C5-2, IgG h3C5-3 and IgG h3C5-4 antibodies.

The results from testing each of these antibodies in the PD-L1 blockade assay are shown in FIG. 10. The conservative changes made during the humanization process all appear to have had little impact on the blockade activity of the humanized antibody.

Example 8: Epitope Mapping

Peptide epitope mapping was carried out by creating a library of all overlapping 15-amino acid linear peptides covering amino acids 19 to 132 of the extracellular domain of PD-L1 (Q9NZQ7, SEQ ID NO: 48), via direct synthesis onto a solid support using the PEPSCAN™ system.

Antibody binding was quantified in the PEPSCAN™ system using an automated ELISA-type read-out. Binding to the peptide array was determined for the 3C5 antibody (IgG format) and control antibody YW243.55570 (referred to herein as "S70"), a reference antibody that binds to PD-L1. The S70 heavy chain and light chain sequences are disclosed in U.S. Pat. No. 8,217,149, the disclosure of which is incorporated by reference herein in its entirety. The hPD-L1 epitope that bound the S70 antibody was clearly mapped to the amino acid sequence QDAGVYRCMIS (amino acids 107 to 117 of SEQ ID NO: 48). This epitope includes three amino acids (R113, M115, and 5117) of the fourteen discontinuous residues of hPD-L1 calculated to contact hPD-1. See Lin, D. Y. et al., Proc. Natl. Acad. Sci. USA 105:3011-3016 (2008), incorporated herein by reference in its entirety.

The 3C5 epitope could only be partially determined using low stringency binding conditions (e.g., 0.1× sample buffer used in antibody preconditioning and the ELISA reactions). The binding results were consistent with the 3C5 epitope partially overlapping with the S70 epitope. The binding results did not rule out the possibility of other regions of hPD-L1 also being bound by 3C5, e.g., as a discontinuous or conformational epitope. As shown in Example 9, below, the 3C5 and S70 antibodies cross compete for binding to human PD-L1 (see Example 9, below), providing further support that the epitopes for the two antibodies are overlapping.

Example 9: Antibody Cross-Blocking

Antibody cross-blocking analysis was conducted by the following method. CHO cells expressing human PD-L1

Figure 11:
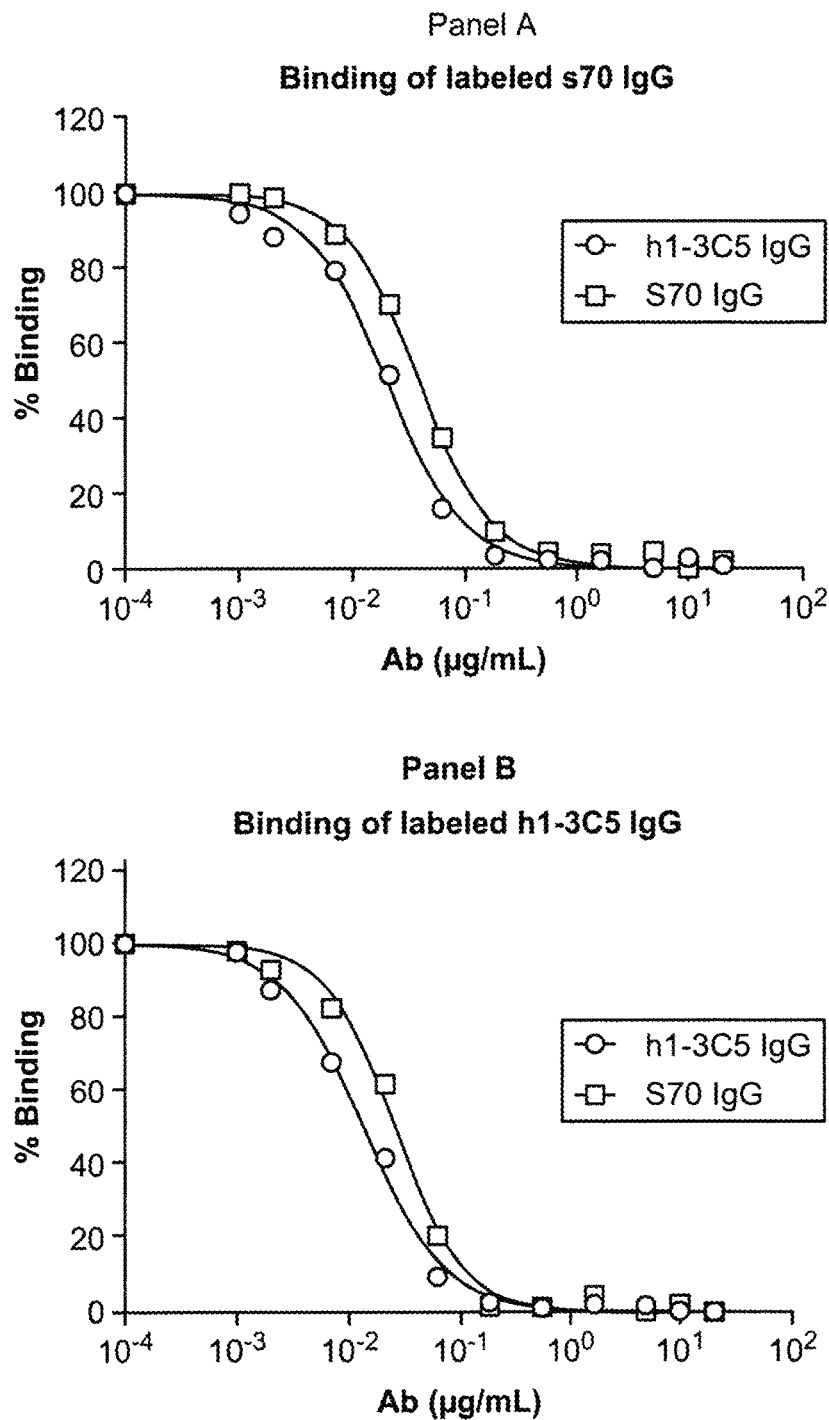
FIG. 11 shows binding of fluorescently labeled anti-PD-L1 antibody S70 IgG (Panel A) or fluorescently labeled anti-PD-L1 antibody 3C5 (Panel B) to recombinant CHO cells expressing human PD-L1, where the cells were previously bound with serial dilutions of unlabeled S70 (closed squares) or 3C5 (closed circles). The results demonstrate that S70 can block binding of 3C5 and 3C5 can block binding of S70.

(20,000-30,000 per reaction) were incubated with unlabeled titrated dilutions of either 3C5 (IgG), S70, or an irrelevant isotype control IgG antibody for 30 min at 4° C. The cells were washed and then were incubated with a constant concentration of Alexa Fluor® 647-labeled 3C5 or S70 (1 µg/mL) for 30 min at 4° C. Fluorescent staining intensities were determined using the FACSCalibur™ system. Competition of by the identical antibody was a positive control while the lack of competition by the irrelevant antibody was a negative control. The cross-blocking results are shown in FIG. 11, Panel A and Panel B. The results demonstrate mutual cross-blocking of binding to human PD-L1 by 3C5 and S70. Although the foregoing invention has been described in some detail by way of illustration and example for purposes of clarity of understanding, it is readily apparent to those of ordinary skill in the art in light of the teachings of this invention that certain changes and modifications can be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles and aspects of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary aspects shown and described herein. Rather, the scope and spirit of present invention is embodied by the appended claims.

The invention claimed is:

1. An isolated anti-PD-L1 antibody, or an antigen-binding fragment thereof, comprising a heavy chain variable region (VH) and a light chain variable region (VL), wherein the antibody or antigen-binding fragment thereof comprises:
   (i) an HVR-H1 comprising the sequence of GFSLT-SYDIS (SEQ ID NO: 4);
   (ii) an HVR-H2 comprising the sequence of VIWTGVGTN (SEQ ID NO: 5); and
   (iii) an HVR-H3 comprising the sequence of DPYYYGMDY (SEQ ID NO: 6);
   (iv) an HVR-L1 comprising the sequence of RASQDIS-IWLS (SEQ ID NO: 1);
   (v) an HVR-L2 comprising the sequence of KASNLHT (SEQ ID NO: 2); and
   (vi) an HVR-L3 comprising the sequence of LQSQSF-PRT (SEQ ID NO: 3); and
   wherein the anti-PD-L1 antibody is capable of binding to human and cynomolgus monkey PD-L1.

2. The anti-PD-L1 antibody or an antigen-binding fragment thereof of claim 1, comprising a VH having at least 90% sequence identity to SEQ ID NO: 45 and a VL having at least 90% sequence identity to SEQ ID NO: 46.

3. The antibody or antigen-binding fragment according to claim 1, which is a chimeric antibody or a humanized antibody.

4. The anti-PD-L1 antibody or antigen-binding fragment thereof of claim 1, comprising a VH having at least 90% sequence identity to the sequence of any one of SEQ ID NOS: 36, 37, 38, 39, 40, 41 or 42 and a VL having at least 90% sequence identity to any one of SEQ ID NOS: 43 or 44.

5. The antibody or antigen-binding fragment thereof of claim 4, wherein the VH comprises the sequence of SEQ ID NO: 36, 37, 38, 39, 40, 41 or 42 and the VL comprises SEQ ID NO: 43 or 44.

6. The antibody or antigen-binding fragment of claim 1, which is bispecific.

7. The antibody or antigen-binding fragment of claim 6, wherein the bispecific antibody or antigen-binding fragment binds to a PD-L1 protein and a cell surface protein.

8. The antibody or antigen-binding fragment of claim 7, wherein the cell surface protein is selected from the group consisting of: CD20, EGFR, HER2, CTLA-4, TIM3, LAG3, VISTA and TIGIT.

9. The antibody or antigen-binding fragment of claim 1, wherein the antigen-binding fragment is selected from the group consisting of: Fab, Fab', F(ab)$_2$, F(ab')$_2$, Fv, and scFv.

10. The antibody or antigen-binding fragment of claim 1, wherein the antibody is an IgG, IgM, IgA, IgD, or IgE isotype.

11. The antibody or antigen-binding fragment of claim 10, wherein the antibody is an IgM isotype.

12. The antibody or antigen-binding fragment of claim 11, wherein the antibody comprises a J-chain.

13. The antibody or antigen-binding fragment of claim 12, wherein the J-chain is a modified J-chain comprising an extraneous binding moiety.

14. The antibody or antigen-binding fragment according to claim 10, wherein the antibody is an IgA isotype, wherein the antibody is a subclass selected from the group consisting of: IgA1 and IgA2, and wherein the antibody comprises a J-chain.

15. The antibody or antigen-binding fragment of claim 1, which is a PD-L1 antagonist.

16. The antibody or antigen-binding fragment thereof of claim 1, wherein the VH comprises the amino acid sequence SEQ ID NO: 45 and the VL comprises the amino acid sequence SEQ ID NO: 46.

17. The antibody or antigen-binding fragment thereof of claim 1, wherein the VH comprises the amino acid sequence SEQ ID NO: 37 and the VL comprises the amino acid sequence SEQ ID NO: 44.

18. A pharmaceutical composition comprising the antibody or antigen-binding fragment thereof of claim 1 and a pharmaceutically-acceptable carrier.

19. A polynucleotide encoding a heavy chain or a light chain of the antibody or antigen-binding fragment of claim 1.

* * * * *

SEQUENCE LISTING

```
<160> NUMBER OF SEQ ID NOS: 71

<210> SEQ ID NO 1
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Arg Ala Ser Gln Asp Ile Ser Ile Trp Leu Ser
1               5                   10

<210> SEQ ID NO 2
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Lys Ala Ser Asn Leu His Thr
1               5

<210> SEQ ID NO 3
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Leu Gln Ser Gln Ser Phe Pro Arg Thr
1               5

<210> SEQ ID NO 4
<211> LENGTH: 10
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 4

Gly Phe Ser Leu Thr Ser Tyr Asp Ile Ser
1               5                   10

<210> SEQ ID NO 5
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Val Ile Trp Thr Gly Val Gly Thr Asn
1               5

<210> SEQ ID NO 6
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Asp Pro Tyr Tyr Tyr Gly Met Asp Tyr
1               5

<210> SEQ ID NO 7
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Gln Val Gln Leu Lys Glu Ser Gly Pro Gly Leu Val Ala Pro Ser Gln
1               5                   10                  15

Ser Leu Ser Ile Thr Cys Thr Val Ser
            20                  25

<210> SEQ ID NO 8
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Gln Val Gln Leu Gln Glu Ser Gly Pro Gly Leu Val Lys Pro Ser Glu
1               5                   10                  15

Thr Leu Ser Leu Thr Cys Thr Val Ser
            20                  25

<210> SEQ ID NO 9
<211> LENGTH: 25
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Gln Val Gln Leu Gln Glu Ser Gly Pro Gly Leu Val Lys Pro Ser Glu
1               5                   10                  15

Thr Leu Ser Ile Thr Cys Thr Val Ser
            20                  25

<210> SEQ ID NO 10
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 11
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Glu Val Gln Leu Val Glu Ser Gly Gly Gly Leu Val Gln Pro Gly Gly
1               5                   10                  15

Ser Leu Arg Ile Ser Cys Ala Val Ser
            20                  25

<210> SEQ ID NO 12
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Trp Val Arg Gln Pro Pro Gly Lys Gly Leu Glu Trp Leu Gly
1               5                   10

<210> SEQ ID NO 13
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Trp Ile Arg Gln Pro Pro Gly Lys Gly Leu Glu Trp Ile Gly
```

<210> SEQ ID NO 14
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Trp Ile Arg Gln Pro Pro Gly Lys Gly Leu Glu Trp Leu Gly
1               5                   10

<210> SEQ ID NO 15
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Trp Val Arg Gln Ala Pro Gly Lys Gly Leu Glu Trp Val Ser
1               5                   10

<210> SEQ ID NO 16
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Trp Val Arg Gln Ala Pro Gly Lys Gly Leu Glu Trp Leu Gly
1               5                   10

<210> SEQ ID NO 17
<211> LENGTH: 39
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Tyr Asn Ser Ala Phe Met Ser Arg Leu Ser Ile Ser Lys Asp Asn Ser
1               5                   10                  15

Lys Ser Gln Val Phe Leu Lys Met Asn Ser Leu Gln Thr Asp Asp Thr
            20                  25                  30

Ala Met Tyr Tyr Cys Val Arg
        35

<210> SEQ ID NO 18
<211> LENGTH: 39
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Tyr Asn Pro Ser Leu Lys Ser Arg Val Thr Ile Ser Val Asp Thr Ser
1               5                   10                  15

Lys Asn Gln Phe Ser Leu Lys Leu Ser Ser Val Thr Ala Ala Asp Thr
            20                  25                  30

Ala Val Tyr Tyr Cys Ala Arg
        35

<210> SEQ ID NO 19
<211> LENGTH: 39
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Tyr Asn Pro Ser Leu Lys Ser Arg Val Thr Ile Ser Lys Asp Thr Ser
1               5                   10                  15

Lys Asn Gln Phe Ser Leu Lys Leu Ser Ser Val Thr Ala Ala Asp Thr
            20                  25                  30

Ala Val Tyr Tyr Cys Ala Arg
        35

<210> SEQ ID NO 20
<211> LENGTH: 39
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Tyr Asn Pro Ser Phe Lys Ser Arg Leu Thr Ile Ser Lys Asp Thr Ser
1               5                   10                  15

Lys Asn Gln Val Ser Leu Lys Met Ser Ser Leu Thr Ala Ala Asp Thr
            20                  25                  30

Ala Val Tyr Tyr Cys Val Arg
        35

<210> SEQ ID NO 21
<211> LENGTH: 39
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Tyr Asn Pro Ser Phe Lys Ser Arg Leu Thr Ile Ser Lys Asp Asn Ser
1               5                   10                  15

Lys Asn Gln Val Ser Leu Lys Met Ser Ser Leu Thr Ala Ala Asp Thr
            20                  25                  30

Ala Val Tyr Tyr Cys Val Arg
        35

<210> SEQ ID NO 22
<211> LENGTH: 39
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic polypeptide"

<400> SEQUENCE: 22

Tyr Ala Asp Ser Val Lys Gly Arg Phe Thr Ile Ser Arg Asp Asn Ser
1               5                   10                  15

Lys Asn Thr Leu Tyr Leu Gln Met Asn Ser Leu Arg Ala Glu Asp Thr
            20                  25                  30

Ala Val Tyr Tyr Cys Ala Arg
            35

<210> SEQ ID NO 23
<211> LENGTH: 39
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Tyr Ala Asp Ser Phe Lys Gly Arg Leu Thr Ile Ser Arg Asp Asn Ser
1               5                   10                  15

Lys Asn Thr Val Tyr Leu Gln Met Asn Ser Leu Arg Ala Glu Asp Thr
            20                  25                  30

Ala Val Tyr Tyr Cys Val Arg
            35

<210> SEQ ID NO 24
<211> LENGTH: 39
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Tyr Ala Asp Ser Phe Lys Gly Arg Leu Thr Ile Ser Lys Asp Asn Ser
1               5                   10                  15

Lys Asn Thr Val Tyr Leu Gln Met Asn Ser Leu Arg Ala Glu Asp Thr
            20                  25                  30

Ala Val Tyr Tyr Cys Val Arg
            35

<210> SEQ ID NO 25
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Trp Gly Gln Gly Thr Ser Val Thr Val Ser Ser
1               5                   10

<210> SEQ ID NO 26
<211> LENGTH: 11
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 26

Trp Gly Gln Gly Thr Leu Val Thr Val Ser Ser
1               5                   10

<210> SEQ ID NO 27
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Asp Ile Gln Met Asn Gln Ser Pro Ser Ser Leu Ser Ala Ser Leu Gly
1               5                   10                  15

Asp Thr Ile Thr Ile Thr Cys
            20

<210> SEQ ID NO 28
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 29
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Asp Ile Gln Met Thr Gln Ser Pro Ser Ser Leu Ser Ala Ser Val Gly
1               5                   10                  15

Asp Arg Ile Thr Ile Thr Cys
            20

<210> SEQ ID NO 30
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Trp Tyr Gln Gln Lys Pro Gly Asn Ile Pro Glu Leu Leu Ile Tyr
1               5                   10                  15

<210> SEQ ID NO 31
```

```
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Trp Tyr Gln Gln Lys Pro Gly Lys Ala Pro Lys Leu Leu Ile Tyr
1               5                   10                  15

<210> SEQ ID NO 32
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Gly Val Pro Pro Arg Phe Ser Gly Ser Gly Ser Gly Thr Asp Phe Thr
1               5                   10                  15

Leu Thr Ile Ser Ser Leu Gln Pro Glu Asp Ile Ala Thr Tyr Tyr Cys
            20                  25                  30

<210> SEQ ID NO 33
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 34
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Phe Gly Gly Gly Thr Lys Leu Glu Ile Lys
1               5                   10

<210> SEQ ID NO 35
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Phe Gly Gln Gly Thr Lys Leu Glu Ile Lys
1               5                   10
```

<210> SEQ ID NO 36
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 36

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Asp Ile Ser Trp Ile Arg Gln Pro Pro Gly Lys Gly Leu Glu Trp Ile
        35                  40                  45

Gly Val Ile Trp Thr Gly Val Gly Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Pro Tyr Tyr Tyr Gly Met Asp Tyr Trp Gly Gln Gly Thr Leu
            100                 105                 110

Val Thr Val Ser Ser
        115

<210> SEQ ID NO 37
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 37

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Asp Ile Ser Trp Ile Arg Gln Pro Pro Gly Lys Gly Leu Glu Trp Leu
        35                  40                  45

Gly Val Ile Trp Thr Gly Val Gly Thr Asn Tyr Asn Pro Ser Leu Lys
    50                  55                  60

Ser Arg Val Thr Ile Ser Lys Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Pro Tyr Tyr Tyr Gly Met Asp Tyr Trp Gly Gln Gly Thr Leu
            100                 105                 110

Val Thr Val Ser Ser
        115

<210> SEQ ID NO 38
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 38

Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Thr Ser Tyr
            20                  25                  30

Asp Ile Ser Trp Val Arg Gln Pro Pro Gly Lys Gly Leu Glu Trp Leu
        35                  40                  45

Gly Val Ile Trp Thr Gly Val Gly Thr Asn Tyr Asn Pro Ser Phe Lys
    50                  55                  60

Ser Arg Leu Thr Ile Ser Lys Asp Thr Ser Lys Asn Gln Val Ser Leu
65                  70                  75                  80

Lys Met Ser Ser Leu Thr Ala Ala Asp Thr Ala Val Tyr Tyr Cys Val
                85                  90                  95

Arg Asp Pro Tyr Tyr Tyr Gly Met Asp Tyr Trp Gly Gln Gly Thr Leu
            100                 105                 110

Val Thr Val Ser Ser
        115

<210> SEQ ID NO 39
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 39

Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Thr Ser Tyr
            20                  25                  30

Asp Ile Ser Trp Ile Arg Gln Pro Pro Gly Lys Gly Leu Glu Trp Leu
        35                  40                  45

Gly Val Ile Trp Thr Gly Val Gly Thr Asn Tyr Asn Pro Ser Phe Lys
    50                  55                  60

Ser Arg Leu Thr Ile Ser Lys Asp Asn Ser Lys Asn Gln Val Ser Leu
65                  70                  75                  80

Lys Met Ser Ser Leu Thr Ala Ala Asp Thr Ala Val Tyr Tyr Cys Val
                85                  90                  95

Arg Asp Pro Tyr Tyr Tyr Gly Met Asp Tyr Trp Gly Gln Gly Thr Leu
            100                 105                 110

Val Thr Val Ser Ser
        115

<210> SEQ ID NO 40
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 40

Glu Val Gln Leu Val Glu Ser Gly Gly Gly Leu Val Gln Pro Gly Gly
1               5                   10                  15

-continued

Ser Leu Arg Leu Ser Cys Ala Ala Ser Gly Phe Ser Leu Thr Ser Tyr
            20                  25                  30

Asp Ile Ser Trp Val Arg Gln Ala Pro Gly Lys Gly Leu Glu Trp Val
        35                  40                  45

Ser Val Ile Trp Thr Gly Val Gly Thr Asn Tyr Ala Asp Ser Val Lys
 50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Pro Tyr Tyr Tyr Gly Met Asp Tyr Trp Gly Gln Gly Thr Leu
            100                 105                 110

Val Thr Val Ser Ser
        115

<210> SEQ ID NO 41
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Glu Val Gln Leu Val Glu Ser Gly Gly Gly Leu Val Gln Pro Gly Gly
1               5                   10                  15

Ser Leu Arg Ile Ser Cys Ala Val Ser Gly Phe Ser Leu Thr Ser Tyr
            20                  25                  30

Asp Ile Ser Trp Val Arg Gln Ala Pro Gly Lys Gly Leu Glu Trp Leu
        35                  40                  45

Gly Val Ile Trp Thr Gly Val Gly Thr Asn Tyr Ala Asp Ser Phe Lys
 50                  55                  60

Gly Arg Leu Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Val
                85                  90                  95

Arg Asp Pro Tyr Tyr Tyr Gly Met Asp Tyr Trp Gly Gln Gly Thr Leu
            100                 105                 110

Val Thr Val Ser Ser
        115

<210> SEQ ID NO 42
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Glu Val Gln Leu Val Glu Ser Gly Gly Gly Leu Val Gln Pro Gly Gly
1               5                   10                  15

Ser Leu Arg Ile Ser Cys Ala Val Ser Gly Phe Ser Leu Thr Ser Tyr
            20                  25                  30

Asp Ile Ser Trp Val Arg Gln Ala Pro Gly Lys Gly Leu Glu Trp Leu
        35                  40                  45

Gly Val Ile Trp Thr Gly Val Gly Thr Asn Tyr Ala Asp Ser Phe Lys
    50                  55                  60

Gly Arg Leu Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Val
                85                  90                  95

Arg Asp Pro Tyr Tyr Tyr Gly Met Asp Tyr Trp Gly Gln Gly Thr Leu
                100                 105                 110

Val Thr Val Ser Ser
        115

<210> SEQ ID NO 43
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ile Trp
                20                  25                  30

Leu Ser Trp Tyr Gln Gln Lys Pro Gly Lys Ala Pro Lys Leu Leu Ile
            35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Ser Gln Ser Phe Pro Arg
                85                  90                  95

Thr Phe Gly Gln Gly Thr Lys Leu Glu Ile Lys
                100                 105

<210> SEQ ID NO 44
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Asp Ile Gln Met Thr Gln Ser Pro Ser Ser Leu Ser Ala Ser Val Gly
1               5                   10                  15

Asp Arg Ile Thr Ile Thr Cys Arg Ala Ser Gln Asp Ile Ser Ile Trp
                20                  25                  30

Leu Ser Trp Tyr Gln Gln Lys Pro Gly Lys Ala Pro Lys Leu Leu Ile
            35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Ser Gln Ser Phe Pro Arg
                85                  90                  95

Thr Phe Gly Gln Gly Thr Lys Leu Glu Ile Lys

<210> SEQ ID NO 45
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 45

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Asp Ile Ser Trp Val Arg Gln Pro Pro Gly Lys Gly Leu Glu Trp Leu
        35                  40                  45

Gly Val Ile Trp Thr Gly Val Gly Thr Asn Tyr Asn Ser Ala Phe Met
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Val
                85                  90                  95

Arg Asp Pro Tyr Tyr Tyr Gly Met Asp Tyr Trp Gly Gln Gly Thr Ser
            100                 105                 110

Val Thr Val Ser Ser
        115

<210> SEQ ID NO 46
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 46

Asp Ile Gln Met Asn Gln Ser Pro Ser Ser Leu Ser Ala Ser Leu Gly
1               5                   10                  15

Asp Thr Ile Thr Ile Thr Cys Arg Ala Ser Gln Asp Ile Ser Ile Trp
            20                  25                  30

Leu Ser Trp Tyr Gln Gln Lys Pro Gly Asn Ile Pro Glu Leu Leu Ile
        35                  40                  45

Tyr Lys Ala Ser Asn Leu His Thr Gly Val Pro Pro Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Leu Gln Ser Gln Ser Phe Pro Arg
                85                  90                  95

Thr Phe Gly Gly Gly Thr Lys Leu Glu Ile Lys
            100                 105

<210> SEQ ID NO 47
<211> LENGTH: 137
<212> TYPE: PRT
<213> ORGANISM: Homo sapiens

<400> SEQUENCE: 47

-continued

```
Gln Glu Asp Glu Arg Ile Val Leu Val Asp Asn Lys Cys Lys Cys Ala
1               5                   10                  15

Arg Ile Thr Ser Arg Ile Arg Ser Ser Glu Asp Pro Asn Glu Asp
            20                  25                  30

Ile Val Glu Arg Asn Ile Arg Ile Ile Val Pro Leu Asn Asn Arg Glu
        35                  40                  45

Asn Ile Ser Asp Pro Thr Ser Pro Leu Arg Thr Arg Phe Val Tyr His
    50                  55                  60

Leu Ser Asp Leu Cys Lys Lys Cys Asp Pro Thr Glu Val Glu Leu Asp
65                  70                  75                  80

Asn Gln Ile Val Thr Ala Thr Gln Ser Asn Ile Cys Asp Glu Asp Ser
                85                  90                  95

Ala Thr Glu Thr Cys Tyr Thr Tyr Asp Arg Asn Lys Cys Tyr Thr Ala
            100                 105                 110

Val Val Pro Leu Val Tyr Gly Gly Glu Thr Lys Met Val Glu Thr Ala
        115                 120                 125

Leu Thr Pro Asp Ala Cys Tyr Pro Asp
    130                 135
```

<210> SEQ ID NO 48
<211> LENGTH: 290
<212> TYPE: PRT
<213> ORGANISM: Homo sapiens

<400> SEQUENCE: 48

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240
```

```
Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290

<210> SEQ ID NO 49
<211> LENGTH: 470
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Lys Glu Ser Gly
            20                  25                  30

Pro Gly Leu Val Ala Pro Ser Gln Ser Leu Ser Ile Thr Cys Thr Val
        35                  40                  45

Ser Gly Phe Ser Leu Thr Ser Tyr Asp Ile Ser Trp Val Arg Gln Pro
    50                  55                  60

Pro Gly Lys Gly Leu Glu Trp Leu Gly Val Ile Trp Thr Gly Val Gly
65                  70                  75                  80

Thr Asn Tyr Asn Ser Ala Phe Met Ser Arg Leu Ser Ile Ser Lys Asp
                85                  90                  95

Asn Ser Lys Ser Gln Val Phe Leu Lys Met Asn Ser Leu Gln Thr Asp
            100                 105                 110

Asp Thr Ala Met Tyr Tyr Cys Val Arg Asp Pro Tyr Tyr Tyr Gly Met
        115                 120                 125

Asp Tyr Trp Gly Gln Gly Thr Ser Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285
```

Asp Val Ser His Glu Asp Pro Glu Val Lys Phe Asn Trp Tyr Val Asp
            290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
450                 455                 460

Leu Ser Leu Ser Pro Gly
465                 470

<210> SEQ ID NO 50
<211> LENGTH: 594
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Lys Glu Ser Gly
            20                  25                  30

Pro Gly Leu Val Ala Pro Ser Gln Ser Leu Ser Ile Thr Cys Thr Val
        35                  40                  45

Ser Gly Phe Ser Leu Thr Ser Tyr Asp Ile Ser Trp Val Arg Gln Pro
    50                  55                  60

Pro Gly Lys Gly Leu Glu Trp Leu Gly Val Ile Trp Thr Gly Val Gly
65                  70                  75                  80

Thr Asn Tyr Asn Ser Ala Phe Met Ser Arg Leu Ser Ile Ser Lys Asp
                85                  90                  95

Asn Ser Lys Ser Gln Val Phe Leu Lys Met Asn Ser Leu Gln Thr Asp
            100                 105                 110

Asp Thr Ala Met Tyr Tyr Cys Val Arg Asp Pro Tyr Tyr Tyr Gly Met
        115                 120                 125

Asp Tyr Trp Gly Gln Gly Thr Ser Val Thr Val Ser Ser Gly Ser Ala
    130                 135                 140

Ser Ala Pro Thr Leu Phe Pro Leu Val Ser Cys Glu Asn Ser Pro Ser
145                 150                 155                 160

Asp Thr Ser Ser Val Ala Val Gly Cys Leu Ala Gln Asp Phe Leu Pro

```
                165                 170                 175
Asp Ser Ile Thr Phe Ser Trp Lys Tyr Lys Asn Asn Ser Asp Ile Ser
                    180                 185                 190

Ser Thr Arg Gly Phe Pro Ser Val Leu Arg Gly Gly Lys Tyr Ala Ala
                    195                 200                 205

Thr Ser Gln Val Leu Leu Pro Ser Lys Asp Val Met Gln Gly Thr Asp
    210                 215                 220

Glu His Val Val Cys Lys Val Gln His Pro Asn Gly Asn Lys Glu Lys
225                 230                 235                 240

Asn Val Pro Leu Pro Val Ile Ala Glu Leu Pro Pro Lys Val Ser Val
                245                 250                 255

Phe Val Pro Pro Arg Asp Gly Phe Phe Gly Asn Pro Arg Lys Ser Lys
                260                 265                 270

Leu Ile Cys Gln Ala Thr Gly Phe Ser Pro Arg Gln Ile Gln Val Ser
                275                 280                 285

Trp Leu Arg Glu Gly Lys Gln Val Gly Ser Gly Val Thr Thr Asp Gln
    290                 295                 300

Val Gln Ala Glu Ala Lys Glu Ser Gly Pro Thr Thr Tyr Lys Val Thr
305                 310                 315                 320

Ser Thr Leu Thr Ile Lys Glu Ser Asp Trp Leu Ser Gln Ser Met Phe
                325                 330                 335

Thr Cys Arg Val Asp His Arg Gly Leu Thr Phe Gln Gln Asn Ala Ser
                340                 345                 350

Ser Met Cys Val Pro Asp Gln Asp Thr Ala Ile Arg Val Phe Ala Ile
        355                 360                 365

Pro Pro Ser Phe Ala Ser Ile Phe Leu Thr Lys Ser Thr Lys Leu Thr
    370                 375                 380

Cys Leu Val Thr Asp Leu Thr Thr Tyr Asp Ser Val Thr Ile Ser Trp
385                 390                 395                 400

Thr Arg Gln Asn Gly Glu Ala Val Lys Thr His Thr Asn Ile Ser Glu
                405                 410                 415

Ser His Pro Asn Ala Thr Phe Ser Ala Val Gly Glu Ala Ser Ile Cys
                420                 425                 430

Glu Asp Asp Trp Asn Ser Gly Glu Arg Phe Thr Cys Thr Val Thr His
        435                 440                 445

Thr Asp Leu Pro Ser Pro Leu Lys Gln Thr Ile Ser Arg Pro Lys Gly
    450                 455                 460

Val Ala Leu His Arg Pro Asp Val Tyr Leu Leu Pro Pro Ala Arg Glu
465                 470                 475                 480

Gln Leu Asn Leu Arg Glu Ser Ala Thr Ile Thr Cys Leu Val Thr Gly
                485                 490                 495

Phe Ser Pro Ala Asp Val Phe Val Gln Trp Met Gln Arg Gly Gln Pro
                500                 505                 510

Leu Ser Pro Glu Lys Tyr Val Thr Ser Ala Pro Met Pro Glu Pro Gln
        515                 520                 525

Ala Pro Gly Arg Tyr Phe Ala His Ser Ile Leu Thr Val Ser Glu Glu
    530                 535                 540

Glu Trp Asn Thr Gly Glu Thr Tyr Thr Cys Val Val Ala His Glu Ala
545                 550                 555                 560

Leu Pro Asn Arg Val Thr Glu Arg Thr Val Asp Lys Ser Thr Gly Lys
                565                 570                 575

Pro Thr Leu Tyr Asn Val Ser Leu Val Met Ser Asp Thr Ala Gly Thr
                580                 585                 590
```

Cys Tyr

<210> SEQ ID NO 51
<211> LENGTH: 234
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 51

Met Glu Thr Asp Thr Leu Leu Leu Trp Val Leu Leu Trp Val Pro
1               5                   10                  15

Gly Ser Thr Gly Asp Ile Gln Met Asn Gln Ser Pro Ser Ser Leu Ser
                20                  25                  30

Ala Ser Leu Gly Asp Thr Ile Thr Ile Thr Cys Arg Ala Ser Gln Asp
            35                  40                  45

Ile Ser Ile Trp Leu Ser Trp Tyr Gln Gln Lys Pro Gly Asn Ile Pro
50                  55                  60

Glu Leu Leu Ile Tyr Lys Ala Ser Asn Leu His Thr Gly Val Pro Pro
65                  70                  75                  80

Arg Phe Ser Gly Ser Gly Ser Gly Thr Asp Phe Thr Leu Thr Ile Ser
                85                  90                  95

Ser Leu Gln Pro Glu Asp Ile Ala Thr Tyr Tyr Cys Leu Gln Ser Gln
            100                 105                 110

Ser Phe Pro Arg Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 52
<211> LENGTH: 470
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 52

Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Gln Glu Ser Gly
                20                  25                  30

Pro Gly Leu Val Lys Pro Ser Glu Thr Leu Ser Leu Thr Cys Thr Val

```
                35                  40                  45
Ser Gly Phe Ser Leu Thr Ser Tyr Asp Ile Ser Trp Ile Arg Gln Pro
 50                  55                  60

Pro Gly Lys Gly Leu Glu Trp Ile Gly Val Ile Trp Thr Gly Val Gly
 65                  70                  75                  80

Thr Asn Tyr Asn Pro Ser Leu Lys Ser Arg Val Thr Ile Ser Val Asp
                 85                  90                  95

Thr Ser Lys Asn Gln Phe Ser Leu Lys Leu Ser Ser Val Thr Ala Ala
                100                 105                 110

Asp Thr Ala Val Tyr Tyr Cys Ala Arg Asp Pro Tyr Tyr Gly Met
                115                 120                 125

Asp Tyr Trp Gly Gln Gly Thr Leu Val Thr Val Ser Ser Ala Ser Thr
130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
                180                 185                 190

Thr Phe Pro Ala Val Leu Gln Ser Ser Gly Leu Tyr Ser Leu Ser Ser
                195                 200                 205

Val Val Thr Val Pro Ser Ser Ser Leu Gly Thr Gln Thr Tyr Ile Cys
210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
                260                 265                 270

Asp Thr Leu Met Ile Ser Arg Thr Pro Glu Val Thr Cys Val Val Val
                275                 280                 285

Asp Val Ser His Glu Asp Pro Glu Val Lys Phe Asn Trp Tyr Val Asp
290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
                340                 345                 350

Pro Ala Pro Ile Glu Lys Thr Ile Ser Lys Ala Lys Gly Gln Pro Arg
                355                 360                 365

Glu Pro Gln Val Tyr Thr Leu Pro Pro Ser Arg Asp Glu Leu Thr Lys
                370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
                420                 425                 430

Lys Leu Thr Val Asp Lys Ser Arg Trp Gln Gln Gly Asn Val Phe Ser
                435                 440                 445

Cys Ser Val Met His Glu Ala Leu His Asn His Tyr Thr Gln Lys Ser
450                 455                 460
```

```
Leu Ser Leu Ser Pro Gly
465                 470

<210> SEQ ID NO 53
<211> LENGTH: 470
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Gln Glu Ser Gly
            20                  25                  30

Pro Gly Leu Val Lys Pro Ser Glu Thr Leu Ser Leu Thr Cys Thr Val
        35                  40                  45

Ser Gly Phe Ser Leu Thr Ser Tyr Asp Ile Ser Trp Ile Arg Gln Pro
    50                  55                  60

Pro Gly Lys Gly Leu Glu Trp Leu Gly Val Ile Trp Thr Gly Val Gly
65                  70                  75                  80

Thr Asn Tyr Asn Pro Ser Leu Lys Ser Arg Val Thr Ile Ser Lys Asp
                85                  90                  95

Thr Ser Lys Asn Gln Phe Ser Leu Lys Leu Ser Ser Val Thr Ala Ala
            100                 105                 110

Asp Thr Ala Val Tyr Tyr Cys Ala Arg Asp Pro Tyr Tyr Tyr Gly Met
        115                 120                 125

Asp Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335
```

```
Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly
465                 470

<210> SEQ ID NO 54
<211> LENGTH: 470
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Gln Glu Ser Gly
            20                  25                  30

Pro Gly Leu Val Lys Pro Ser Glu Thr Leu Ser Ile Thr Cys Thr Val
        35                  40                  45

Ser Gly Phe Ser Leu Thr Ser Tyr Asp Ile Ser Trp Val Arg Gln Pro
    50                  55                  60

Pro Gly Lys Gly Leu Glu Trp Leu Gly Val Ile Trp Thr Gly Val Gly
65                  70                  75                  80

Thr Asn Tyr Asn Pro Ser Phe Lys Ser Arg Leu Thr Ile Ser Lys Asp
                85                  90                  95

Thr Ser Lys Asn Gln Val Ser Leu Lys Met Ser Ser Leu Thr Ala Ala
            100                 105                 110

Asp Thr Ala Val Tyr Tyr Cys Val Arg Asp Pro Tyr Tyr Tyr Gly Met
        115                 120                 125

Asp Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
```

```
                210                 215                 220
Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
                260                 265                 270

Asp Thr Leu Met Ile Ser Arg Thr Pro Glu Val Thr Cys Val Val Val
                275                 280                 285

Asp Val Ser His Glu Asp Pro Glu Val Lys Phe Asn Trp Tyr Val Asp
290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
                340                 345                 350

Pro Ala Pro Ile Glu Lys Thr Ile Ser Lys Ala Lys Gly Gln Pro Arg
                355                 360                 365

Glu Pro Gln Val Tyr Thr Leu Pro Pro Ser Arg Asp Glu Leu Thr Lys
370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
                420                 425                 430

Lys Leu Thr Val Asp Lys Ser Arg Trp Gln Gln Gly Asn Val Phe Ser
                435                 440                 445

Cys Ser Val Met His Glu Ala Leu His Asn His Tyr Thr Gln Lys Ser
                450                 455                 460

Leu Ser Leu Ser Pro Gly
465                 470

<210> SEQ ID NO 55
<211> LENGTH: 470
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Gln Glu Ser Gly
                20                  25                  30

Pro Gly Leu Val Lys Pro Ser Glu Thr Leu Ser Ile Thr Cys Thr Val
                35                  40                  45

Ser Gly Phe Ser Leu Thr Ser Tyr Asp Ile Ser Trp Ile Arg Gln Pro
            50                  55                  60

Pro Gly Lys Gly Leu Glu Trp Leu Gly Val Ile Trp Thr Gly Val Gly
65                  70                  75                  80

Thr Asn Tyr Asn Pro Ser Phe Lys Ser Arg Leu Thr Ile Ser Lys Asp
                85                  90                  95
```

Asn Ser Lys Asn Gln Val Ser Leu Lys Met Ser Ser Leu Thr Ala Ala
            100                 105                 110

Asp Thr Ala Val Tyr Tyr Cys Val Arg Asp Pro Tyr Tyr Gly Met
        115                 120                 125

Asp Tyr Trp Gly Gln Gly Thr Leu Val Thr Val Ser Ser Ala Ser Thr
130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly
465                 470

<210> SEQ ID NO 56
<211> LENGTH: 234
<212> TYPE: PRT
<213> ORGANISM: Artificial Sequence
<220> FEATURE:

<221> NAME/KEY: source
<223> OTHER INFORMATION: /note="Description of Artificial Sequence: Synthetic polypeptide"

<400> SEQUENCE: 56

```
Met Glu Thr Asp Thr Leu Leu Leu Trp Val Leu Leu Trp Val Pro
1               5                   10                  15

Gly Ser Thr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Ile Ser Ile Trp Leu Ser Trp Tyr Gln Gln Lys Pro Gly Lys Ala Pro
50                  55                  60

Lys Leu Leu Ile Tyr Lys Ala Ser Asn Leu His Thr Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Leu Gln Ser Gln
            100                 105                 110

Ser Phe Pro Arg Thr Phe Gly Gln Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 57
<211> LENGTH: 234
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 57

```
Met Glu Thr Asp Thr Leu Leu Leu Trp Val Leu Leu Trp Val Pro
1               5                   10                  15

Gly Ser Thr Gly Asp Ile Gln Met Thr Gln Ser Pro Ser Ser Leu Ser
            20                  25                  30

Ala Ser Val Gly Asp Arg Ile Thr Ile Thr Cys Arg Ala Ser Gln Asp
        35                  40                  45

Ile Ser Ile Trp Leu Ser Trp Tyr Gln Gln Lys Pro Gly Lys Ala Pro
50                  55                  60

Lys Leu Leu Ile Tyr Lys Ala Ser Asn Leu His Thr Gly Val Pro Ser
65                  70                  75                  80

Arg Phe Ser Gly Ser Gly Ser Gly Thr Asp Phe Thr Leu Thr Ile Ser
```

```
                    85                  90                  95

Ser Leu Gln Pro Glu Asp Phe Ala Thr Tyr Tyr Cys Leu Gln Ser Gln
            100                 105                 110

Ser Phe Pro Arg Thr Phe Gly Gln Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 58
<211> LENGTH: 11
<212> TYPE: PRT
<213> ORGANISM: Unknown
<220> FEATURE:
<221> NAME/KEY: source
<223> OTHER INFORMATION: /note="Description of Unknown:
      Albumin binding peptide"

<400> SEQUENCE: 58

Asp Leu Cys Leu Arg Asp Trp Gly Cys Leu Trp
1               5                   10

<210> SEQ ID NO 59
<211> LENGTH: 11
<212> TYPE: PRT
<213> ORGANISM: Unknown
<220> FEATURE:
<221> NAME/KEY: source
<223> OTHER INFORMATION: /note="Description of Unknown:
      Albumin binding peptide"

<400> SEQUENCE: 59

Asp Ile Cys Leu Pro Arg Trp Gly Cys Leu Trp
1               5                   10

<210> SEQ ID NO 60
<211> LENGTH: 15
<212> TYPE: PRT
<213> ORGANISM: Unknown
<220> FEATURE:
<221> NAME/KEY: source
<223> OTHER INFORMATION: /note="Description of Unknown:
      Albumin binding peptide"

<400> SEQUENCE: 60

Met Glu Asp Ile Cys Leu Pro Arg Trp Gly Cys Leu Trp Gly Asp
1               5                   10                  15

<210> SEQ ID NO 61
<211> LENGTH: 20
<212> TYPE: PRT
<213> ORGANISM: Unknown
```

```
<220> FEATURE:
<221> NAME/KEY: source
<223> OTHER INFORMATION: /note="Description of Unknown:
      Albumin binding peptide"

<400> SEQUENCE: 61

Gln Arg Leu Met Glu Asp Ile Cys Leu Pro Arg Trp Gly Cys Leu Trp
1               5                   10                  15

Glu Asp Asp Glu
            20

<210> SEQ ID NO 62
<211> LENGTH: 20
<212> TYPE: PRT
<213> ORGANISM: Unknown
<220> FEATURE:
<221> NAME/KEY: source
<223> OTHER INFORMATION: /note="Description of Unknown:
      Albumin binding peptide"

<400> SEQUENCE: 62

Gln Gly Leu Ile Gly Asp Ile Cys Leu Pro Arg Trp Gly Cys Leu Trp
1               5                   10                  15

Gly Arg Ser Val
            20

<210> SEQ ID NO 63
<211> LENGTH: 21
<212> TYPE: PRT
<213> ORGANISM: Unknown
<220> FEATURE:
<221> NAME/KEY: source
<223> OTHER INFORMATION: /note="Description of Unknown:
      Albumin binding peptide"

<400> SEQUENCE: 63

Gln Gly Leu Ile Gly Asp Ile Cys Leu Pro Arg Trp Gly Cys Leu Trp
1               5                   10                  15

Gly Arg Ser Val Lys
            20

<210> SEQ ID NO 64
<211> LENGTH: 15
<212> TYPE: PRT
<213> ORGANISM: Unknown
<220> FEATURE:
<221> NAME/KEY: source
<223> OTHER INFORMATION: /note="Description of Unknown:
      Albumin binding peptide"

<400> SEQUENCE: 64

Glu Asp Ile Cys Leu Pro Arg Trp Gly Cys Leu Trp Glu Asp Asp
1               5                   10                  15

<210> SEQ ID NO 65
<211> LENGTH: 18
<212> TYPE: PRT
<213> ORGANISM: Unknown
<220> FEATURE:
<221> NAME/KEY: source
<223> OTHER INFORMATION: /note="Description of Unknown:
      Albumin binding peptide"

<400> SEQUENCE: 65

Arg Leu Met Glu Asp Ile Cys Leu Pro Arg Trp Gly Cys Leu Trp Glu
1               5                   10                  15
```

Asp Asp

<210> SEQ ID NO 66
<211> LENGTH: 16
<212> TYPE: PRT
<213> ORGANISM: Unknown
<220> FEATURE:
<221> NAME/KEY: source
<223> OTHER INFORMATION: /note="Description of Unknown:
      Albumin binding peptide"

<400> SEQUENCE: 66

Met Glu Asp Ile Cys Leu Pro Arg Trp Gly Cys Leu Trp Glu Asp Asp
1               5                   10                  15

<210> SEQ ID NO 67
<211> LENGTH: 15
<212> TYPE: PRT
<213> ORGANISM: Unknown
<220> FEATURE:
<221> NAME/KEY: source
<223> OTHER INFORMATION: /note="Description of Unknown:
      Albumin binding peptide"

<400> SEQUENCE: 67

Met Glu Asp Ile Cys Leu Pro Arg Trp Gly Cys Leu Trp Glu Asp
1               5                   10                  15

<210> SEQ ID NO 68
<211> LENGTH: 18
<212> TYPE: PRT
<213> ORGANISM: Unknown
<220> FEATURE:
<221> NAME/KEY: source
<223> OTHER INFORMATION: /note="Description of Unknown:
      Albumin binding peptide"

<400> SEQUENCE: 68

Arg Leu Met Glu Asp Ile Cys Leu Ala Arg Trp Gly Cys Leu Trp Glu
1               5                   10                  15

Asp Asp

<210> SEQ ID NO 69
<211> LENGTH: 20
<212> TYPE: PRT
<213> ORGANISM: Unknown
<220> FEATURE:
<221> NAME/KEY: source
<223> OTHER INFORMATION: /note="Description of Unknown:
      Albumin binding peptide"

<400> SEQUENCE: 69

Glu Val Arg Ser Phe Cys Thr Arg Trp Pro Ala Glu Lys Ser Cys Lys
1               5                   10                  15

Pro Leu Arg Gly
            20

<210> SEQ ID NO 70
<211> LENGTH: 20
<212> TYPE: PRT
<213> ORGANISM: Unknown
<220> FEATURE:
<221> NAME/KEY: source
<223> OTHER INFORMATION: /note="Description of Unknown:
      Albumin binding peptide"

<400> SEQUENCE: 70

```
Arg Ala Pro Glu Ser Phe Val Cys Tyr Trp Glu Thr Ile Cys Phe Glu
1               5                   10                  15

Arg Ser Glu Gln
            20

<210> SEQ ID NO 71
<211> LENGTH: 11
<212> TYPE: PRT
<213> ORGANISM: Unknown
<220> FEATURE:
<221> NAME/KEY: source
<223> OTHER INFORMATION: /note="Description of Unknown:
      Albumin binding peptide"

<400> SEQUENCE: 71

Glu Met Cys Tyr Phe Pro Gly Ile Cys Trp Met
1               5                   10
```